United States Patent
Zhan

(10) Patent No.: US 12,018,307 B2
(45) Date of Patent: Jun. 25, 2024

(54) PROCESS FOR PRODUCING A GLUCURONIDE AND GENETICALLY MODIFIED MICROORGANISMS USEFUL IN THIS PROCESS

(71) Applicant: Jixun Zhan, North Logan, UT (US)

(72) Inventor: Jixun Zhan, North Logan, UT (US)

(73) Assignee: UTAH STATE UNIVERSITY, North Logan, UT (US)

( * ) Notice: Subject to any disclaimer, the term of this patent is extended or adjusted under 35 U.S.C. 154(b) by 0 days.

(21) Appl. No.: 17/822,733

(22) Filed: Aug. 26, 2022

(65) Prior Publication Data

US 2023/0142611 A1    May 11, 2023

Related U.S. Application Data

(60) Provisional application No. 63/273,136, filed on Oct. 28, 2021.

(51) Int. Cl.
| | | |
|---|---|---|
| C12P 19/60 | (2006.01) | |
| A61K 31/05 | (2006.01) | |
| C12N 9/04 | (2006.01) | |
| C12N 9/10 | (2006.01) | |
| C12N 9/12 | (2006.01) | |
| C12N 15/62 | (2006.01) | |
| C12N 15/63 | (2006.01) | |

(52) U.S. Cl.
CPC .............. *C12P 19/60* (2013.01); *A61K 31/05* (2013.01); *C12N 9/0006* (2013.01); *C12N 9/1051* (2013.01); *C12N 9/1241* (2013.01); *C12N 15/62* (2013.01); *C12N 15/63* (2013.01); *C12Y 101/01022* (2013.01); *C12Y 204/01017* (2013.01); *C12Y 207/07009* (2013.01)

(58) Field of Classification Search
CPC .......... C12P 19/60; C12P 19/46; A61K 31/05; C12N 9/0006; C12N 9/1051; C12N 9/1241; C12N 15/62; C12N 15/63; C12N 15/52; C12Y 101/01022; C12Y 204/01017; C12Y 207/07009
See application file for complete search history.

(56) References Cited

PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Ren et al., Applied Microbiology and Biotechnology 106:1165-1183, Jan. 27, 2022.*
Singh et al., Current Protein and Peptide Science 19(1):5-15, 2018.*
Sadowski et al., Current Opinion in Structural Biology 19:357-362, 2009.*
Almeida AF, Santos CuN, Ventura MR (2017) Synthesis of new sulfated and glucuronated metabolites of dietary phenolic compounds identified in human biological samples. J Agric Food Chem 65(31):6460-6466.
Briggs B, Baker P, Belvo M, Black T, Getman B, Kemp C, Muth W, Perun T, Strobel Jr R, Paschal J (1999) Microbial process for preparation of glucuronides of raloxifene. J Ind Microbiol Biot 23(3):194-197.
Cai Z, Huang J, Luo H, Lei X, Yang Z, Mai Y, Liu Z (2013) Role of glucose transporters in the intestinal absorption of gastrodin, a highly water-soluble drug with good oral bioavailability. J Drug Target 21(6):574-580.
Chung SY, Seki H, Fujisawa Y, Shimoda Y, Hiraga S, Nomura Y, Saito K, Ishimoto M, Muranaka T (2020) A cellulose synthase-derived enzyme catalyses 3-O-glucuronosylation in saponin biosynthesis. Nat Commun 11(1):1-11.
De Bruyn F, Maertens J, Beauprez J, Soetaert W, De Mey M (2015) Biotechnological advances in UDP-sugar based glycosylation of small molecules. Biotechnol Adv 33(2):288-302.
De Wildt SN, Kearns GL, Leeder JS, van den Anker JN (1999) Glucuronidation in humans. Clin Pharmacokinet 36(6):439-452.
Engstrom KM, Daanen JF, Wagaw S, Stewart AO (2006) Gram scale synthesis of the glucuronide metabolite of ABT-724. J Org Chem 71(22):8378-8383.
Fidan O, Yan R, Zhu D, Zhan J (2019) Improved production of antifungal angucycline Sch47554 by manipulating three regulatory genes in *Streptomyces* sp. SCC-2136. Appl Biochem Biotechnol 66(4):517-526.
Francioso A, Mastromarino P, Restignoli R, Boffi A, d'Erme M, Mosca L (2014) Improved stability of trans-resveratrol in aqueous solutions by carboxymethylated (1,3/1,6)-β-D-glucan. J Agric Food Chem 62(7):1520-1525.
Harborne JB, Baxter H (1999) The handbook of natural flavonoids. vol. 1 and vol. 2. John Wiley and Sons.
Jeon YO, Lee J-S, Lee HG (2016) Improving solubility, stability, and cellular uptake of resveratrol by nanoencapsulation with chitosan and γ-poly (glutamic acid). Colloids Surf B 147:224-233.
Kaminaga Y, Nagatsu A, Akiyama T, Sugimoto N, Yamazaki T, Maitani T, Mizukami H (2003) Production of unnatural glucosides of curcumin with drastically enhanced water solubility by cell suspension cultures of Catharanthus roseus. FEBS Lett 555(2):311-316.
Kim S-K (2016) Marine Enzymes Biotechnology: Production and Industrial Applications, Part II—Marine Organisms Producing Enzymes, vol. 79, 1st edition. Academic Press.
King RE, Bomser JA, Min DB (2006) Bioactivity of resveratrol. Compr Rev Food Sci F 5(3):65-70.

(Continued)

*Primary Examiner* — Delia M Ramirez
(74) *Attorney, Agent, or Firm* — Booth Udall Fuller, PLC; Rodney J. Fuller

(57) ABSTRACT

The present invention relates to an in vitro or in vivo process for producing a glucuronide comprising a glucuronic acid moiety bound to a phenolic hydroxyl group or a phenolic carboxyl group. Also provided are expression vectors, nucleic acids, polypeptides, and recombinant microbial cells useful in carrying out the process and prodrugs produced by the process.

11 Claims, 24 Drawing Sheets

Specification includes a Sequence Listing.

(56) References Cited

PUBLICATIONS

Li Y, Baldauf S, Lim E-K, Bowles DJ (2001) Phylogenetic analysis of the UDP-glycosyltransferase multigene family of *Arabidopsis thaliana*. J Biol Chem 276(6):4338-4343.

Marvalin C, Azerad R (2011a) Microbial glucuronidation of polyphenols. J Mol Catal B Enzym 73(1-4):43-52.

Marvalin C, Azerad R (2011b) Microbial production of phase I and phase II metabolites of propranolol. Xenobiotica 41(3):175-186.

Osmani SA, Halkjær Hansen E, Malien-Aubert C, Olsen C-E, Bak S, Lindberg Møller B (2009) Effect of glucuronosylation on anthocyanin color stability. J Agric Food Chem 57(8):3149-3155.

Pandey RP, Parajuli P, Shin JY, Lee J, Lee S, Hong Y-S, Park YI, Kim JS, Sohng JK (2014) Enzymatic biosynthesis of novel resveratrol glucoside and glycoside derivatives. Appl Environ Microbiol 80(23):7235-7243.

Paul D, Standifer KM, Inturrisi CE, Pasternak G (1989) Pharmacological characterization of morphine-6 B-glucuronide, a very potent morphine metabolite. J Pharmacol Exp Ther 251(2):477-483.

Pervaiz S (2003) Resveratrol: from grapevines to mammalian biology. FASEB J 17(14):1975-1985.

Priyadharsini P, Dhanasekaran D (2015) Diversity of soil allelopathic Actinobacteria in Tiruchirappalli district, Tamilnadu, India. J Saudi Soc Agric Sci 14(1):54-60.

Regev-Shoshani G, Shoseyov O, Bilkis I, Kerem Z (2003) Glycosylation of resveratrol protects it from enzymic oxidation. Biochem J 374(1):157-163.

Remya M, Vijayakumar R (2008) Isolation and characterization of marine antagonistic actinomycetes from west coast of India. Med Biol 15(1):13-19.

Rice-Evans C (2001) Flavonoid antioxidants. Curr Med Chem 8(7):797-807.

Ridder L, van der Hooft JJ, Verhoeven S, de Vos RC, van Schaik R, Vervoort J (2012) Substructure-based annotation of high-resolution multistage MSn spectral trees. Rapid Commun Mass Sp 26(20):2461-2471.

Romero-Pérez AI, Ibern-Gómez M, Lamuela-Raventós RM, de la Torre-Boronat MC (1999) Piceid, the major resveratrol derivative in grape juices. J Agric Food Chem 47(4):1533-1536.

Sharipova R, Andreeva O, Strobykina IY, Voloshina A, Strobykina A, Kataev V (2017) Synthesis and antimicrobial activity of glucuronosyl derivatives of steviolbioside from Stevia rebaudiana. Chem Nat Compd 53(6):1107-1111.

Shimoda K, Hamada M, Hamada H, Takemoto M, Hamada H (2013) Synthesis of resveratrol glycosides by cultured plant cells. Nat Prod Commun 8(7):907-909.

Smith MT, Watt JA, Cramond T (1990) Morphine-3-glucuronide-a potent antagonist of morphine analgesia. Life Sci 47(6):579-585.

Stachulski A, Jenkins G (1998) The synthesis of O-glucuronides. Nat Prod Rep 15(2):173-186.

Thilakarathna SH, Rupasinghe H (2013) Flavonoid bioavailability and attempts for bioavailability enhancement. Nutrients 5(9):3367-3387.

Thorson JS, Barton WA, Hoffmeister D, Albermann C, Nikolov DB (2004) Structure-based enzyme engineering and its impact on in vitro glycorandomization. ChemBioChem 5(1):16-25.

Thuan NH, Trung NT, Cuong NX, Van Cuong D, Van Quyen D, Malla S (2018) *Escherichia coli* modular coculture system for resveratrol glucosides production. World J Microb Biot 34(6):1-13.

Tsao R (2010) Chemistry and biochemistry of dietary polyphenols. Nutrients 2(12):1231-1246.

Uesugi D, Hamada H, Shimoda K, Kubota N, Ozaki S-i, Nagatani N (2017) Synthesis, oxygen radical absorbance capacity, and tyrosinase inhibitory activity of glycosides of resveratrol, pterostilbene, and pinostilbene. Biosci Biotechnol Biochem 81(2):226-230.

Van der Hooft JJ, de Vos RC, Mihaleva V, Bino RJ, Ridder L, de Roo N, Jacobs DM, van Duynhoven JP, Vervoort J (2012) Structural elucidation and quantification of phenolic conjugates present in human urine after tea intake. Anal Chem 84(16):7263-7271.

Wang, S., Liu, G., Zhang W., Cai, N., Cheng C., Ji Y., Sun L., Zhan, J., Yuan, S., Efficient glycosylation of puerarin by an organic solvent-tolerant strain of Lysinibacillus fusiformis, Enzyme Microb. Technol. 57 (2014) 42-47).

Wang Y, Catana F, Yang Y, Roderick R, Van Breemen R (2002) Analysis of resveratrol in grape products, cranberry juice and wine using liquid chromatography-mass spectrometry. J Agric Food Chem 50:431-435.

Weymouth-Wilson AC (1997) The role of carbohydrates in biologically active natural products. Nat Prod Rep 14(2):99-110.

Xu G, Cai W, Gao W, Liu C (2016) A novel glucuronosyltransferase has an unprecedented ability to catalyse continuous two-step glucuronosylation of glycyrrhetinic acid to yield glycyrrhizin. New Phytol 212(1):123-135.

Yonekura K, Hanada K (2011) An evolutionary view of functional diversity in family 1 glycosyltransferases. Plant J 66(1):182-193.

Yu C, Shin YG, Chow A, Li Y, Kosmeder JW, Lee YS, Hirschelman WH, Pezzuto JM, Mehta RG, van Breemen RB (2002) Human, rat, and mouse metabolism of resveratrol. Pharm Res 19(12):1907-1914.

Yu D, Xu F, Valiente J, Wang S, Zhan J (2013a) An indigoidine biosynthetic gene cluster from Streptomyces chromofuscus ATCC 49982 contains an unusual IndB homologue. J Ind Microbiol Biot 40(1):159-168.

Yu D, Xu F, Zhang S, Shao L, Wang S, Zhan J (2013b) Characterization of a methyltransferase involved in herboxidiene biosynthesis. Bioorg Med Chem Lett 23(20):5667-5670.

Bowles D, Isayenkova J, Lim E-K, Poppenberger B (2005) Glycosyltransferases: managers of small molecules. Curr Opin Plant Biol 8(3):254-263.

Cassinelli G, Ballabio M, Grein A, Merli S, Rivola G, Arcamone F, Barbieri B, Bordoni T (1987) A new class of biosynthetic anthracyclines: anthracyclinone glucuronides. J Antibiot 40(7):1071-1074.

Gachon CM, Langlois-Meurinne M, Saindrenan P (2005) Plant secondary metabolism glycosyltransferases: the emerging functional analysis. Trends Plant Sci 10(11):542-549.

Hmidene AB, Hanaki M, Murakami K, Irie K, Isoda H, Shigemori H (2017) Inhibitory activities of antioxidant flavonoids from Tamarix gallica on amyloid aggregation related to Alzheimer's and type 2 diabetes diseases. Biol Pharm Bull 40(2):238-241.

Imai H, Kitagawa M, Ishihara K, Masuoka N, Shimoda K, Nakajima N, Hamada H (2012) Glycosylation of trans-resveratrol by plant-cultured cells. Biosci Biotech Bioch 76(8):1552-1554.

Jiao Z-Z, Yue S, Sun H-X, Jin T-Y, Wang H-N, Zhu R-X, Xiang L (2015) Indoline amide glucosides from Portulaca oleracea: isolation, structure, and DPPH radical scavenging activity, J Nat Prod 78:2588□2597.

Kren V, Martínková L (2001) Glycosides in medicine: "The role of glycosidic residue in biological activity". Curr Med Chem 8(11):1303-1328.

Mehnaz D, Abdulla K, Aiysha D, Zaheer A, Mukhtar S (2017) Actinomycetes: a source of industrially important enzymes. J Proteom Bioinform 10:12.

Nagashima S, Hirotani M, Yoshikawa T (2000) Purification and characterization of UDP-glucuronate: baicalein 7-O-glucuronosyltransferase from Scutellaria baicalensis Georgi. cell suspension cultures. Phytochemistry 53(5):533-538.

Nawani N, Aigle B, Mandal A, Bodas M, Ghorbel S, Prakash D (2013) Actinomycetes: Role in biotechnology and medicine. BioMed Res Int 2013: 687190.

Prakash D, Nawani N, Prakash M, Bodas M, Mandal A, Khetmalas M, Kapadnis B (2013) Actinomycetes: a repertory of green catalysts with a potential revenue resource. Biomed Res Int 2013:264020.

Stachulski AV, Harding JR, Lindon JC, Maggs JL, Park BK, Wilson ID (2006) Acyl glucuronides: biological activity, chemical reactivity, and chemical synthesis. J Med Chem 49(24):6931-6945.

Sauer S, Plauth A (2017) Health-beneficial nutraceuticals—myth or reality? Appl Microbiol Biotechnol 101(3):951-961.

Sawada Sy, Suzuki H, Ichimaida F, Yamaguchi M-a, Iwashita T, Fukui Y, Hemmi H, Nishino T, Nakayama T (2005) UDP-glucuronic acid: anthocyanin glucuronosyltransferase from red daisy (*Bellis perennis*) flowers: enzymology and phylogenetics of a novel glucuronosyltransferase involved in flower pigment biosynthesis. J Biol Chem 280(2):899-906.

(56) References Cited

PUBLICATIONS

Wang L-X, Heredia A, Song H, Zhang Z, Yu B, Davis C, Redfield R (2004) Resveratrol glucuronides as the metabolites of resveratrol in humans: characterization, synthesis, and anti-HIV activity. J Pharm Sci 93(10):2448-2457.

Wilkinson SM, Liew CW, Mackay JP, Salleh HM, Withers SG, McLeod MD (2008) *Escherichia coli* glucuronylsynthase: an engineered enzyme for the synthesis of β-glucuronides. Org Lett 10(8):1585-1588.

Wilkinson SM, Watson MA, Willis AC, McLeod MD (2011) Experimental and kinetic studies of the *Escherichia coli* glucuronylsynthase: An engineered enzyme for the synthesis of glucuronide conjugates. J Org Chem 76(7):1992-2000.

\* cited by examiner

PROCESS FOR PRODUCING A GLUCURONIDE AND GENETICALLY MODIFIED MICROORGANISMS USEFUL IN THIS PROCESS

CROSS-REFERENCE TO RELATED APPLICATIONS

This disclosure claims the benefit, including the filing date, of U.S. Provisional Patent No. 63/273,136, entitled "Process for Producing a Glucuronide and Genetically Modified Microorganisms Useful in this Process" which was filed on Oct. 28, 2021, the entire disclosure of which is hereby incorporated herein by this reference.

STATEMENT OF GOVERNMENT SUPPORT

This invention was made with government support under Grant No. CBET-2044558 and Grant No. CHE-1429195 awarded by the National Science Foundation. The government has certain rights in the invention.s

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 13,218 byte XML file named "SeqList" created on Aug. 25, 2022.

TECHNICAL FIELD

The present invention relates to in vitro and in vivo processes for producing a glucuronide; expression vectors, nucleic acids, polypeptides, and recombinant microbial cells useful in carrying out the process; and prodrugs produced by the process

BACKGROUND

Plant polyphenols are an important group of compounds with diverse chemical structures (Harborne and Baxter 1999; Tsao 2010). Stilbenoids and flavonoids are representative examples of polyphenols which are rich in commonly consumed fruits and vegetables, and both animal and human clinical studies showed their health-promoting effects and antioxidant characteristics (Rice-Evans 2001; Thilakarathna and Rupasinghe 2013). However, low water solubility and poor bioavailability often limit the beneficial effects of polyphenols. Structural modification is extensively attempted to improve the utility of these natural products. Introduction of polar groups such as sugar moieties into the structure is a widely used approach to improve the water solubility of bioactive molecules. Glycosyltransferases can be used as an effective tool to create glycosides from natural products. As such, discovery of novel and versatile glycosyltransferases is important for adding new enzymes into the biocatalytic toolbox.

Sugar moieties often play important roles in binding of drugs to biological targets. They may also be involved in other biochemical processes such as distribution, metabolism, and excretion properties of drugs, which can affect the efficacy of its oral administration (Thorson et al. 2004; Weymouth-Wilson 1997; Yu et al. 2002). Meanwhile, glycosylated compounds exhibit increased water-solubility, intestinal absorption, biological half-life, physicochemical stability, and bioavailability for medical and cosmetic applications while also reducing the toxicity compared to their aglycon forms (Bowles et al. 2005; Cai et al. 2013; Gachon et al. 2005; Imai et al. 2012; Kaminaga et al. 2003). Digitoxin, amphotericin, vancomycin, streptomycin, and daunomycin are some examples of the most biologically active natural products and commonly used therapeutics, with one or more sugar moieties (Pandey et al. 2014). Sugar moieties can also contribute to other biological properties of natural products. For instance, the glucuronic acid moieties of glycyrrhizin are essential for its sweet taste (Chung et al. 2020).

Glycosyltransferases are the enzymes responsible for transferring sugar moieties from sugar donors to acceptors to yield corresponding glycosides. Microorganisms are a rich source of both natural products and natural product biosynthetic enzymes. Some of these enzymes may be developed into useful biocatalysts for desired reactions. Actinomycetes, the most ubiquitous group of gram-positive filamentous bacteria, are well characterized for their metabolic versatility (Nawani et al. 2013; Prakash et al. 2013). For example, they can decompose organic matter (such as cellulose) which is important for the carbon cycle and maintaining the soil structure (Kim 2016; Priyadharsini and Dhanasekaran 2015). In addition, actinomycetes can also produce various commercial products, such as pharmaceuticals, antibiotics, antitumor agents, and nutraceuticals (Prakash et al. 2013; Remya and Vij ayakumar 2008). Furthermore, many actinomycete genera produce industrially important enzymes applied in biotechnological applications and biomedical fields, such as amylases, cellulases, chitinases, xylanases, and proteases (Mehnaz et al. 2017; Nawani et al. 2013).

Glucuronidation is one of the common glycosylation reactions in nature. Due to the polarity of the glucuronic acid moiety, glucuronides often show much better water solubility than their aglycons. Therefore, glucuronidation is a useful approach to create water-soluble glycosides of natural products. UDP-Glucuronyltransferases (UGTs) are the enzymes involved in glucuronidation, which are often observed in metabolism of xenobiotics and endogenous components (bilirubin, bile acids, and certain hormones) during phase II metabolism, which is the common detoxification pathway in the human body (de Wildt et al. 1999; Wilkinson et al. 2008). There are mainly two phases for drug metabolism, namely functionalization reactions and conjugation reactions. Glucuronidation is one of the phase II conjugation reactions. It was predicted that about 10% of the top 200 prescribed drugs recorded in USA are fully or partially metabolized by UGTs. UGTs transfer the glucuronic acid moiety from uridine 5'-diphosphoglucuronic acid (UDP-glucuronic acid) to various exogenous and endogenous compounds. They often work with cytochrome P450 enzymes (CYPs) to metabolize most hepatically cleared drugs.

UGTs have been commonly found in plants and animals. However, there are relatively few studies on microbial UGTs. Plant UGTs are usually involved in catalyzing the last step of plant secondary metabolism, specifically, the glucuronic acid group is transferred from the sugar donor to the phenolic hydroxyl group of the substrates, such as flavonoids. O-Glucuronidation makes secondary metabolites of plants possess better solubility and chemical stability, as well as lower toxicity for storage which is helpful for its accumulation in cells. O-Glucuronides are widely present in plants. They can not only resist the invasion of pathogenic bacteria, but also play an important role in the metabolic balance of endogenous hormones. Therefore, they are essential in regulating the physiological and ecological functions of plants (Li et al. 2001). O-Glucuronides of many drugs and their phase I metabolites are produced by human (or animal) UGTs, which can be prepared by UGT catalysis in animal tissues. Compared to plant UGTs, UGTs are more widely distributed in animal tissues, and their functions are similar to those of plant UGTs (Stachulski and Jenkins 1998). However, it is technically challenging and cost-ineffective to obtain UGTs from plants and animals for large scale preparation of desired glucuronides. No UGTs have been discovered from microorganisms to date, which has limited our understanding of this type of enzyme and their applications in industry.

Many fields such as drug development, sports drug testing, and the detection of agricultural residues often require the identification, quantification, and pharmacological evaluation of the glucuronidated metabolites (Wilkinson et al. 2011). However, chemical approaches like the Koenigs-Knorr reaction used for glucuronidation often suffer from poor yields and side reactions, as well as tedious protection-deprotection of the hydroxyl groups of sugar moieties (Engstrom et al. 2006; Stachulski et al. 2006). Enzymatic preparation of glucuronides represents a "green" alternative because of the selectivity, mild conditions and elimination of the need of toxic chemical reagents. Discovery of efficient and versatile UGTs is critical for the development of a feasible and viable production process of glucuronides.

SUMMARY

In our ongoing effort of discovering novel enzymes for natural product glycosylation, we found *Streptomyces chromofuscus* ATCC 49982 can convert resveratrol and several other natural products to corresponding glucuronides. We then analyzed the genome of this strain and discovered a putative UGT gene flanked by two UDP-glucuronic acid biosynthetic genes. The UGT gene was then cloned and heterologously expressed in *Escherichia coli* BL21(DE3). The enzyme was functionally characterized through in vitro reactions and its optimal reaction conditions were investigated. This enzyme is highly versatile and can convert a variety of substrates into monoglucuronides or diglucuronides. Therefore, this UGT represents a useful tool for the synthesis of glucuronidated metabolites. We also used the engineered *E. coli* strain to produce the two resveratrol glucuronides and the optimal bioconversion conditions were studied. This technology can be applied to a variety of molecules to yield corresponding glucuronides. Furthermore, a glucuronide was prepared from 2'-hydroxyflavone, which showed significantly improved water solubility and antioxidant activity. To our best knowledge, it is the first time that a highly versatile UGT was cloned and characterized from microorganisms, which lays the foundation for the microbial production of valuable glucuronides.

In certain aspects, the present invention relates to a process for producing a glucuronide comprising a glucuronic acid moiety bound to a phenolic hydroxyl group or a phenolic carboxyl group, the process comprising the steps of: (i) culturing in a medium a genetically modified microorganism capable of producing a glucuronide comprising a glucuronic acid moiety bound to a phenolic hydroxyl group or a phenolic carboxyl group, wherein the genetically modified microorganism compared to a non-modified control microorganism of the same strain has increased activity of a gene product of a UDP-glucuronyltransferase (UGT) with a SEQ ID NO: 7 or a polypeptide sequence which is at least 95% identical to SEQ ID NO: 7 and which has at least 80% of the enzymatic activity of the polypeptide according to SEQ ID NO: 7 under conditions allowing the microorganism to produce the glucuronide; and (ii) optionally recovering the glucuronide from the medium.

In one aspect, the genetically modified microorganism compared to a non-modified control microorganism of the same strain has increased activity of at least one gene product selected from the group consisting of: a UDP-glucose dehydrogenase with a SEQ ID NO: 6 or a polypeptide sequence which is at least 95% identical to SEQ ID NO: 6 and which has at least 80% of the enzymatic activity of the polypeptide according to SEQ ID NO: 6; and a UDP-glucose pyrophosphorylase with a SEQ ID NO: 8 or a polypeptide sequence which is at least 95% identical to SEQ ID NO: 8 and which has at least 80% of the enzymatic activity of the polypeptide according to SEQ ID NO: 8.

In another aspect, an increased activity of the respective gene product is achieved by introducing into the microorganism one or more copies of the respective gene product or a nucleotide sequence encoding the respective gene product.

In some aspects, the microorganism is selected from the group consisting of bacteria, yeast, filamentous fungi, and microalgae. In one aspect, the microorganism is selected from the group consisting of *Aspergillus, Trichoderma, Saccharomyces, Pichia, Phaffia, Candida, Hansenula, Salmonella, Bacillus, Acinectorhacter, Zymomonas, Agrobacterium, Erythrobacter, Chloroborium, Chlorella, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Methanomonas, Synechococcus, Anabeana, Thiobacillus, Methanobacterium, Klebsiella*, and *Myxococcus*.

In other aspects, the medium comprises a phenolic compound. In one embodiment, the phenolic compound is selected from the group consisting of resveratrol, quercetin, ferulic acid, vanillic acid, curcumin, vanillin, chrysin, zearalenone, apigenin, doxorubicin, etoposide, morphine, ezetimibe, 2'-hydroxyflavone, and combinations thereof. In another embodiment, the phenolic compound is at a concentration of between about 0.25 mM and about 0.75 mM.

In yet other aspects, the medium is maintained: a) at a pH of between about 5.5 and about 7.5; b) at a temperature of between about 35° C. and about 45° C.; and/or c) for a duration of between about 2.5 hour and 3.5 hours.

In certain aspects, the present invention relates to an expression vector comprising a gene encoding a UGT operably linked to a promoter suitable to drive expression of the UGT in microbial cells, wherein the UGT gene has a nucleotide sequence having at least 90% sequence identity to the nucleotide sequence shown in SEQ ID NO: 4, and wherein the UGT has an amino acid sequence having at least 90% sequence identity to the amino acid sequence shown in SEQ ID NO: 7.

In other aspects, the present invention provides a nucleic acid comprising a gene encoding a UGT, wherein the UGT gene has a nucleotide sequence having at least 90% sequence identity to the nucleotide sequence shown in SEQ ID NO: 4, and wherein the UGT has an amino acid sequence having at least 90% sequence identity to the amino acid sequence shown in SEQ ID NO: 7.

In yet other aspects, the present invention provides a polypeptide comprising an amino acid sequence having at least 90% sequence identity to the amino acid sequence shown in SEQ ID NO: 7.

In certain aspects, the present invention relates to a microbial cell comprising an expression vector, a nucleic acid, or a polypeptide as described herein, wherein the microbial cell is optionally a bacterial, yeast, filamentous fungi, or microalgal cell.

In certain aspects, the present disclosure concerns microbial cells comprising at least one of (a) expression vector comprising a gene encoding a UGT operably linked to a promoter suitable to drive expression of the UGT in microbial cells, wherein the UGT gene has a nucleotide sequence having at least 90% sequence identity to the nucleotide sequence shown in SEQ ID NO: 4, and wherein the UGT has an amino acid sequence having at least 90% sequence identity to the amino acid sequence shown in SEQ ID NO: 7; (b) nucleic acid comprising a gene encoding a UGT, wherein the UGT gene has a nucleotide sequence having at least 90% sequence identity to the nucleotide sequence shown in SEQ ID NO: 4, and wherein the UGT has an amino acid sequence having at least 90% sequence identity to the amino acid sequence shown in SEQ ID NO: 7, and (c) polypeptide comprising an amino acid sequence having at least 90% sequence identity to the amino acid sequence shown in SEQ ID NO: 7; wherein the microbial cell is optionally a bacterial, yeast, filamentous fungi, or microalgal cell.

In one aspect, the present invention provides an in vitro process for producing a glucuronide comprising a glucuronic acid moiety bound to a phenolic hydroxyl group or a phenolic carboxyl group, the process comprising the steps of: (i) purifying or partially purifying a gene product of a UDP-glucuronyltransferase (UGT) with a SEQ ID NO: 7 or a polypeptide sequence which is at least 95% identical to SEQ ID NO: 7 and which has at least 80% of the enzymatic activity of the polypeptide according to SEQ ID NO: 7; (ii) combining a phenolic compound and UDP-glucuronic acid with the UGT under conditions suitable to allow the production of the glucuronide; and (iii) optionally recovering the glucuronide.

In certain aspects, conditions suitable to allow the production of the glucuronide comprise: a) a pH of between about 6.5 and about 8.5; b) a temperature of between about 25° C. and about 35° C.; and/or c) with $Ca^{2+}$, $Mg^{2+}$, and/or $Mn^{2+}$ at a concentration of between about 5 mM and 15 mM.

In other aspects, the present invention provides a prodrug comprising a phenolic compound with a glucuronic acid moiety bound to a phenolic hydroxyl group or a phenolic carboxyl group, wherein the prodrug is produced with a process disclosed herein.

In one aspect, the prodrug is produced with a phenolic compound. Examples of phenolic compounds include resveratrol, quercetin, ferulic acid, vanillic acid, curcumin, vanillin, chrysin, zearalenone, apigenin, doxorubicin, etoposide, morphine, ezetimibe, and combinations thereof.

In other aspects, glucuronidation of the phenolic compound results in a monoglucuronide, a diglucuronide, or a combination thereof. In yet another aspect, the prodrug is cleaved by a β-glucuronidase after administration to a subject in need thereof.

BRIEF DESCRIPTION OF THE DRAWINGS

FIG. 1A depicts an HPLC analysis (300 nm) of biotransformation of resveratrol by five actinomycete strains. (i) resveratrol+YM medium; (ii) resveratrol+S. roseum No. 79089; (iii) resveratrol+S. reseiscleroticus ATCC 53903; (iv) resveratrol+A. hibisca P157-2; (v) resveratrol+Streptomyces sp. FERM BP-2474; (vi) resveratrol+S. chromofuscus ATCC 49982. FIG. 1B depicts a UV spectra comparison of the substrate and product 1. FIG. 1C depicts a UV spectra comparison of the substrate and product 2. FIG. 1D depicts an ESI-MS (−) spectrum of product 1. FIG. 1E depicts an ESI-MS (−) spectrum of product 2.

FIG. 3A depicts glucuronidation of quercetin (350 nm); FIG. 3B depicts glucuronidation of ferulic acid (300 nm); FIG. 3C depicts glucuronidation of vanillic acid (300 nm). (i) substrate+YM medium; (ii) substrate+S. chromofuscus ATCC 49982.

FIG. 4A depicts the organization of the gca gene cluster. FIG. 4B depicts proposed pathways for UDP-glucuronic acid biosynthesis and glucuronidation of resveratrol.

FIG. 5A depicts N-His6-tagged GcaC (~43.4 kDa) purified from cell lysate analyzed by SDS-PAGE. FIG. 5B depicts an HPLC analysis (300 nm) of the in vitro reaction of GcaC with resveratrol. (i) resveratrol+reaction buffer without GcaC; (ii) resveratrol+GcaC. FIG. 5C depicts an ESI-MS (−) spectrum of in vitro product 1. FIG. 5D depicts an ESI-MS (−) spectrum of in vitro product 2.

FIG. 6A depicts glucuronidation of quercetin (350 nm). FIG. 6B depicts glucuronidation of ferulic acid (300 nm). FIG. 6C depicts glucuronidation of vanillic acid (300 nm). FIG. 6D depicts glucuronidation of curcumin (420 nm). FIG. 6E depicts glucuronidation of vanillin (300 nm). FIG. 6F depicts glucuronidation of chrysin (350 nm). FIG. 6G depicts glucuronidation of zearalenone (250 nm). FIG. 6H depicts glucuronidation of apigenin (350 nm). For each figure: (i) substrate incubated with the reaction buffer without GcaC; (ii) substrate incubated with the reaction buffer with GcaC.

FIG. 7A depicts the effect of reaction temperature on the GcaC glucuronidation activity. FIG. 7B depicts the effect of reaction pH on the GcaC glucuronidation activity. FIG. 7C depicts the effect of metal ions on the GcaC glucuronidation activity. Data are presented as the mean±SD from three independent experiments.

FIG. 8A depicts an HPLC analysis (300 nm) of resveratrol glucuronidation by GcaC in E. coli BL21(DE3). (i) Commercial standard of resveratrol; (ii) resveratrol+E. coli BL21 (DE3)/pET28a; (iii) resveratrol+E. coli BL21(DE3)/pJR36. FIG. 8B depicts the effect of cell density on resveratrol glucuronidation. FIG. 8C depicts the effect of reaction pH on resveratrol glucuronidation by E. coli BL21(DE3)/pJR36. FIG. 8D depicts the effect of temperature on resveratrol glucuronidation by E. coli BL21(DE3)/pJR36. FIG. 8E depicts the effect of reaction time on resveratrol glucuronidation by E. coli BL21(DE3)/pJR36. FIG. 8F depicts the effect of substrate concentration on resveratrol glucuronidation by *E. coli* BL21(DE3)/pJR36. Data are presented as the mean±SD from three independent experiments.

DETAILED DESCRIPTION

Figure 1A:
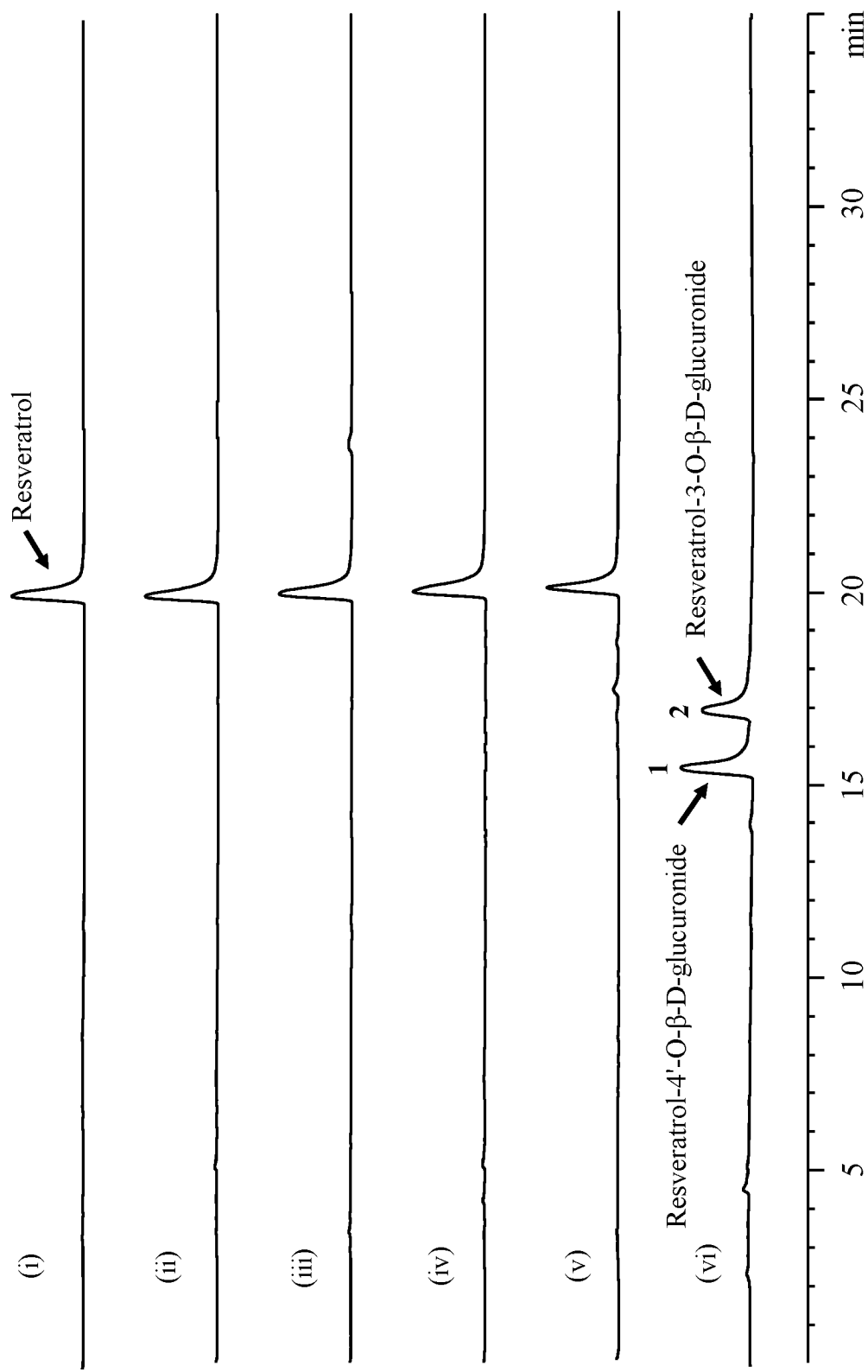
FIGS. 1A-1E depict screening of five actinomycete strains for the ability to biotransform resveratrol.

As used herein and in the appended claims, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, a "biologically pure" strain is intended to mean the strain separated from materials with which it is normally associated in nature. A strain associated with other strains, or with compounds or materials that it is not normally found with in nature, is still defined as "biologically pure." A monoculture of a particular strain is, of course, "biologically pure." In different embodiments, a "biologically pure" culture has been purified at least 2× or 5× or 10× or 50× or 100× or 1000× or higher (to the extent considered feasible by a skilled person in the art) from the material with which it is normally associated in nature. As a non-limiting example, if a culture is normally associated with soil, the organism can be biologically pure to an extent that its concentration in a given quantity of purified or partially purified material with which it is normally associated (e.g. soil) is at least 2× or 5× or 10× or 50× or 100× or 1000× or higher (to the extent considered feasible by a skilled person in the art) that in the original unpurified material.

An "expression vector" as used herein is a DNA molecule used to transfer and express foreign genetic material in a cell. Such vectors include a promoter sequence operably linked to the gene encoding the protein to be expressed. "Promoter" means a minimal DNA sequence sufficient to direct transcription of a DNA sequence to which it is operably linked. "Promoter" is also meant to encompass those promoter elements sufficient for promoter-dependent gene expression controllable for cell type specific expression; such elements may be located in the 5' or 3' regions of the native gene.

An expression vector may also include a termination codon and expression enhancers. Any suitable vectors, promoters, enhancers, and termination codons may be used to express the enzymes according to the invention. Suitable vectors include plasmids, binary vectors, phages, phagemids, viral vectors and artificial chromosomes (e.g., yeast artificial chromosomes or bacterial artificial chromosomes).

Generally speaking, those skilled in the art are well able to construct vectors and design protocols for recombinant gene expression. Suitable vectors can be chosen or constructed, containing, in addition to the elements of the invention described above, appropriate regulatory sequences, including promoter sequences, terminator fragments, polyadenylation sequences, marker genes and other sequences as appropriate. Molecular biology techniques suitable for the expression of polypeptides in cells are well known in the art. For further details see, for example, Molecular Cloning: a Laboratory Manual: 2nd edition, Sambrook et al, 1989, Cold Spring Harbor Laboratory Press or Current Protocols in Molecular Biology, Second Edition, Ausubel et al. eds., John Wiley & Sons, (1995, and periodic supplements).

The term "operably linked" used herein includes the situation where a selected gene and promoter are covalently linked in such a way as to place the expression of the gene (i.e., polypeptide coding) under the influence or control of the promoter. Thus, a promoter is operably linked to a gene if the promoter is capable of effecting transcription of the gene into RNA in a cell. Where appropriate, the resulting RNA transcript may then be translated into a desired protein or polypeptide. The promoter is suitable to effect expression of the operably linked gene in a microbial cell.

The invention also provides a nucleic acid comprising a gene encoding a UGT. The UGT gene present in the nucleic acid can have the requisite features and sequence identity as described herein in relation to the expression vectors.

Alignment and calculation of percentage amino acid or nucleotide sequence identity can be achieved in various ways know to a person of skill in the art, for example, using publicly available computer software such as ClustalW 1.82, T-coffee or Megalign (DNASTAR) software. When using such software, the default parameters, e.g., for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=-1, Protein/DNA GAPDIST=4.

The percentage identity can then be calculated from the multiple alignment as (N/T)*100, where N is the number of positions at which the two sequences share an identical residue, and T is the total number of positions compared. Alternatively, percentage identity can be calculated as (N/S)*100 where S is the length of the shorter sequence being compared. The amino acid/polypeptide/nucleic acid sequences may be synthesized de novo or may be native amino acid/polypeptide/nucleic acid sequence, or a derivative thereof.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example, small non-polar, hydrophobic amino acids include glycine, alanine, leucine, isoleucine, valine, proline, and methionine. Large non-polar, hydrophobic amino acids include phenylalanine, tryptophan, and tyrosine. The polar neutral amino acids include serine, threonine, cysteine, asparagine, and glutamine. The positively charged (basic) amino acids include lysine, arginine, and histidine. The negatively charged (acidic) amino acids include aspartic acid and glutamic acid. As described herein, suitable variants of the UGT can contain amino acid substitutions at any amino acid.

In some aspects, the present invention relates to a polypeptide that functions as a UGT. A preferred polypeptide sequence for a UGT is disclosed in SEQ ID NO: 7; as well as polypeptide sequences which are at least 75%, 80%, 85%, 90%, 95%, 96%, 97%, 98%, and 99% identical to SEQ ID NO: 7 and which have at least 50%, preferred 80%, 90%, 100% and most preferred more than 100%, more than 120%, more than 150% of the enzymatic activity of the polypeptide according to SEQ ID NO: 7.

In other aspects, the present invention relates to nucleic acid comprising a gene encoding a UGT. A preferred nucleotide sequence for a UGT is disclosed in SEQ ID NO: 4; as well as nucleotide sequences which are at least 75%, 80%, 85%, 90%, 95%, 96%, 97%, 98%, and 99% identical to SEQ ID NO: 4.

A genetically modified microorganism having a modification which confers an increased activity of a gene products means a microorganism which is treated by endogenous or exogenous factors in order to increase at the end the activity of the corresponding gene product.

This is possible at different levels, e.g., at the level of the DNA, at the level of the RNA and at the level of the protein. At the level of the DNA an increased activity of the respective gene product can be achieved by introducing into the microorganism genes in one or multiple copies for the respective gene product or one or multiple copies of mutated genes coding for gene products with a higher enzymatic activity or for more stable gene products enzymes, which will not be degraded in the microorganism as rapidly as the unmutated gene products. These additional copies of the respective genes can be introduced into the genome of the microorganism or in an extrachromosomal way. Also, they can be introduced in a permanent or a transient way.

At the level of RNA, it is possible to increase the gene expression by using genetic elements such as effective promoters, enhancers, terminators, and other regulatory elements which allow a higher or a permanent gene expression of the respective gene.

Another possibility is to stabilize the RNA transcripts made of the respective gene in order to effect a higher number of transcripts available for translation per time unit.

Another possibility is to deregulate a strongly regulated gene expression, e.g., feedback inhibition, by altering the regulatory elements on the polynucleotide site, such as operators, or on the polypeptide site such as repressors. By this means a highly regulated gene expression ("bottleneck") can be deregulated in order to allow a higher activity of the gene product. Another possibility to interfere with at the protein side is the codon usage of the gene. A codon usage optimized for the respective host organism allows a high translation rate resulting in an increase of active protein.

The possibilities to intervene at can be combined in various ways, e.g., multiple copies of a codon optimized gene can be expressed under a strong promotor.

In the context of this invention the term "genetically modified microorganism" should be understood in a broad sense; not only "genes" and "genetic elements" such as promotors, are encompassed by the term "genetically modified microorganism", but also a derepression of gene regulation by using molecules binding tightly to a repressor and thus inactivating the repressor is understood as a genetically modified microorganism according to this invention. In the context of this invention also combinations of gene products are used.

The recovering of the glucuronide from the fermentation product can be performed by a number of routine techniques known in biotechnology such as precipitation and centrifugation.

Glycosylation is an effective way to increase the polarity of natural products. UDP-Glucuronyltransferases (UGTs) are commonly observed and extensively studied in phase II drug metabolism. However, UGTs in microorganisms are not well studied, which hampered the utilization of this type of enzyme in microbial glucuronidation of natural products. Screening of five actinomycete strains showed that *Streptomyces chromofuscus* ATCC 49982 can convert diverse plant polyphenols into more polar products, which were characterized as various glucuronides based on their spectral data. Analysis of the genome of this strain revealed a putative glucuronidation gene cluster that contains a UGT gene (gcaC) and two UDP-glucuronic acid biosynthetic genes (gcaB and gcaD). The gcaC gene was cloned and heterologously expressed in *Escherichia coli*. Incubation of the purified enzyme with resveratrol and UDP-glucuronic acid led to the production of resveratrol-4'-O-β-D-glucuronide and resveratrol-3-O-β-D-glucuronide, allowing GcaC to be characterized as a flexible UGT. The optimal in vitro reaction pH and temperature for GcaC are 7.5 and 30° C., respectively. Its activity can be stimulated by $Ca^{2+}$, $Mg^{2+}$ and $Mn^{2+}$, whereas $Z_n^{2+}$, $Cu^{2+}$ and $Fe^{2+}$ showed inhibitory effects. Furthermore, GcaC has a broad substrate specificity, which can glucuronidate various substrates besides resveratrol, including quercetin, ferulic acid, vanillic acid, curcumin, vanillin, chrysin, zearalenone, and apigenin. The titers of resveratrol-4'-O-β-D-glucuronide and resveratrol-3-O-β-D-glucuronide in *E. coli*/GcaC were 78.381±0.366 mg/L and 14.991±0.248 mg/L from 114.125 mg/L resveratrol within 3 hours. In some aspects, the present invention provides an effective way to produce glucuronides of resveratrol and other health-benefitting natural products. Non-limiting examples of health-benefitting natural products that can act as substrates for GcaC are presented in Table 1.

TABLE 1

Examples of plant phenolic compounds that act as substrates for GcaC.

| Common name | Structure | IUPAC name |
| --- | --- | --- |
| p-Hydroxybenzoic acid | 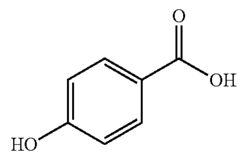 | 4-Hydroxybenzoic acid |
| p-Coumaric acid | 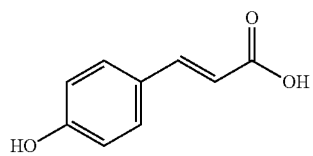 [SMILES: O=C(O)/C=C/c1ccc(O)cc1] | 3-(4-Hydroxyphenyl)-2-propenoic acid |
| Protocatechuic acid | 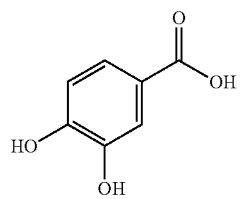 [SMILES: O=C(O)c1ccc(O)c(O)c1] | 3,4-Dihydroxybenzoic acid |
| Caffeic acid | 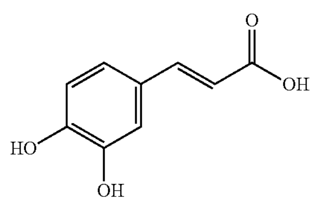 [SMILES: O=C(O)/C=C/c1ccc(O)c(O)c1] | 3-(3,4-Dihydroxyphenyl)-2-propenoic acid |
| Gallic acid | 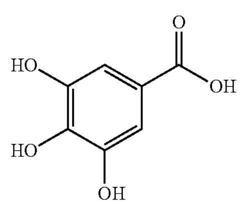 [SMILES: O=C(O)c1cc(O)c(O)c(O)c1] | 3,4,5-Trihydroxybenzoic acid |
| Vanillic acid | 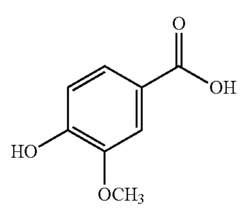 [SMILES: COc1cc(C(=O)O)ccc1O] | 4-Hydroxy-3-methoxybenzoic acid |
| Isovanillic acid | 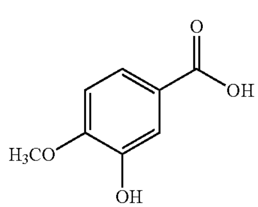 [SMILES: COc1ccc(C(=O)O)cc1O] | 3-Hydroxy-4-methoxybenzoic acid |

TABLE 1-continued

Examples of plant phenolic compounds that act as substrates for GcaC.

| Common name | Structure | IUPAC name |
| --- | --- | --- |
| Syringic acid | 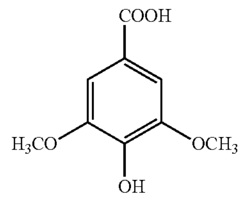 [SMILES: COc1cc(C(=O)O)cc(OC)c1O] | 4-Hydroxy-3,5-dimethoxybenzoic acid |
| Ferulic acid | 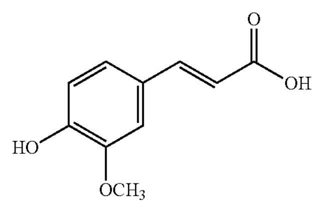 [SMILES: COc1cc(/C=C/C(=O)O)ccc1O] | 3-(4-Hydroxy-3-methoxy-phenyl)prop-2-enoic acid |
| Chlorogenic acid (3-Caffeoylquinic acid) | 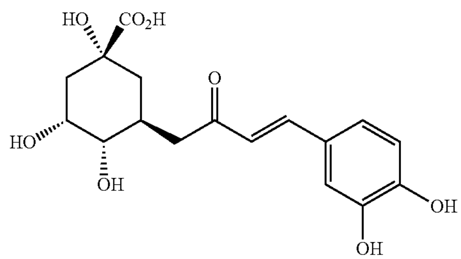 [SMILES: O=C(/C=C/c1ccc(O)c(O)c1)C[C@@H]1C[C@](O)(C(=O)O)C[C@@H](O)[C@H]1O] | 3-{[(2E)-3-(3,4-Dihydroxyphenyl)prop-2-enoyl]oxy}-1,4,5-trihydroxycyclohexanecarboxylic acid |
| Di-caffeoylquinic acid (Cynarine) | 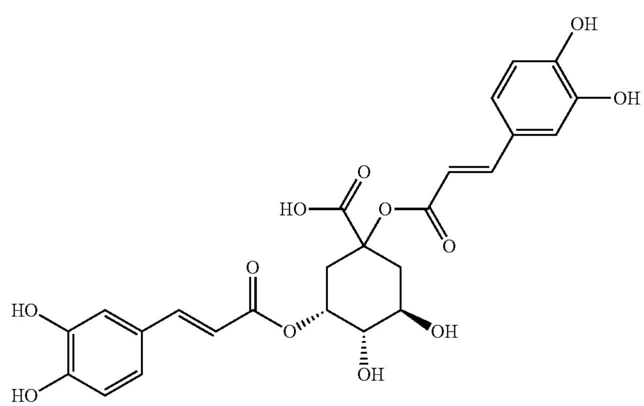 [SMILES: O=C(/C=C/c1ccc(O)c(O)c1)O[C@@H]1CC(OC(=O)/C=C/c2ccc(O)c(O)c2)(C(=O)O)C[C@@H](O)[C@@H]1O] | (1R,3R,4S,5R)-1,3-Bis[[(E)-3-(3,4-dihydroxyphenyl)prop-2-enoyl]oxy]-4,5-dihydroxycyclohexane-1-carboxylic acid |

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1. Materials and Methods

General Equipment and Experimental Materials

Agilent 1200 HPLC instrument with an Agilent Eclipse Plus-$C_{18}$ column (5 μm, 250 mm×4.6 mm) was used to analyze and purify the products. The samples were eluted with methanol-water (5:95 to 95:5 over 30 minutes, v/v, containing 0.1% formic acid) at a flow rate of 1 mL/min. ESI-MS spectra were obtained on an Agilent 6130 single quadrupole LC-MS in the negative mode. All purified compounds were dissolved in in deuterated dimethyl sulfoxide (DMSO-$d_6$) to collect the NMR spectra on a Bruker Avance III HD Ascend-500 NMR instrument (500 MHz for $^1$H NMR and 125 MHz for $^{13}$C NMR) located in the Department of Chemistry and Biochemistry, Utah State University. The chemical shift (δ) values are given in parts per million (ppm). The coupling constants values) are reported in hertz (Hz). Low-resolution ESI-MS spectra were obtained on an Agilent 6130 LC-MS to confirm the molecular weights of glucuronides.

Phusion High-Fidelity DNA polymerase, restriction enzymes and T4 DNA ligase were purchased from New England Biolabs. PCR reactions were conducted with an Arktik Thermal Cycler (Thermo Scientific). Genomic DNA extraction was performed using the Quick-DNA™ Fungal/

Bacteria DNA Miniprep Kit (Zymo Research, USA). Plasmid extraction was performed using the Thermo Scientific GeneJET Plasmid Miniprep Kit (Thermo Scientific). Primers were ordered from Thermo Scientific and dissolved in Tris-EDTA (TE) buffer to the concentration of 100 ng/mL. Standard compounds like resveratrol, quercetin, curcumin, vanillic acid, ferulic acid, vanillin, chrysin, zearalenone, and apigeninwere purchased from Sigma-Aldrich (USA). HisPur™ Ni-NTA resin, Luria-Bertani (LB) medium, yeast and malt extracts were purchased from Fisher Scientific (Rockford, IL, USA). Bradford assay solution was purchased from TCI America (Portland, OR, USA). Solvents and all other chemicals were purchased from Fisher Scientific. Milli-Q water was used throughout this study.

Strains, Vectors, Media, and Culture Conditions

Streptosporangium roseum No. 79089 (NRRL 2505) was provided by the ARS Culture Collection (NRRL) of the United States Department of Agriculture. *Streptomyces reseiscleroticus* ATCC 53903, Actinomadura hibisca P157-2 (ATCC 53557), and *S. chromofuscus* ATCC 49982 were obtained from the American Type Culture Collection (ATCC). *Streptomyces* sp. FERM BP-2474 was acquired from Patent and Bio-Resource Center, National Institute of Advanced Industrial Science and Technology, Japan.

*E. coli* XL1-Blue and BL21(DE3) were both purchased from Agilent. *E. coli* XL1-Blue was used for routine gene cloning and plasmid propagation. *E. coli* BL21(DE3) was used for protein expression and in vivo biotransformation. The pJET1.2 (Thermo Fisher Scientific, USA) and pET28a (+) (Millipore Sigma, USA) vectors were used, respectively, to clone and express UGT. The *E. coli* strains were routinely grown at 37° C. on LB agar plates or in liquid LB medium (Fisher Scientific, USA). When necessary, carbenicillin (50 μg/mL) and kanamycin (50 μg/mL) were supplemented into the culture media for selecting correct clones. *S. chromofuscus* ATCC 49982 was grown on YM plate (4 g/L yeast extract, 10 g/L malt extract, 4 g/L glucose, and 20 g/L agar) or in YM broth (4 g/L yeast extract, 10 g/L malt extract, and 4 g/L glucose) at 28° C. Recombinant UGT was expressed in *E. coli* BL21(DE3) at 28° C. Isopropyl-1-thio-β-D-galactopyranoside (IPTG) (Gold Biotechnology, USA) was used at 200 μM to induce protein expression in *E. coli* BL21 (DE3).

Screening of Glucuronidating Actinomycete Strains

To test the ability of actinomyces to glucuronidate resveratrol, we screened five strains, namely, *S. roseum* No. 79089, *S. reseiscleroticus* ATCC 53903, *A. hibisca* ATCC 53557, *Streptomyces* sp. FERM BP-2474, and *S. chromofuscus* ATCC 49982. These bacteria were grown in 50 mL of YM medium in a rotary shaker at 250 rpm and 28° C. for 3 days.

Resveratrol (4 mg) was dissolved in dimethyl sulfoxide (DMSO) and added into each culture. The cultures were incubated under the same conditions for an additional 4 days. After that, 1 mL of fermentation broth was sampled and centrifuged at 15,000×g for 10 min. The supernatant was analyzed by HPLC on an Agilent Eclipse Plus $C_{18}$ column (5 μm, 250 mm×4.6 mm) at 300 nm. A gradient of methanol-water (5-95%, v/v) containing 0.1% (v/v) formic acid was programmed over 35 min at a flow rate of 1 mL/min.

In order to check whether *S. chromofuscus* ATCC 49982 can glucuronidate other substrates, quercetin, ferulic acid, and vanillic acid were incubated with the culture of this strain in a similar way. The supernatant was analyzed by HPLC on an Agilent Eclipse Plus $C_{18}$ column (5 μm, 250 mm×4.6 mm) at 350 nm (quercetin) or 300 nm (ferulic acid and vanillic acid) using the same HPLC conditions for resveratrol.

Extraction and Purification of Compounds

To isolate the biotransformation products of resveratrol for structure elucidation, *S. chromofuscus* ATCC 49982 was cultivated in 1-L Erlenmeyer flasks, containing 250 mL of YM medium, to biotransform 20 mg of resveratrol. After 4 days, the fermentation broth was centrifuged at 4,000×g for 10 min. After water in the supernatant was evaporated, the residue was dissolved in 2 mL of methanol. The sample was subjected to Sephadex LH-20 column chromatography, and eluted with methanol-water (1:1, v/v). The products-containing fraction was further separated by reverse phase HPLC, and eluted with methanol-water (10-50%, 0-17 min; 50-95, 17-22 min) containing 0.1% formic acid (v/v) to yield 1 (3.6 mg) and 2 (2.8 mg). Products 1 and 2 were also used to prepare a standard curve to quantify the formation of these products in the in vitro and in vivo reactions.

A similar procedure was used to isolate the biotransformation products of quercetin, ferulic acid and vanillic acid for structure elucidation except the HPLC methods for final compound purification. The gradient elution method with methanol-water (20-40%, 0-2 min; 40%, 2-15 min; 40-95%, 15-20 min) was used to yield product 3 (7.4 mg) and 4 (5.8 mg). The gradient elution method with methanol-water (5-60%, 0-15 min; 60-95%, 15-16 min; 95%, 16-18 min) was used to yield product 5 (4.8 mg), 6 (3.0 mg) and 7 (1.2 mg). All purified products were subjected to NMR analysis. The purified products were dissolved in DMSO-$d_6$ and their chemical structures were characterized by NMR spectra.

Resveratrol-4'-O-β-D-glucuronide (1): $^1$H NMR (500 MHz, DMSO-$d_6$): δ 7.52 (d, J=8.8 Hz, 2H, H-2' and H-6'), 7.01 (d, J=8.8 Hz, 2H, H-3' and H-5'), 6.96 (d, J=17.2 Hz, 2H, H-7, 8), 6.41 (d, J=2.1 Hz, 2H, H-2 and H-6), 6.14 (t, J=2.1 Hz, 1H, H-4), 5.07 (d, J=7.5 Hz, 1H, H-1"), 3.93 (m, 1H, H-5"), 3.41-3.28 (overlapped, 3H, H-2', H-3', and H-4'). $^{13}$C NMR (125 MHz, DMSO-$d_6$): δ 170.5 (C-6"), 159.0 (C-3 and C-5), 156.9 (C-4'), 139.4 (C-1), 131.6 (C-1'), 128.1 (C-2' and C-6'), 127.8 (C-8), 127.7 (C-7), 116.8 (C-3' and C-5'), 104.9 (C-2 and C-6), 102.5 (C-4), 100.3 (C-1"), 76.2 (C-3"), 75.9 (C-5"), 73.4 (C-2"), 71.8 (C-4").

Resveratrol-3-O-β-D-glucuronide (2): $^1$H NMR (500 MHz, DMSO-$d_6$): δ 7.40 (d, J=8.6 Hz, 2H, H-2' and H-6'), 7.01 (d, J=16.2 Hz, 1H, H-7), 6.87 (d, J=16.4 Hz, 1H, H-8), 6.76 (d, J=8.6 Hz, 2H, H-3' and H-5'), 6.66 (s, 1H, H-2), 6.62 (s, 1H, H-6), 6.32 (t, J=2.1 Hz, 1H, H-4), 4.99 (d, J=7.7 Hz, 1H, H-1"), 3.89 (m, 1H, H-5"), 3.40-3.27 (overlapped, 3H, H-2', H-3', and H-4'). $^{13}$C NMR (125 MHz, DMSO-$d_6$): δ 170.1 (C-6"), 158.4 (C-3 and C-5), 157.9 (C-4'), 139.4 (C-1), 132.2 (C-1'), 128.6 (C-8), 127.9 (C-2' and C-6'), 126.4 (C-7), 115.5 (C-3' and C-5'), 104.8 (C-2 and C-6), 102.1 (C-4), 100.5 (C-1"), 77.2 (C-3"), 75.8 (C-5"), 72.9 (C-2"), 71.4 (C-4").

Quercetin-7-O-β-D-glucuronide (3): $^1$H NMR (500 MHz, DMSO-$d_6$): δ 7.72 (d, J=2.2 Hz, 1H, H-2'), 7.56 (dd, J=8.5, 2.2 Hz, 1H, H-6'), 6.91 (d, J=8.5 Hz, 1H, H-5'), 6.80 (d, J=2.0 Hz, 1H, H-8), 6.44 (d, J=2.0 Hz, 1H, H-6), 5.29 (d, J=7.3 Hz, 1H, H-1"), 4.06 (d, J=9.6 Hz, 1H, H-5"), 3.41 (m, 1H, H-4"), 3.35-3.31 (overlapped, 2H, H-2" and H-3"). $^{13}$C NMR (125 MHz, DMSO-$d_6$): δ 176.0 (C-4), 170.1 (C-6"), 162.2 (C-7), 160.4 (C-5), 155.7 (C-9), 147.9 (C-4'), 147.6 (C-2), 145.1 (C-3'), 136.1 (C-3), 121.8 (C-1'), 120.0 (C-6'), 115.6 (C-5'), 115.4 (C-2'), 104.8 (C-10), 99.1 (C-1"), 98.6 (C-6), 94.1 (C-8), 75.6 (C-3"), 75.4 (C-5"), 72.8 (C-2"), 71.2 (C-4").

Quercetin-3-O-β-D-glucuronide (4): $^1$H NMR (500 MHz, DMSO-d$_6$): δ 7.61 (dd, J=8.5, 2.2 Hz, 1H, H-6'), 7.53 (d, J=2.2 Hz, 1H, H-2'), 6.84 (d, J=8.5 Hz, 1H, H-5'), 6.41 (d, J=2.0 Hz, 1H, H-8), 6.21 (d, J=2.0 Hz, 1H, H-6), 5.50 (d, J=7.5 Hz, 1H, H-1''), 3.57 (d, J=9.7 Hz, 1H, H-5''), 3.39-3.25 (overlapped, 3H, H-2', H-3', and H-4'). $^{13}$C NMR (125 MHz, DMSO-d$_6$): δ 177.1 (C-4), 169.7 (C-6''), 164.2 (C-7), 161.2 (C-5), 156.2 (C-2 and C-9), 148.6 (C-4'), 144.9 (C-3'), 133.0 (C-3), 121.7 (C-1'), 120.8 (C-6'), 116.0 (C-2'), 115.2 (C-5'), 104.8 (C-10), 101.0 (C-1''), 98.8 (C-6), 93.6 (C-8), 76.0 (C-5''), 75.8 (C-2''), 73.8 (C-4''), 71.3 (C-3'').

Ferulic acid-4-O-β-D-glucuronide (5): $^1$H NMR (500 MHz, DMSO-d$_6$): δ 7.52 (d, J=15.9 Hz, 1H, H-7), 7.34 (d, J=1.3 Hz, 1H, H-2), 7.19 (dd, J=8.5, 1.3 Hz, 1H, H-6), 7.09 (d, J=8.5 Hz, 1H, H-5), 6.47 (d, J=15.9 Hz, 1H, H-8), 5.13 (d, J=7.1 Hz, 1H, H-1'), 3.86 (s, 3H, OCH$_3$), 3.86 (d, J=9.5 Hz, 1H, H-5'), 3.37 (m, 1H, H-4'), 3.32-3.29 (overlapped, 2H, H-2' and H-3'). $^{13}$C NMR (125 MHz, DMSO-d$_6$): δ 170.2 (C-6'), 167.8 (C-9), 149.2 (C-3), 147.8 (C-4), 143.9 (C-7), 128.4 (C-1), 122.1 (C-6), 117.4 (C-8), 114.9 (C-5), 111.3 (C-2), 99.2 (C-1'), 76.1 (C-3'), 75.3 (C-5'), 72.9 (C-2'), 71.4 (C-4'), 55.7 (OCH$_3$).

Vanillic acid-4-O-β-D-glucuronide (6): $^1$H NMR (500 MHz, DMSO-d$_6$): δ 7.51 (dd, J=8.5, 1.6 Hz, 1H, H-6), 7.48 (d, J=1.6 Hz, 1H, H-2), 7.15 (d, J=8.5 Hz, 1H, H-5), 5.11 (d, J=6.1 Hz, 1H, H-1'), 3.81 (s, 3H, OCH$_3$), 3.71 (m, 1H, H-5'), 3.32-3.26 (overlapped, H-2', H-3', and H-4'). $^{13}$C NMR (125 MHz, DMSO-d$_6$): δ 170.8 (C-6'), 167.0 (C-7), 150.0 (C-4), 148.5 (C-3), 124.4 (C-1), 122.7 (C-6), 114.3 (C-5), 112.7 (C-2), 99.2 (C-1'), 76.4 (C-3'), 74.7 (C-5'), 72.9 (C-2'), 71.6 (C-4'), 55.6 (OCH$_3$).

Vanillic acid-7-O-β-D-glucuronide (7): $^1$H NMR (500 MHz, DMSO-d$_6$): δ 7.54 (dd, J=8.3, 2.0 Hz, 1H, H-6), 7.49 (d, J=2.0 Hz, 1H, H-2), 6.89 (d, J=8.3 Hz, 1H, H-5), 5.54 (d, J=7.5 Hz, 1H, H-1'), 3.83 (s, 3H, OCH$_3$), 3.82 (m, 1H, H-5'), 3.40-3.35 (overlapped, 3H, H-2', H-3', and H-4'). $^{13}$C NMR (125 MHz, DMSO-d$_6$): δ 170.4 (C-6'), 164.4 (C-7), 152.1 (C-4), 147.4 (C-3), 124.1 (C-6), 119.7 (C-1), 115.2 (C-5), 112.9 (C-2), 94.6 (C-1'), 75.9 (C-3'), 75.7 (C-5'), 72.7 (C-2'), 71.6 (C-4'), 55.7 (OCH$_3$).

Genome Analysis and Amplification of the Putative UGT Gene from *S. chromofuscus* ATCC 49982

The genomic DNA was extracted from *S. chromofuscus* ATCC 49982 using the Quick-DNA™ Fungal/Bacterial Microprep Kit (Zymo Research, USA) by following the manufacturer's standard procedure. The 454 next-generation sequencing system and Rapid Annotation using Subsystem Technology (RAST) were used respectively to sequence and annotate the genomic DNA of *S. chromofuscus*. The glucuronidation (gca) gene cluster was deposited into GenBank under the accession number MZ666424. The detailed functions of each gene in the gene cluster was predicted based on BLAST analysis of the corresponding amino acid sequences.

Plasmids were extracted from *E. coli* via the GeneJET Plasmid Miniprep Kit (Thermo Fisher Scientific). Primers were synthesized by Thermo Scientific (5'-AATTGTTTAAACCATATGCGAGTACTGTTCACCAC-3' (SEQ ID NO: 1) and 5'-AATTGCTAGCAAGCTTTCAGACGATCTTCTGCAGGTC-3' (SEQ ID NO: 2)). The primers (1 μM), genomic DNA (0.2 μL), dNTP mix (200 μM), 5× buffer (4 μL), DMSO (0.4 μL), Phusion High-Fidelity DNA Polymerase (0.2 μL at 2 U/μL) and nuclease-free water were mixed to 20 μL for amplification of the UGT (gcaC) gene (1,209 bp). The PCR program began with an initial denaturation at 95° C. for 5 min, and then 20 cycles of touchdown program (95° C. for 30 s, annealing at 70° C. for 40 s, decreasing 0.5° C. per cycle, and extension at 72° C. for 100 s), followed by 20 cycles of regular program (95° C. for 30 s, annealing at 60° C. for 40 s, and extension at 72° C. for 100 s), and finally, 68° C. for 15 min of extension.

Construction of Cloning and Expression Plasmids

After purification with a GeneJET Gel Extraction Kit, the target PCR product was ligated into the pJET1.2 cloning vector to yield pJR34 (pJET1.2-gcaC). After the pJR34 plasmid was confirmed by digestion check and sequencing using the Sanger method, the gene was excised from pJR34 and introduced to the pET28a expression vector between the NdeI and HindIII restriction sites to yield expression plasmid pJR36 (pET28a-gcaC). The ligation product was transferred into *E. coli* XL1-Blue competent cells through chemical transformation, and the transformants were selected on LB agar with 50 μg/mL kanamycin. The correct plasmids were confirmed by digestion check with NdeI and HindIII.

Heterologous Expression of GcaC and In Vivo Biotransformation of Resveratrol in *E. coli* BL21(DE3)

The expression plasmid pJR36 was transferred into *E. coli* BL21(DE3) through chemical transformation. The correct transformant of *E. coli* BL21(DE3)/pJR36 was picked from LB agar into 5 mL of LB medium supplemented with kanamycin (50 μg/mL), incubating at 37° C. with shaking (250 rpm) for about 12 hours. Then 500 μL of the seed culture was inoculated into 50 mL of LB broth with kanamycin (50 μg/mL) with shaking at 250 rpm and 37° C. When the OD$_{600}$ reached between 0.4 and 0.6, protein expression was induced with 200 μM IPTG, and the culture was maintained at 28° C. for an additional 16 hours with shaking at 250 rpm. After protein expression, 0.35 mM resveratrol and 0.11 M glucose were added as the substrates. The culture was incubated under the same conditions for an additional 48 hours. After fermentation, 1 mL of the culture was sampled and centrifuged at 15,000×g for 10 min. 100 μL of the supernatant was subjected to analysis on an Agilent 1200 HPLC (at 300 nm) coupled with an Agilent 6130 single quadrupole mass spectrometer.

Purification of Recombinant GcaC from *E. coli* BL21(DE3)/pJR36

The *E. coli* BL21(DE3)/pJR36 cells were centrifuged at 3,600×g and 4° C. for 10 min. The harvested cells were resuspended in lysis buffer that consisted of 20 mM Tris-HCl buffer (pH 7.9), 0.5 M NaCl and 1 mM dithiothreitol (DTT). Subsequently, the cells were disrupted by ultrasonication (Misonix Sonicator 3000, Misonix Inc., USA) on ice (20 seconds on, 40 seconds off, and in total 15 min). The cell lysate was centrifuged at 15,000×g and 4° C. for 10 min and the supernatant was analyzed by sodium dodecyl sulfate-polyacrylamide gel electrophoresis (SDS-PAGE) as soluble fraction. A premixed protein marker (EZ-Run™ Pre-Stained Rec Protein Ladder, molecular range: 11-170 kDa, Fisher BioReagents) was used for SDS-PAGE analysis as the reference. After electrophoresis, the gel was stained with 0.1% Coomassie Brilliant Blue R250, followed by destaining in 20% (v/v) acetic acid-water.

The supernatant of the cell lysate was loaded onto a HisPur™ Ni-NTA affinity column (Thermo Scientific, Rockford, USA) to purify the enzymes based on the manufacturer's protocol. After eluting the column with cold (4° C.) washing buffers (50 mM Tris-HCl, 2 mM EDTA, pH 7.9) containing 0, 10 mM and 25 mM imidazole, the recombinant UDPGT was finally eluted with elution buffer (50 mM Tris-HCl, 2 mM EDTA, pH 7.9) containing 250 mM imidazole. The purified His6-tagged protein was concentrated and desalted with buffer A (50 mM Tris-HCl, 2 mM EDTA, pH 7.9) to 1 mL, using the 30 K Macrosep Advance Centrifugal Device (Pall Corporation, New York, USA). This purified GcaC enzyme was stored in 50% (v/v) glycerol at −20° C. The protein concentration was determined using the Bradford assay. All protein purification steps were carried out at 4° C.

Functional Characterization of GcaC Through In Vitro Enzymatic Reactions

We characterized the function of GcaC by reacting the enzyme with the substrate resveratrol. Enzymatic assays were conducted in a 100-μL reaction system, which included 20 mM Tris-HCl (pH 8.0), 2.2 mM substrate, 1 mM $MgCl_2$, 2 mM sugar donor (UDP-glucuronic acid), and 23.7 μg purified recombinant GcaC protein. The mixtures were thoroughly mixed and incubated at 30° C. for 6 hours, and then 200 μL of HPLC-grade methanol was added to terminate the reaction. The reaction mixtures were centrifuged at 13,000×g for 10 min, and supernatants were collected to analyze the products by LC-MS. Compounds were eluted with a gradient of methanol-water containing 0.1% formic acid (0-30 min, 5:95-95:5, v/v), programming over 30 min at a flow rate of 1 mL/min with detection at 300 nm. Agilent 6130 single quadruple mass spectrometer was used to collect the ESI-MS spectrum.

The substrate specificity of GcaC was investigated using additional sugar-acceptor substrates, including curcumin, quercetin, ferulic acid, vanillic acid, vanillin, chrysin, apigenin, and zearalenone. In terms of sugar-donor substrates, another structurally similar sugar-donor substrate UDP-glucose was also reacted with resveratrol, besides UDP-glucuronic acid. Reaction products were analyzed by LC-MS after centrifugation.

Determination of the Optimal In Vitro Reaction Conditions

Purified resveratrol glucuronides were used to establish standard curves for quantifying product formation. The effects of reaction temperature, pH, and metal ions on the catalytic activity of GcaC were examined. To determine the optimum temperature, the reaction mixtures with resveratrol as the substrate were incubated at different temperatures (20, 25, 30, 35, 40, 45, and 50° C.) for 6 hours. Glucuronidation reactions were conducted in a 100-μL reaction system consisting of reaction buffer 20 mM Tris-HCl (pH 8.0), 23.7 μg of purified GcaC, 2 mM UDP-glucuronic acid, 1 mM $MgCl_2$ and 1.0 mM resveratrol. Reactions were terminated by adding 200 μL of methanol followed by centrifugation at 13,000×g for 10 min. The supernatants were sampled and analyzed by HPLC. In order to find out the optimum pH, GcaC was reacted with resveratrol at 30° C. in 200 mM phosphate buffer with different pH values (pH 4.5, 5.5, 6.0, 6.5, 7.0, 7.5, 8.0, 8.5, and 9.0). The conversion rate of resveratrol was quantified by HPLC. Control reaction was conducted under the same conditions, but without GcaC. Different metal ions such as $CaCl_2$, $CuCl_2$, $FeSO_4$, $MgCl_2$, $MnCl_2$, and $ZnCl_2$ were also tested. Control reaction was performed under the same conditions without adding these metal ions. The experiments were carried out with individually divalent metal ion at the final concentration of 10 mM, and UDP-glucuronic acid and resveratrol were used as sugar donor and sugar acceptor, respectively. All reactions were performed in triplicate and conversion rates were expressed as the mean±standard deviation.

Whole-Cell Bioconversion of Resveratrol Into Resveratrol Glucuronides by *E. coli* BL21(DE3)/p1R36

*E. coli* BL21(DE3)/pJR16 was grown and induced as described above. The cells were collected by centrifugation for whole-cell bioconversion after IPTG induction at 28° C. for 16 hours. Phosphate buffer was used to re-suspend the cells, and cell density was determined using a UV-Vis spectrophotometer (Thermo Scientific, Rockford, USA) by recording the $OD_{600}$ value. In order to determine the whole-cell bioconversion conditions, different pH values (pH 4.5, 5.5, 6.0, 6.5, 7.0, 7.5, and 8.5), temperatures (25, 30, 35, 40, and 45° C.), cell densities ($OD_{600}$ 2.5, 5, 7.5, 10, 12.5, and 15), reaction times (1, 2, 3, 4, and 5 h) and substrate concentrations (0.25, 0.5, 1.0, 1.5, 2.0 and 2.5 mM) were investigated. Product formation was quantified by HPLC. Finally, the whole-cell biotransformation experiment was performed in a 1-L reaction system under the optimal conditions. The reaction consisted of *E. coli* BL21(DE3)/pJR36 cells ($OD_{600}$ 10.0) and 0.5 mM resveratrol, and the bioconversion process was performed at 40° C., pH 6.5, and 250 rpm for 3 hours.

Figure 1B:
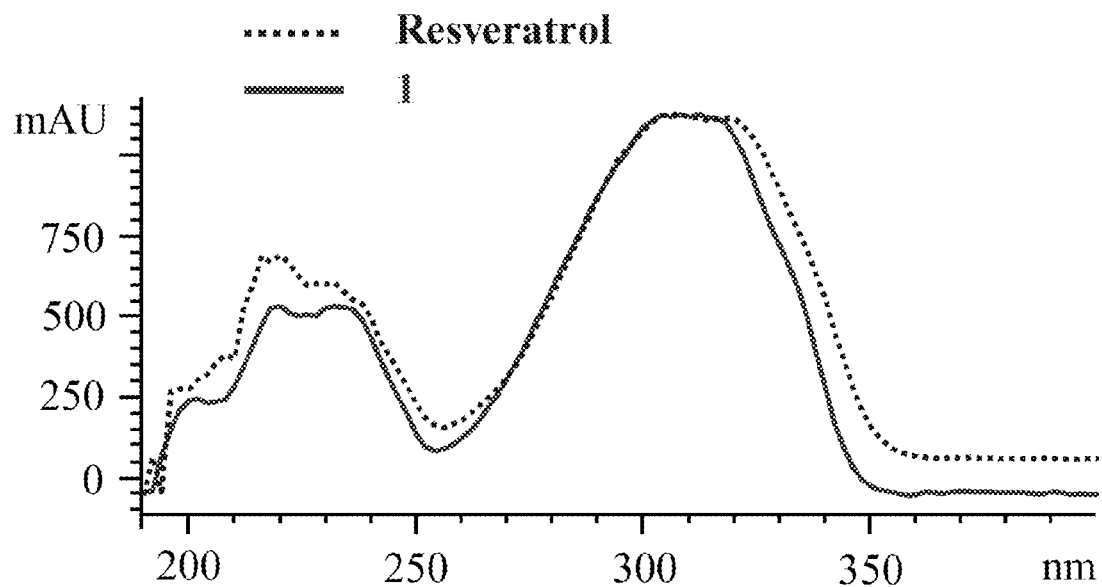
Figure 1C:
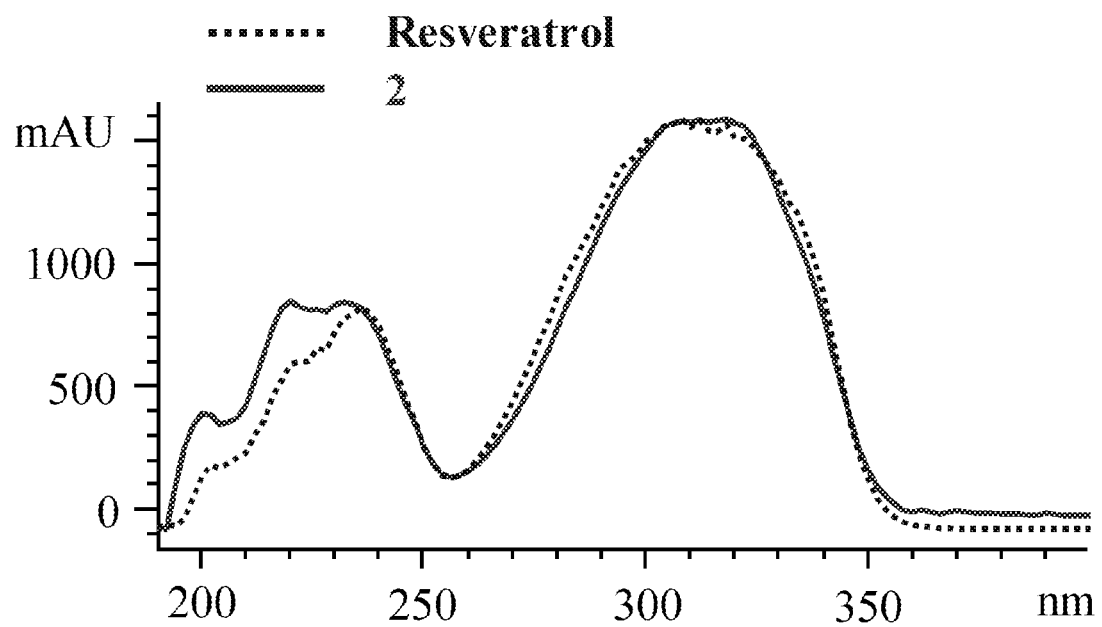

Example 2. Screening of Different Actinomycete Strains for the Ability to Glycosylate Resveratrol Actinomycetes are known to produce a variety of bioactive natural products and contain abundant biosynthetic enzymes. We hypothesized that some of these strains may have versatile UGTs that can introduce the glucuronic acid moiety to plant polyphenols such as resveratrol. To this end, resveratrol was incubated with five different strains, including *S. roseum* No. 79089, *S. reseiscleroticus* ATCC 53903, *A. hibisca* P157-2, *Streptomyces* sp. FERM BP-2474, and *S. chromofuscus* ATCC 49982. HPLC analysis revealed that two more polar metabolites, at 15.5 min for product 1 and 17.0 min for product 2 respectively, were synthesized from resveratrol by *S. chromofuscus* ATCC 49982 in 4 days (FIG. 1A). The UV absorption patterns of the products were both similar to that of resveratrol, suggesting that these two polar products are derivatives of the substrate (FIGS. 1B and 1C). However, no products were detected in the other four strains.

Example 3. Characterization of the Two Biotransformed Products of Resveratrol by *S. chromofuscus* ATCC 49982

Figure 1D:
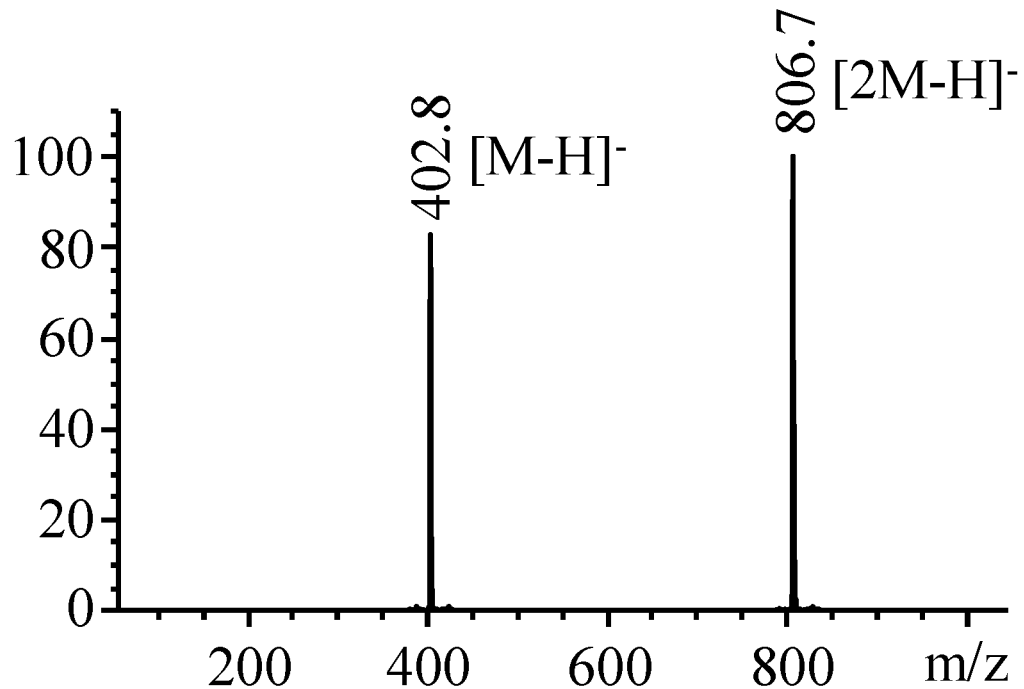
Figure 1E:
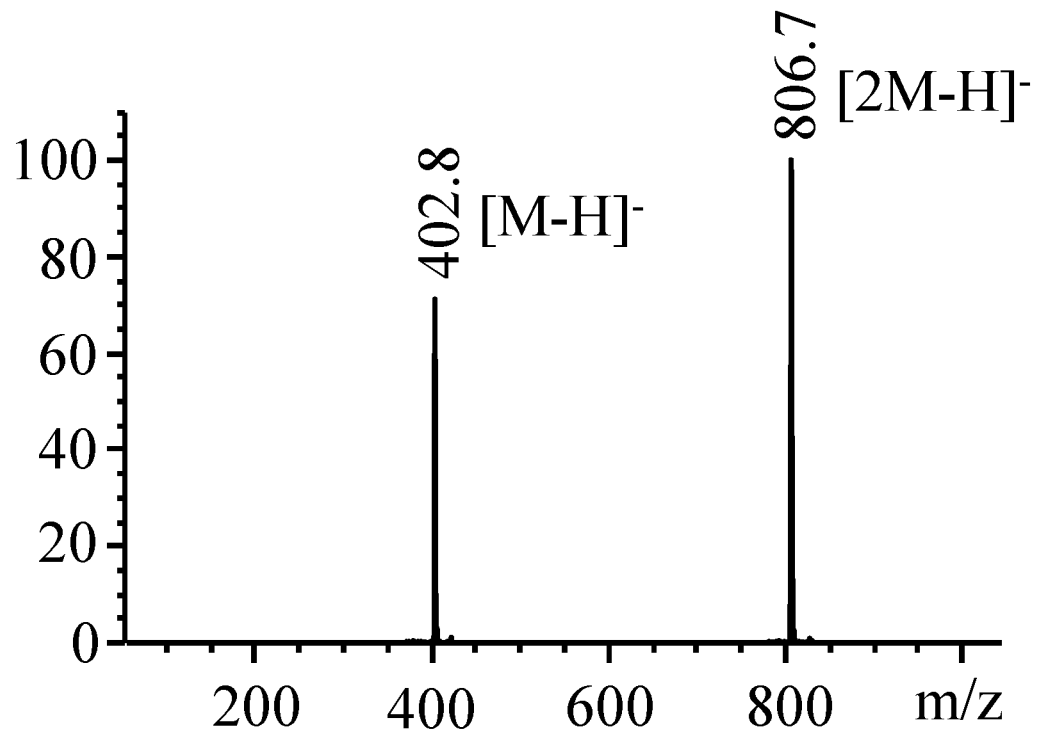

ESI-MS spectra of both 1 (FIG. 1D) and 2 (FIG. 1E) showed the same corresponding quasimolecular ions $[M-H]^-$ at m/z 402.8 and $[2M-H]^-$ at m/z 806.7, respectively. Therefore, products 1 and 2 have the same molecular weight of 404, which is 176 mass units larger than the substrate resveratrol, suggesting that a glucuronic acid moiety was added to different hydroxyl groups of resveratrol.

Figure 2:
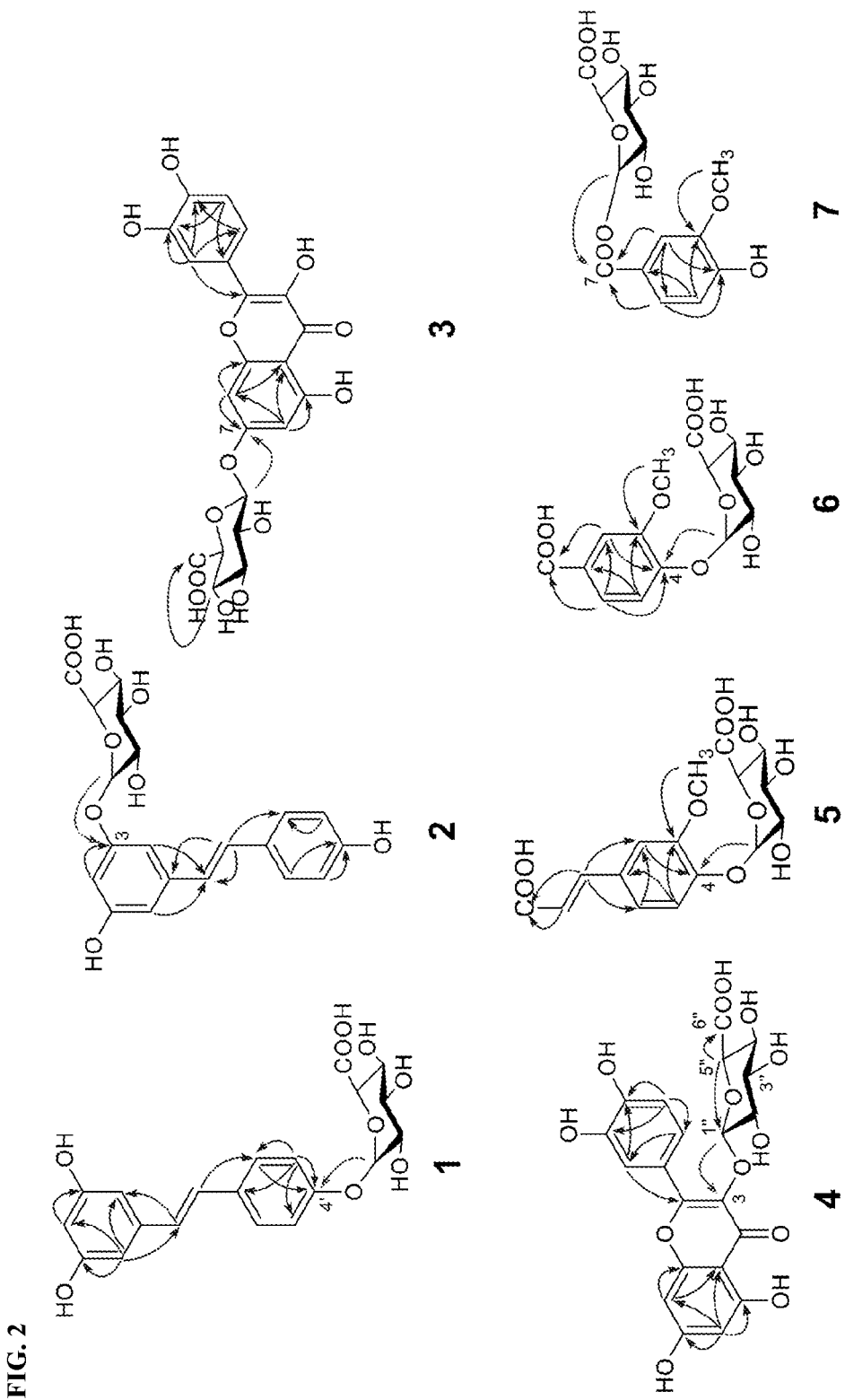
FIG. 2 depicts key HMBC correlations of compounds 1-7.

In order to elucidate the chemical structure, two purified products 1 and 2 were subjected to NMR analysis. The $^{13}C$ NMR spectra of 1 and 2 both revealed 20 carbon signals. In addition to the 14 signals belonging to resveratrol, six additional carbon signals at $\delta_C$ 170.5, 100.3, 76.2, 75.9, 73.4, and 71.8 for 1 and $\delta_C$ 170.1, 100.5, 77.2, 75.8, 72.9, and 71.4 for 2 were found in the spectra, further suggesting that a sugar moiety was added to resveratrol at one of its hydroxyl groups. Unlike glucose and other common sugars, this sugar moiety has a carbon signal at around $\delta_C$ 170, indicating the presence of a carboxyl group. Both the $^1H$ and $^{13}C$ signals of this sugar moiety supported the presence of a glucuronic acid moiety. As shown in the $^1H$ NMR spectra, the anomeric proton signals at $\delta_H$ 5.07 (d, J=7.5 Hz), and 4.99 (d, J=7.7 Hz) of 1 and 2, respectively, indicated the β-configuration of these two compounds for the glucuronic acid moiety. HMBC spectrum of 1 revealed the correlation of H-1" at $\delta_H$ 5.07 to C-4' at $\delta_C$ 156.9 (FIG. 2), which confirmed that 1 has a glucuronic acid moiety at C-4'. Similarly, H-1" at $\delta_H$ 4.99 of 2 had HMBC correlation to C-3 at $\delta_C$ 158.4, indicating that the glucuronic acid moiety was introduced at C-3 (FIG. 2).

Therefore, products 1 and 2 were characterized as resveratrol-4'-O-β-D-glucuronide and resveratrol-3-O-β-D-glucuronide, respectively. The NMR data of 1 and 2 are consistent with those reported in literature (Wang et al. 2004).

Example 4. Characterization of the Biotransformed Products of Quercetin, Ferulic Acid and Vanillic Acid by *S. chromofuscus* ATCC 49982

To check whether *S. chromofuscus* can also glucuronidate other natural products, quercetin, ferulic acid and vanillic acid were incubated with *S. chromofuscus* respectively. We found that all these three substrates can be glucuronidated into one or two glucuronides (FIG. 3).

When quercetin was used as substrate, HPLC analysis (FIG. 3A) showed that two polar products at 18.0 and 19.2 min, respectively, were formed from quercetin. Two products showed the similar UV spectra to the substrate. ESI-MS spectra of both 3 and 4 showed the corresponding quasi-molecular ion [M-H]⁻ at m/z 476.9 and 476.6, respectively. Therefore, products 3 and 4 have the same molecular weight of 478, which is 176 mass units larger than the substrate quercetin, indicating that a glucuronic acid moiety was added to different hydroxyl groups of quercetin.

Figures 3A, 3B:
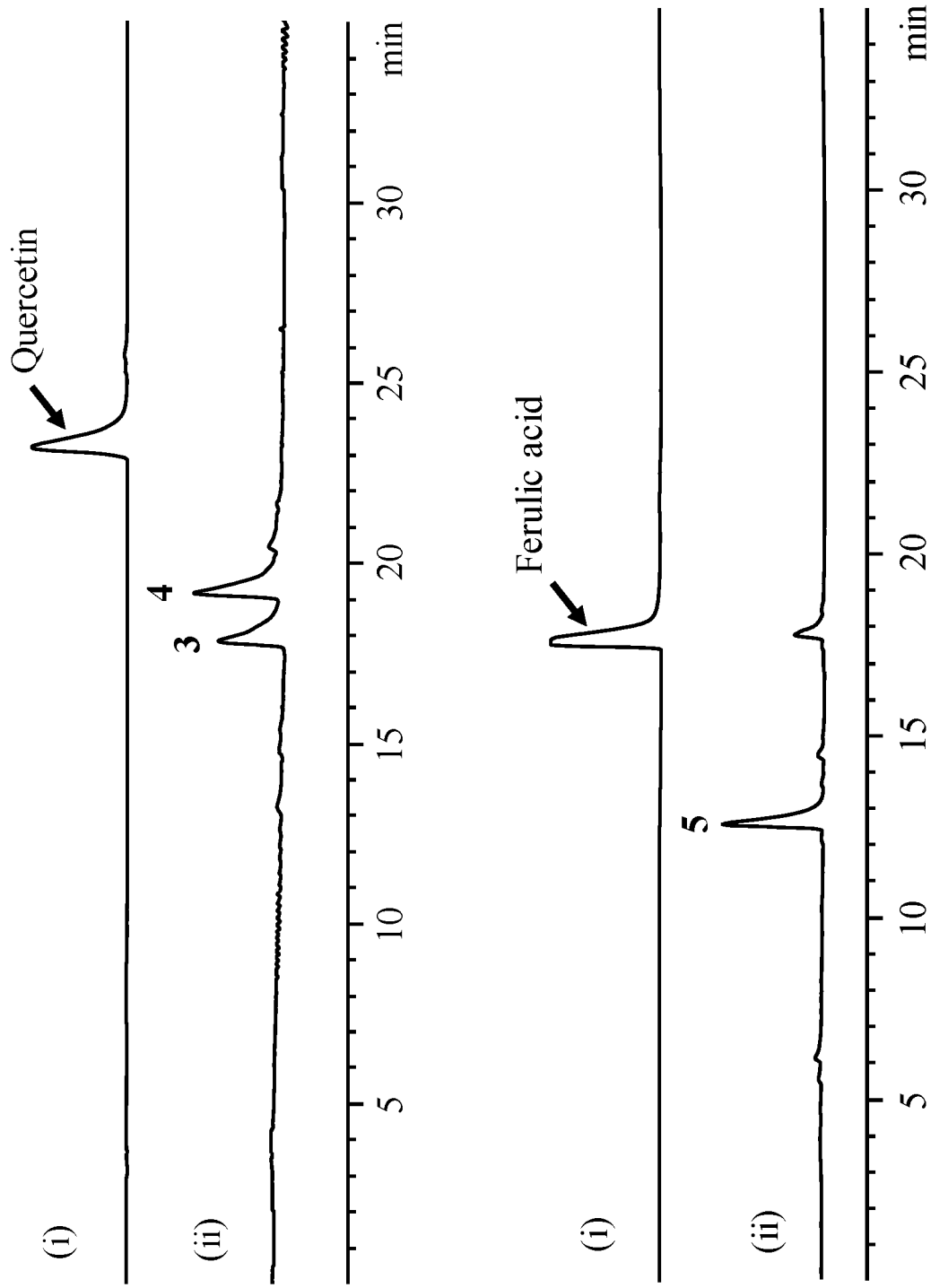
FIGS. 3A-3C depict an HPLC analysis of glucuronidation of different substrates by S. chromofuscus ATCC 49982.
Figure 3C:
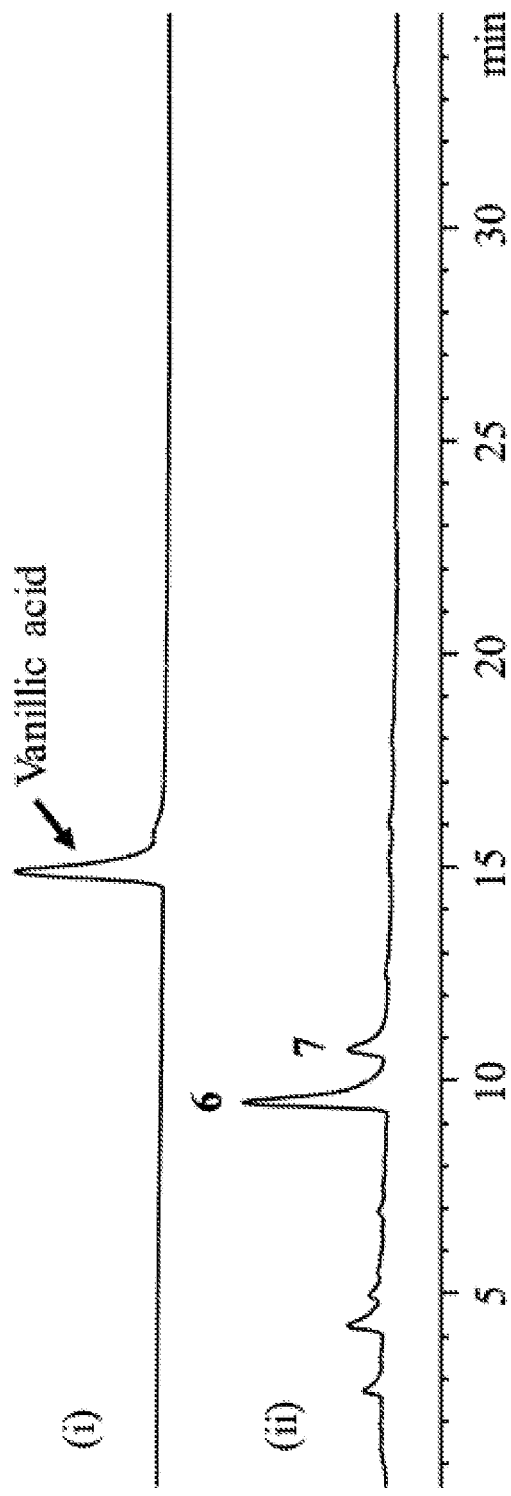

When the ferulic acid was used as the substrate, a polar product 5 at 12.8 min was detected by HPLC (FIG. 3B). Two more polar products 6 and 7 appeared at 9.7 and 10.8 min when vanillic acid was incubated with *S. chromofuscus* ATCC 49982 (FIG. 3C). These products showed the similar UV spectra to the corresponding substrates. The ESI-MS spectra of 5-7 showed a [M-H]⁻ ion peak at m/z 368.9, 342.9, and 342.9, respectively, indicating that their molecular weights are 370, 344 and 344 Da, which are consistent with the addition of a glucuronic acid moiety to the substrates ferulic acid and vanillic acid. Therefore, *S. chromofuscus* was found to be able to glucuronidate various phenolic natural products.

The NMR spectra of products 3-7 were collected. The $^{13}$C NMR spectra of compounds 3 and 4 both showed 21 carbon signals. In addition to the signals from quercetin, six additional carbon signals at $\delta_C$ 170.1, 99.1, 75.6, 75.4, 72.8, and 71.2 for 3 and $\delta_C$ 169.7, 101.0, 76.0, 75.8, 73.8, and 71.3 for 4 were found in the spectra. These signals were similar to those from the glucuronic acid moiety of 1 and 2, thus suggesting that a glucuronic acid moiety was added to one of the hydroxyl groups in quercetin. The anomeric proton signals at $\delta_H$ 5.29 (d, J=7.3 Hz), and 5.50 (d, J=7.5 Hz) of 3 and 4 in the $^1$H NMR spectra, respectively, indicated the β-configuration of the sugar moiety in these two compounds. HMBC spectrum of 3 revealed the correlation of H-1" at $\delta_H$ 5.29 to C-7 at $\delta_C$ 162.2 (FIG. 2), which confirmed that 3 has a glucuronic acid moiety at C-7. Similarly, H-1" of 4 at $\delta_H$ 5.50 had HMBC correlation to C-3 at $\delta_C$ 133.0, indicating that the glucuronic acid moiety was introduced at C-3 (FIG. 2). Therefore, products 3 and 4 were characterized as quercetin-7-O-β-D-glucuronide and quercetin-3-O-β-D-glucuronide, respectively. The NMR data of 3 and 4 are consistent with those reported in literature (Marvalin and Azerad 2011a).

The $^{13}$C NMR spectrum of compounds 5 revealed 16 carbon signals. Compared to the substrate ferulic acid, there were six additional carbon signals at $\delta_C$ 170.2, 99.2, 76.1, 75.3, 72.9, and 71.4, further suggesting that a glucuronic acid moiety was added to ferulic acid. As shown in the $^1$H NMR spectrum, the anomeric proton signal of 5 at $\delta_H$ δ 5.13 (d, J=7.1 Hz) indicated the β-configuration of the glucuronic acid moiety. HMBC spectrum of 5 revealed the correlation of H-1" ($\delta_H$ 5.13, d, J=7.1 Hz) to C-4 at $\delta_C$ 147.8 (FIG. 2), which confirmed that the position of glucuronic acid moiety is at C-4 of 5. Therefore, 5 was characterized as ferulic acid-4-O-β-D-glucuronide. The NMR data were assigned based on the 1D and 2D NMR spectra for the first time.

The $^{13}$C NMR spectra of both 6 sand 7 showed 14 carbon signals. In addition to the eight carbon signals from vanillic acid, six additional carbon signals at $\delta_C$ 170.8, 99.2, 76.4, 74.7, 72.9, and 71.6 were observed for 6 and $\delta_C$ 170.4, 94.6, 75.9, 75.7, 72.3, and 71.6 for 7, indicating that a glucuronic acid moiety was added to vanillic acid at different positions to yield the two products. In the $^1$H NMR spectra, the anomeric proton signals of 6 and 7 at $\delta_H$ 5.11 (d, J=6.1 Hz) and 5.54 (d, J=7.5 Hz), respectively, indicated the β-configuration of the glucuronic acid moiety in these compounds. HMBC spectrum of 6 revealed the correlation of H-1" at $\delta_H$ 5.11 to C-4 at $\delta_C$ 150.0 (FIG. 2), which confirmed that 6 has a glucuronic acid moiety at C-4. Similarly, H-1" of 7 at $\delta_H$ 5.54 had HMBC correlation to C-7 at $\delta_C$ 164.4, indicating that the glucuronic acid moiety was introduced at C-7 (FIG. 2). Therefore, 6 and 7 were characterized as vanillic acid-4-O-β-D-glucuronide and vanillic acid-7-O-β-D-glucuronide, respectively. The NMR data of compound 6 is consistent with those reported in literature (Almeida et al. 2017) and the NMR data of compound 7 were assigned based on the 1D and 2D NMR spectra for the first time.

Example 5. Discovery of a Putative Glucuronidation Gene Cluster from *S. chromofuscus* ATCC 49982

Figure 4A:
FIGS. 4A and 4B depict a putative glucuronidation (gca) gene cluster discovered in S. chromofuscus ATCC 49982.
Figure 4B:
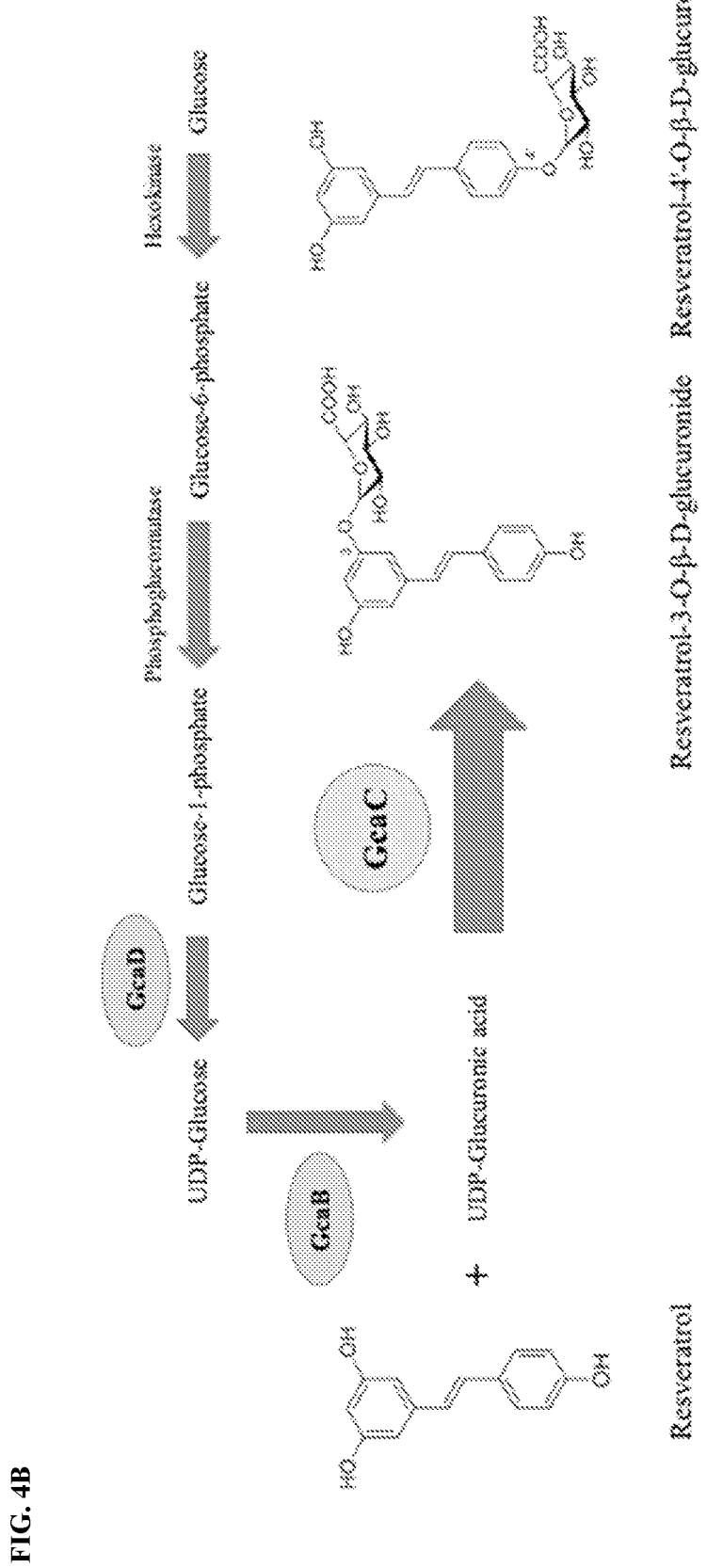

To find out which enzyme is responsible for the glucuronidation in *S. chromofuscus* ATCC 49982, we analyzed the genome of this strain that was previously sequenced by our group. Annotation of the genome indicated that there are more than 30 glycosyltransferases in *S. chromofuscus* ATCC 49982. To narrow down, we looked at the genes adjacent to these glycosyltransferase genes. A gene cluster (FIG. 4A) putatively involved in the glucuronidation was discovered, and the predicted functions of the genes are shown in Table 2. The five genes, named gcaA-E, were predicted to be TetR transcriptional regulator, UDP-glucose dehydrogenase, UDP-glucuronosyltransferase, UDP-glucose pyrophosphorylase, and MFS transporter, respectively. While gcaA and gcaE might be involved in the regulation of the gene cluster and sugar transport, respectively, gcaB, gcaC and gcaD were proposed to be involved in the biosynthesis and transfer of UDP-glucuronic acid (FIG. 4b). More specifically, GcaD (containing 320 amino acids or aa) generates UDP-glucose from glucose-1-phosphate as a UDP-glucose pyrophosphorylase, GcaB (484 aa) functions as a UDP-glucose dehydrogenase to synthesize UDP-glucuronic acid, and finally GcaC (402 aa) transfers the UDP-glucuronic acid moiety to a sugar acceptor such as resveratrol. The nucleotide sequences and amino acid sequences of GcaB, GcaC, and GcaD are presented in Table 3 and Table 4, respectively.

BLAST analysis of the amino acid sequence of GcaC revealed that it is homologous to a number of glycosyltransferases including a few uncharacterized UDP-glucuronyl/UDP-glucosyltransferase, such as those from *Streptomyces malaysiensis* (GenBank accession number NIY63294.1, 408 aa, 70% identity) and *Streptomyces violaceusniger* (GenBank accession number AEM85024.1, 404 aa, 68% identity). Although both genes are not functionally characterized so far, they still provide useful information to predict the function of GcaC.

TABLE 2

The glucuronidation (gca) gene cluster in *S. chromofuscus* ATCC 49982.

| Gene | Size (aa) | Predicted function | Homolog/source/NCBI accession no. | Identity/Similarity |
|---|---|---|---|---|
| gcaA | 230 | TetR family transcriptional regulator | TetR family transcriptional regulator/*Streptomyces* sp. CRXT-G-22]/WP_187751940.1 | 71%/81% |
| gcaB | 484 | UDP-Glucose dehydrogenase | UDP-glucose/GDP-mannose dehydrogenase family protein/*Streptomyces* sp. SolWspMP-5a-2/ WP_093832645.1 | 82%/86% |
| gcaC | 402 | UDP-Glucuronyltransferase | UDP-glucuronyl/UDP-glucosyltransferase/*Streptomyces malaysiensis*/NIY63294.1 | 70%/80% |
| gcaD | 320 | UDP-Glucose pyrophosphorylase | GalU/*Streptococcus pneumonia*/AJ004869.1 | 45%/62% |
| gcaE | 540 | MFS transporter | MFS transporter/*Streptomyces hygroscopicus*/WP_060945424.1 | 83%/90% |

TABLE 3

Nucleotide sequences of gcaB, gcaC, and gcaD.

| Gene | Nucleotide Sequence | SEQ ID NO: |
|---|---|---|
| gcaB | ATGCGGGCCGTTGATCTCCGACACCCGCCCTATGTGTTCAGGTCCGACGACGGCGTCGGACCTGTTCCCCTGC TGGTGATACGGCCGAGGCGCCGGCCCTCGGTGAGGCTGAAACTCGAACAAGCGGAATCGGTGATTCTCATGGG ACTTCGACATATAACCGTCATTGGAACCGGCTATGTCGGTCTGACCACCGGCGCCTGTCTGGCCTCCCTCGGA CACCGGGTGGTGTGCGGATGCCGACGAGGGCAAGGTCGAGCCTCCGGCGGGCGGAGGTCGACATCCTCG AACCGGGCCTTACGGAAGTCGTCCGCGAGGGGCTGGAATCCGGCCGTCTCCAGTTCGTGAGGGACACCCGGGC GGCCGTCGAGGAGGCCGAGGTCGTCTTCCTCTGCCTGCCCACCCCGATGGGCGTCGGAGGCGCCGCCGACCTG GCCGCCGTCGAGGCGGTCGCCGACGAGGTCCGCGACCGCCTGCCGCGTGGCTGCACGGTGGTCAACAAGTCCA CCGTGCCGGTCGGCACCGCCGAGCGCGTCGGCCCCTGCTCGGCCGCCATCGGCCATGACCGTGGTGAGCAACCC GGAGTTCCTCCGCGAGGGACACGCGGTGGACGACTTCCTCCACCCCGACCGGATCGTGGTGGGCGCCGCCGAC GCGGACGCGGCCCGGCTGGTGGCCGACCTGTACCTGGACATCGACGCACCGCGCGTGGTCACCGACACCGCCG GCGCCGAACTCGCCAAGTACGCCGCGAACTTCTTCCTCGCGATGAAGCTGTCGTTCGCGAACAACCTGGCCAC GCTCTGCGAAAGTCTCGGCGCGAACATCGACGACGTGGTCGCTGGCCACCGCCATCCACCGGATCGGCGGC GCCTTCCTCAAGCCCGGGCCCGGATGGGGCGGTTCCTGCCTGCCCAAGGACACGCACGCGCTGCTGCGCGTCT GCGAGGAGTCAGGCGTCGAGTTCCCGCTGCTCCGGGCCACCATCGAGACCAACGTCGAGCACCAGCGCCGGCT CGTCGAGCGGGTGACCGCCGGATGCGCGGGGCGGACGGTTCACTGCGCGGCGTCCGGATCGGGCTGCTCGGT CTCACCTTCAAGGCCGGCACCTTCGACCTGCGCGACTCGCCCGCCCTCGCCCATCGCCCGCCTGCTGCGGGAGC GGGGCGCCGAACTGCGCGCCTACGACCCGGCCCTCAGCGAGCTCCGCCCCGACCTCGGCGATCTGCTCACCAT CACCGGTACCCCCCTCGAAGCGGTCGACGGGGCCCGCGCCTGCGTCGTACTCACCGAGTGGCCGCAATTCCGC GACCTGGACTGGGAGGCCGTCGCCGGGCGGCTCGCCGCGCCGCTCGTCTACGACTTCCGTAACATCCTCGATC CGGCACGGCTCGACAGGGCCGCGCTGACCTGGGAAGGCATCGGTCGTTCGCTGGCAATGGCCAGTTGA | 3 |
| gcaC | GTGCGAGTACTGTTCACCACGCTCGGTAGTCCCTCCCACGGTCGCGCACAGCTTCCGCTGGCCCGGGCGTTCG CCGCGGCCGGACACGACGTCCTCGTGGCCACCACCCCGACCCTCGCCTCCGTCTTCGAACAGGACGACGTCCG GGTGACCGTCTGCATGGGCGATTTCACGCCACAGTCCTTCATCACCCCCGAACTGCTCCAGGAGGCGATGCGG CCGGGTCAGGACGGTGAGCCGCAGGACGCCATGGCGCGCCTCATGCCCGAGATCACCTCCGGCCCGATGGCCA GGAAGCTGTGGGAAGAGATCCTTCCGGTGGCGCGGGAGTTCGCCCCCGACCTCATCCTGCGCGACGGCATGGA CCTGAGCTCGTGCCTGATCGCGGAACACCTCGGCATCCCGCAACTGCCCACCCCTTCGGGCACGAACAACCTC ATCGACCCCGCCATGGTGCTGCCCGGCCTGAACGTCCTGCGGAAGGAATTCGGGCTGTCCGCCCAGGAGGACC CGCTGTCCGTCGTCCCCCACGGGCGCGTCGACTACGTACCGGCGGCCTTCTGTTCGCCCAGCACCTGCCCTC GTCGTGGTCCTACCGGCAGACCGTGACCGTGGACCGCAGCTCGGTCCTGCCGGAGTGGATCGCCCAACTGCCC ACCGACCGCCCCTGGTGTTCGCCGCGCTCGGCACCGCCCTTCCGATGATCAGGGAGATGGGGGCCGAGGCGA CCGGGCCGTCGCTGTTCCCGATGCCGGACCCGGTGGACACGCTGCGGTTGATGATCGAGGCGGTGTCGCGGCT CGACGACTGCACCGTGGTCGTCGCCACCTCCGGCATCCGGCGGACACCGAGGGGCCTGCCGCCGCATGTGCAC GTCACCGACCGGGTGCCGCAGCCCCTGCTGCTGGAGTCCGTCGACGCGTTCCTCACCCACGGCGGCTTCAACA GCATCCGGGAGGCGCTGCGCACGGCCACCCCGATGGCGGTGCTGCCCCAGTTCGGCGACCAGCCCGCCAACGC GCGCCGCGTCGAGGAACTCGGCCTCGGCCGGGAGATCACCGACATCACCGCGGACGGCATCACCAAGGCCGTA CGCGAGGTGCTGACCGACCCCGGCATCCGGGCCAGGACGCGCGAGGCCCGGCTGGCGATGCTGGCGCTGCCGG AGATCGACAGCGCCGTGGCCGACCTGCAGAAGATCGTCTGA | 4 |
| gcaD | ATGTCGCCTTCCCCGCCCCTGCCACCACCGTCACCAAGGCCGTGATACCGGCCGCCGGCCTGGGCACCCGCT TCCTCCCGGCGACGAAGGCCATGCCCAAGGAGATGCTGCCCGTCGTCGACCGCCCGGCCATCCAGTACGTGGT GGAAGAGGCCGCCGGCGCCGGTCTCTCCGATCTGCTCGTGATCACCGGGCGGAACAAGCGCCCGCTGGAGGAC CACTTCGACCACGCCTGGGAACTGGAGGAGGCCCTGACCCGCAAGGGCGACGAGGGCAGGCTGCGCAGTGTCC GGGAGTCCACCGCGCTCGCCGCGATCCACTACGTCCGGCAGGGCACCCCGGCGGGCCTCGGACACGCCGTGCT CTGCGCCAACAGCACGTGGGGGACGAGCCGTTCGCCGTACTCCTGGGCGACGACCTCATCGACCCGCGCGAT CCACTGCTCACCCGGATGATCGAGATACGGGAACGGTTCGGCGGCAGCGTGGTCGCGCTGATGGAGACCGACC CCGCCTCGATCCACCTGTACGGCTGCGCGGCGGTCGAACCCACCGCACAGGACGATGTCGTACGCCTGACCGA CCTGGTGGAGAAGCCCGCCCCGGGGCAAGCCCCCAGCGCGTACGCGGTCATCGGACGCTATCTGCTGGACCCG GCCGTGTTCGAGGTGCTGCGCCGACACCCGCCCGGCCACGGCGGCGAGATCCAGCTCACCGACCCCCTGCGCG AACTGGCGCACGGCGGTGCCACCTCCCCGGGCGGCCCGGTCCACGGCGTGCTGTTCACCGGACGGCGCTACGA CACCGGCGACCGCGCCGAGTACCTGCGCACCATCGTCCGACTGGCCTACGAACACGACGACCTCGGCCCCGGG TTCCGGGAGTGGCTGACCGCGTTCGTCGACGCCGAACGCGAGGCCCCCACCGCGGCGGCCGACGGCGGCCCGG GTGTCGCGGCATGA | 5 |

TABLE 4

Amino acid sequences of GcaB, GcaC, and GcaD.

| Protein | Amino Acid Sequence | SEQ ID NO: |
|---|---|---|
| GcaB | MRAVDLRHPPYVFRSDDGVGPVPLLVIRPRRRPSV RLKLEQAESVILMGLRHITVIGTGYVGLTTGACLA SLGHRVVCADADEGKVERLRRAEVDILEPGLTEVV REGLESGRLQFVRDTRAAVEEAEVVFLCLPTPMGV GGAADLAAVEAVADEVRDRLPRGCTVVNKSTVPVG TAERVAALLGRPDVTVVSNPEFLREGHAVDDFLHP DRIVVGAADADAARLVADLYLDIDAPRVVTDTAGA ELAKYAANFFLAMKLSFANNLATLCESLGANIDDV VAGIGHDPRIGGAFLKPGPGWGGSCLPKDTHALLR VCEESGVEFPLLRATIETNVEHQRRLVERVTAGCA GADGSLRGVRIGLLGLTFKAGTFDLRDSPALAIAR LLRERGAELRAYDPALSELRPDLGDLLTITGTPLE AVDGARACVVLTEWPQFRDLDWEAVAGRLAAPLVY DFRNILDPARLDRAALTWEGIGRSLAMAS | 6 |
| GcaC | VRVLFTTLGSPSHGRAQLPLARAFAAAGHDVLVAT TPTLASVFEQDDVRVTVCMGDFTPQSFITPELLQE AMRPGQDGEPQDAMARLMPEITSGPMARKLWEEIL PVAREFAPDLILRDGMDLSSCLIAEHLGIPQLPTP SGTNNLIDPAMVLPGLNVLRKEFGLSAQEDPLSLV PHGRVDYVPAAFSFAQHLPSSWSYRQTVTVDRSSV LPEWIAQLPTDRPLVFAALGTALPMIREMGAEATG PSLFPMPDPVDTLRLMIEAVSRLDDCTVVVATSGI PADTEGLPPHVHVTDRVPQPLLLESVDAFLTHGGF NSIREALRTATPMAVLPQFGDQPANARRVEELGLG REITDITADGITKAVREVLTDPGIRARTREARLAM LALPEIDSAVADLQKIV | 7 |
| GcaD | MSPSPPPATTVTKAVIPAAGLGTRFLPATKAMPKE MLPVVDRPAIQYVVEEAAGAGLSDLLVITGRNKRP LEDHFDHAWELEEALTRKGDEGRLRSVRESTALAA IHYVRQGTPAGLGHAVLCAQQHVGDEPFAVLLGDD LIDPRDPLLTRMIEIRERFGGSVVALMETDPASIH LYGCAAVEPTAQDDVVRLTDLVEKPAPGQAPSAYA VIGRYLLDPAVFEVLRRTPPGHGGEIQLTDALREL AHGGATSPGGPVHGVLFTGRRYDTGDRAEYLRTIV RLAYEHDDLGPGFREWLTAFVDAEREAPTAAADGG PGVAA | 8 |

Example 6. Heterologous Expression and Purification of GcaC from *E. coli* BL21(DE3)

Figure 5A:
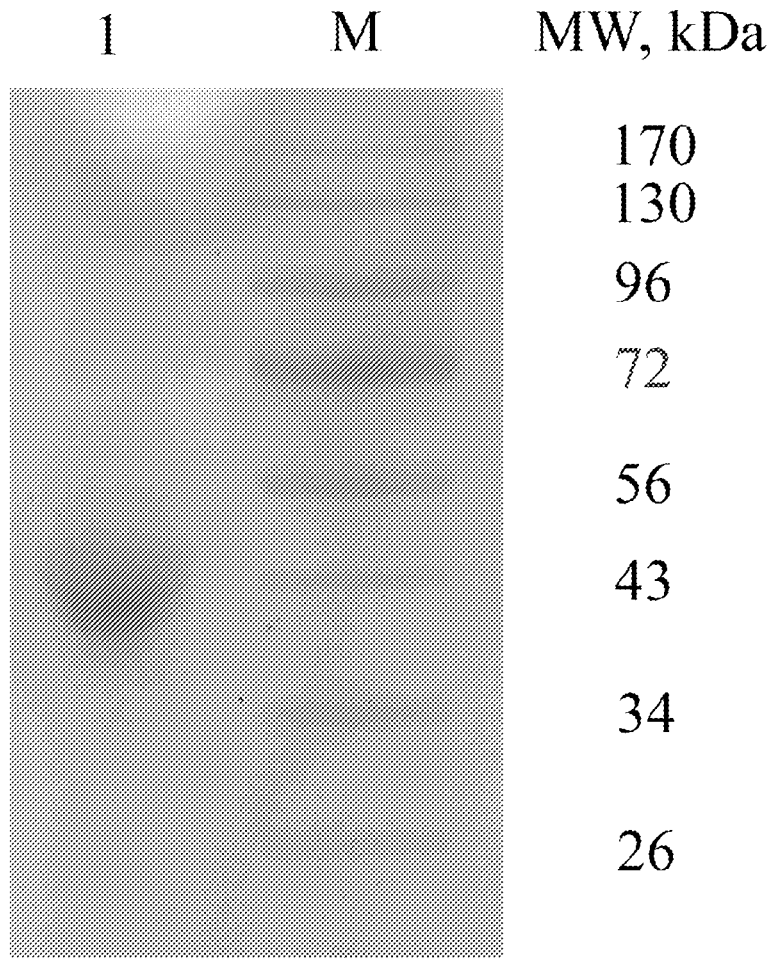
FIGS. 5A-5D depict heterologous expression and in vitro functional characterization of GcaC.

To identify the function of GcaC, we amplified this gene from the genomic DNA of *S. chromofuscus* and ligated it to pET28a to yield the corresponding expression plasmid, pJR36 (pET28a-gcaC). The plasmid was then expressed in *E. coli* BL21(DE3) with IPTG induction. Ni-NTA column chromatography was used to purify the N-His6-tagged GcaC from the cell lysate and the purified enzyme was analyzed by SDS-PAGE. As shown in FIG. 5a, GcaC (~43.4 kDa) was expressed and purified from *E. coli* BL21(DE3)/pJR36 to homogeneity and the isolation yield of this enzyme was 11.87 mg/L.

Example 7. In Vitro Functional Characterization of GcaC

Figure 5B:
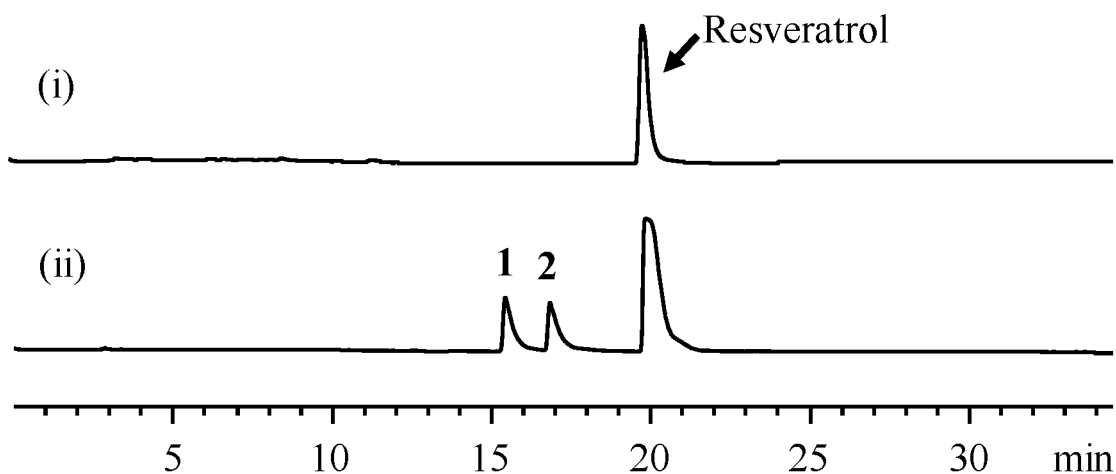
Figure 5C:
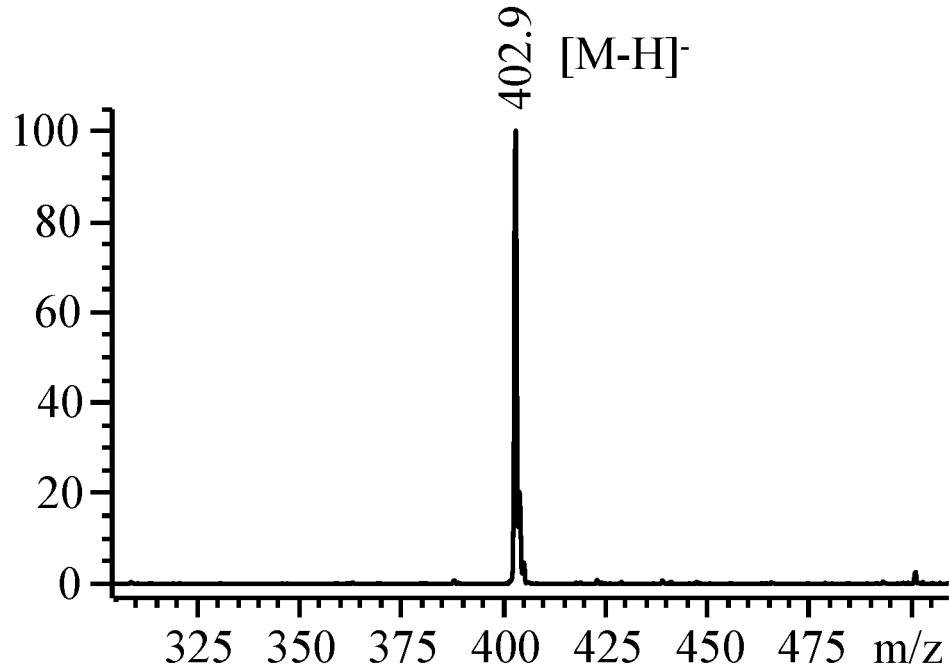
Figure 5D:
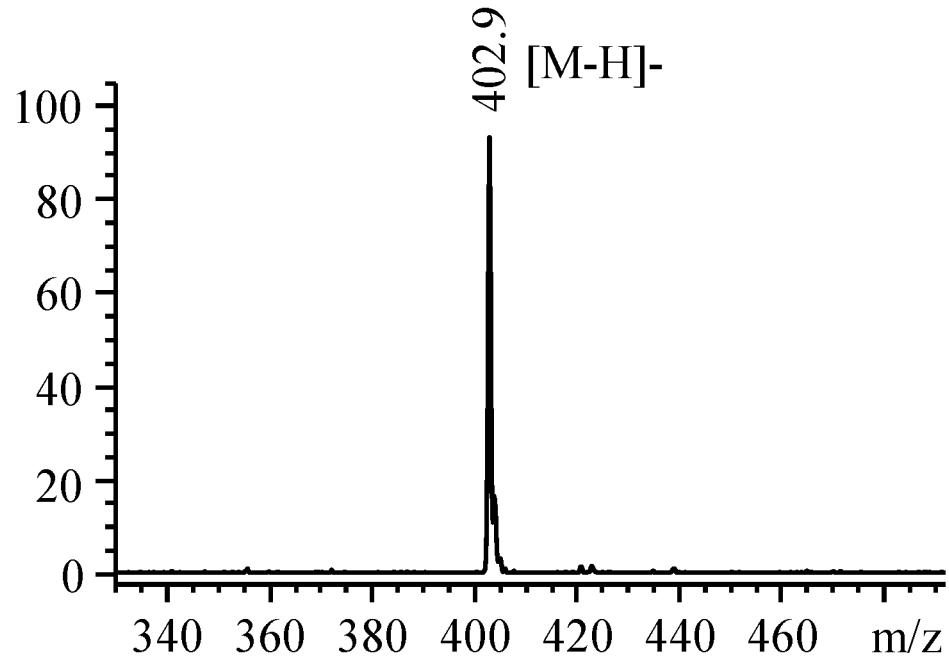

To check the function of purified GcaC, resveratrol was incubated with this enzyme in the presence of UDP-glucuronic acid. HPLC analysis showed that compared to the control (trace i, FIG. 5B), two polar products were formed from resveratrol (trace ii, FIG. 5B). Two products showed the similar UV spectra to the substrates. ESI-MS spectra (FIGS. 5C and 5D) of these products showed the corresponding quasi-molecular ion [M-H]$^-$ at m/z 402.9, respectively. Therefore, they have the same molecular weight of 404, which is 176 mass units larger than the substrate resveratrol, indicating that a glucuronic acid moiety was added to different positions of resveratrol. Furthermore, the retention times of these two in vitro products were the same as those of resveratrol-4'-O-β-D-glucuronide and resveratrol-3-O-β-D-glucuronide produced in the in vivo biotransformation by *S. chromofuscus*. Formation of the two resveratrol glucuronides in the in vitro reactions allowed the characterization of GcaC as the responsible UGT in *S. chromofuscus*.

Example 8. Broad Substrate Specificity of GcaC Toward Sugar Acceptor Substrates To explore the substrate specificity of GcaC, this enzyme was reacted with different sugar donors and sugar acceptors. UDP-Glucose is structurally similar to UDP-glucuronic acid and the BLAST analysis of the sequence of GcaC suggested that this enzyme is homologous to a predicted UDP-glucuronyltransferase or UDP-glucosyltransferase from *S. malaysiensis* (Table 2). Therefore, we reacted resveratrol with UDP-glucose in the presence of GcaC. However, no products were formed from resveratrol (data not shown), indicating that GcaC is a specific UDP-glucuronyltransferase that strictly transfers UDP-glucuronic acid.

Figure 6A:
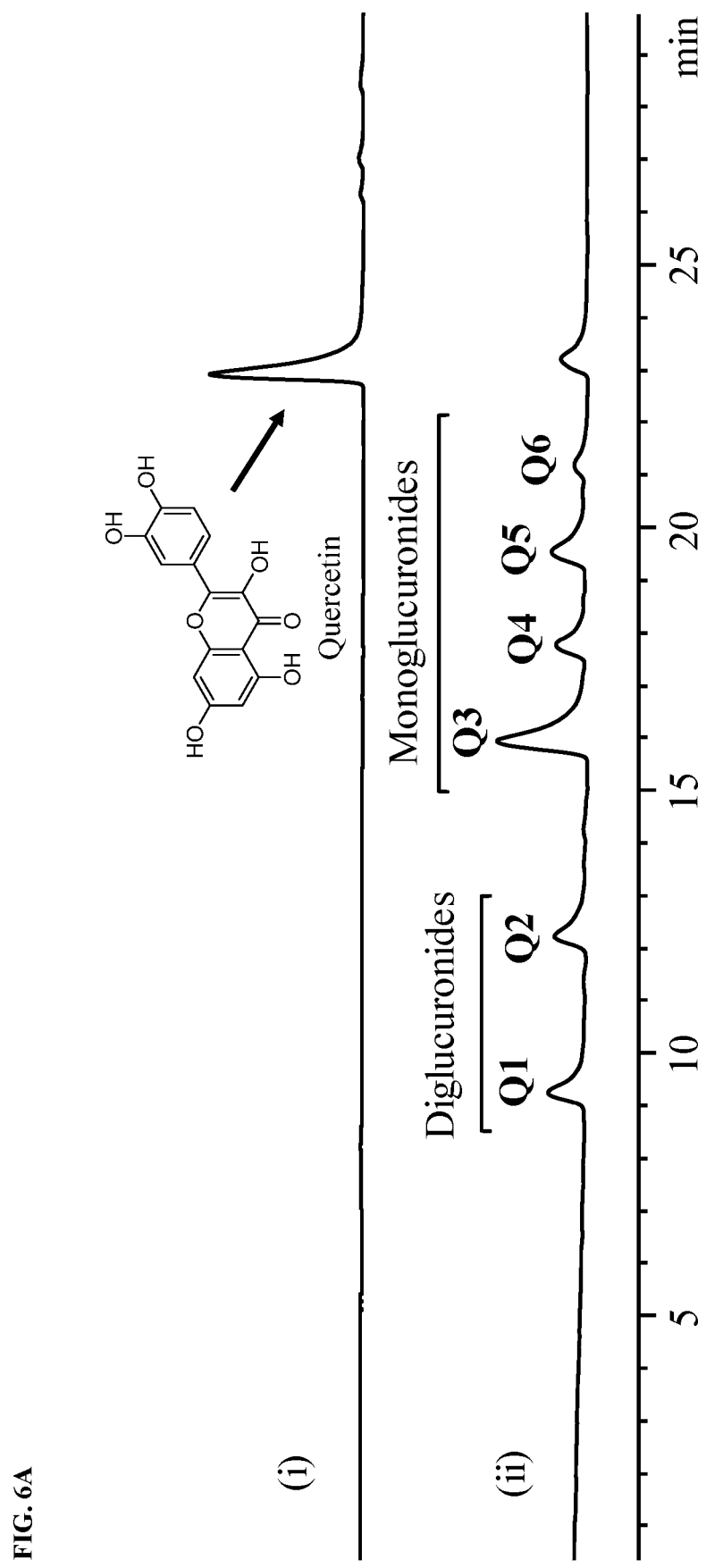
FIGS. 6A-6H depict HPLC analyses of in vitro glucuronidation of different sugar acceptor substrates by GcaC.

We next investigated the substrate specificity of GcaC to sugar acceptor substrates by reacting various natural products, including quercetin, ferulic acid, vanillic acid, curcumin, vanillin, chrysin, zearalenone and apigenin, with UDP-glucuronic acid in the presence of GcaC. When quercetin was used as the substrate, HPLC analysis (FIG. 6A) showed that six polar products were formed. All products showed the similar UV spectra to the substrate. ESI-MS spectra of Q1-Q6 showed the corresponding quasi-molecular ion [M-H]$^-$ at m/z 653.0, 653.0, 476.9, 476.9, 476.9, and 476.9, respectively. Therefore, products Q3-Q6 have the same molecular weight of 478, which is 176 mass units larger than the substrate quercetin, indicating that a glucuronic acid moiety was added to different hydroxyl groups of quercetin. Since quercetin has five free phenolic hydroxyl groups, we propose that the glucuronic acid moiety was introduced to four of these hydroxyl groups to generate the four monoglucuronides. The molecular weight of both Q1 and Q2 were found to be 654, which is 352 mass units larger than the substrate quercetin or 176 units larger than products Q3-Q6, suggesting that two glucuronic acid moieties were added to quercetin to form diglucuronides. Therefore, this enzyme not only adds the glucuronic acid moiety to different hydroxyl groups of quercetin, but also accepts the resulting monoglucuronides as the substrates to further generate diglucuronides.

Figure 6B:
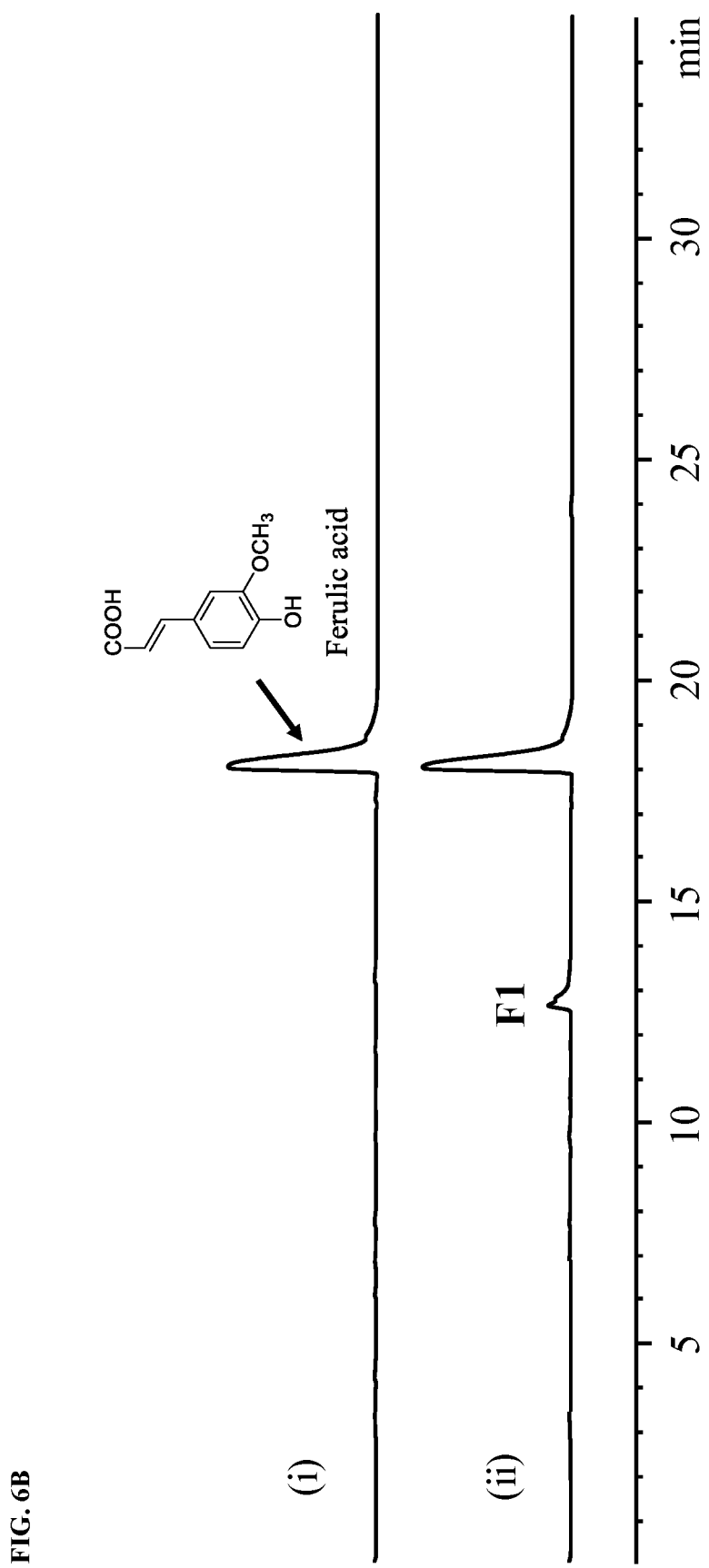
Figure 6C:
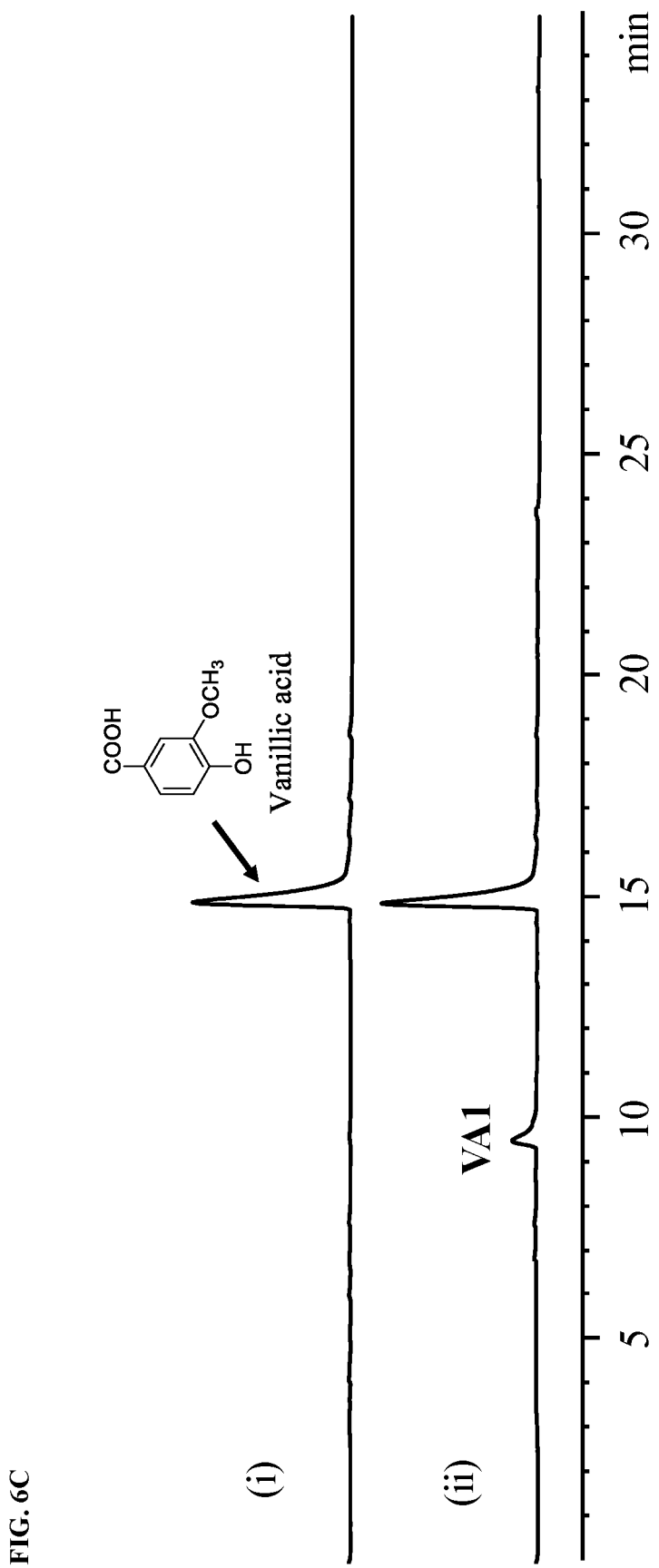

When ferulic acid was incubated with GcaC, one polar product F1 at 12.8 min was detected by HPLC (FIG. 6B). Similarly, one product VA1 appeared at 9.7 min when vanillic acid was used as a sugar acceptor (FIG. 6C). Both products showed the similar UV spectra to the corresponding substrates. The ESI-MS spectra of F1 and VA1 showed a [M-H]$^-$ ion peak at m/z 368.9 and 342.9, respectively, indicating that their molecular weights are 370 Da and 344 Da, which are consistent with the addition of a glucuronic acid moiety to ferulic acid and vanillic acid, respectively. Furthermore, the retention times of F1 and VA1 are the same as 5 and 6 from the biotransformation by *S. chromofuscus* 49982, namely ferulic acid-4-O-β-D-glucuronide and vanillic acid-4-O-β-D-glucuronide.

Figure 6D:
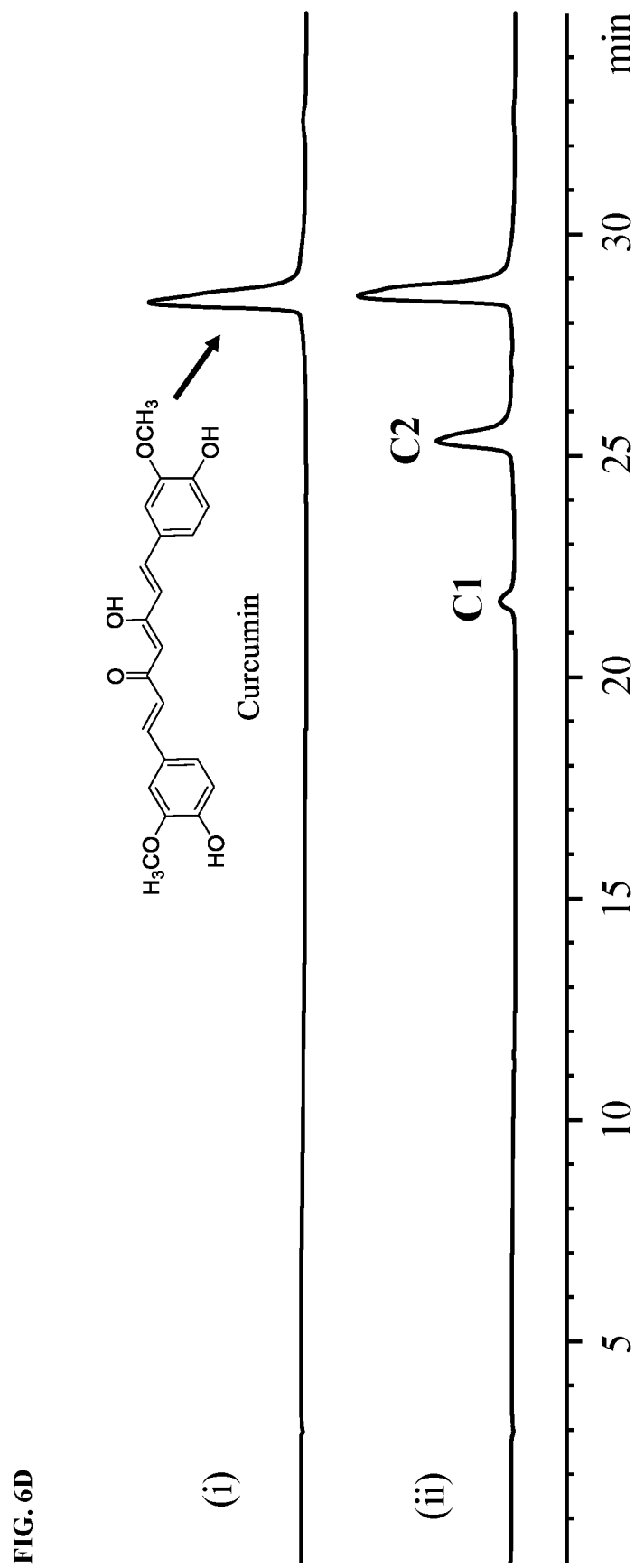

Meanwhile, when curcumin was used as the substrate, HPLC analysis showed that compared to the negative control (trace i, FIG. 6D), GcaC generated two polar products C1 and C2 (trace ii, FIG. 6D), at 21.8 and 25.3 min respectively. The two products had the UV spectra similar to that of the substrate. The ESI-MS spectra of the two products showed the [M-H]$^-$ ion peak at m/z 719.1 and 542.8, indicating that their molecular weights are 720 Da and 544 Da, respectively. These are consistent with a diglucuronide and a monoglucuronide of curcumin, whose molecular weight is 368 Da. This result further indicated that GcaC can transfer one or two glucuronic acid moieties to curcumin.

Figure 6E:
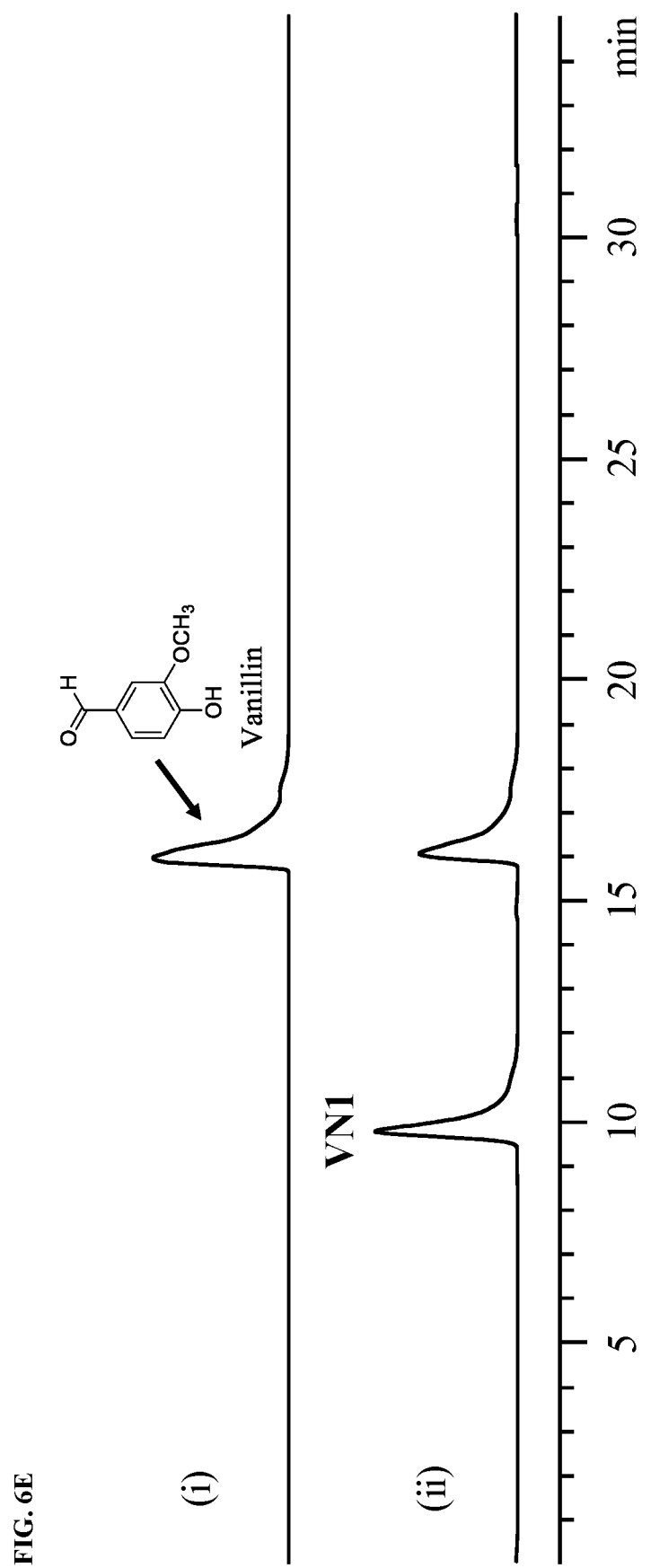
Figure 6F:
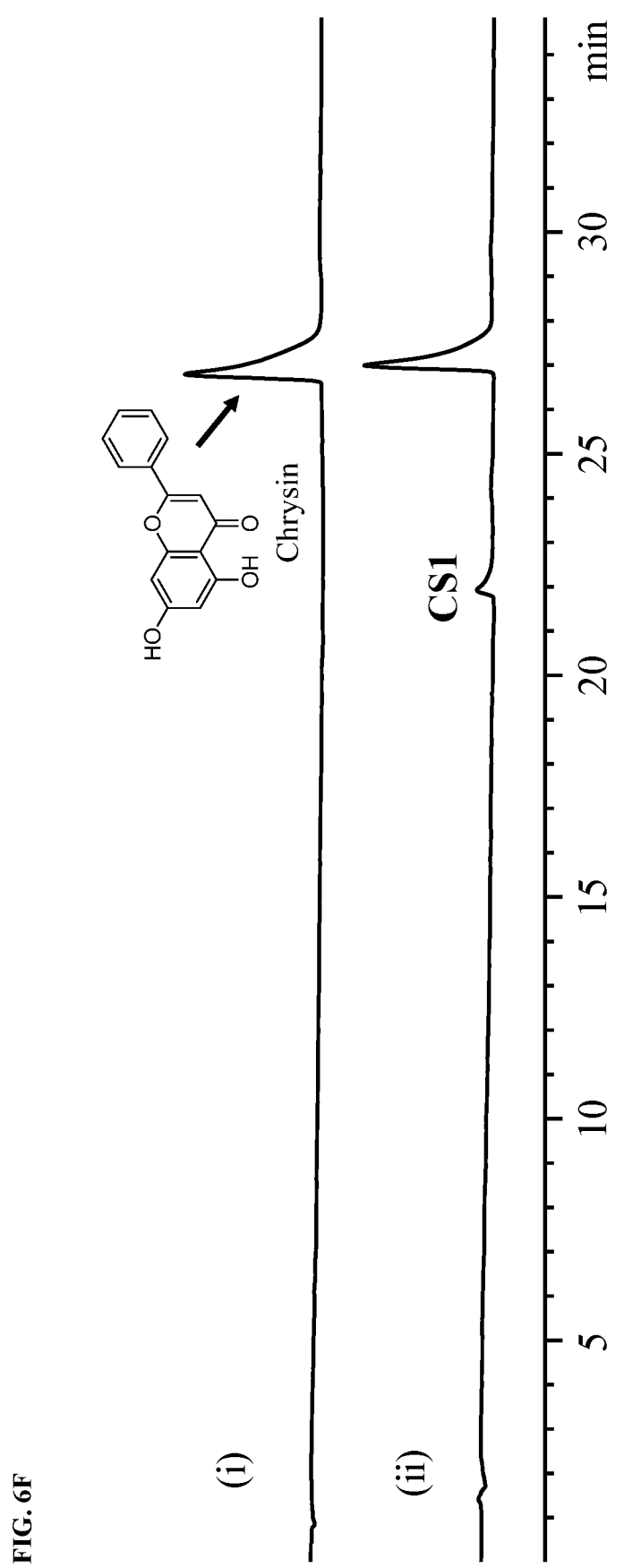
Figure 6G:
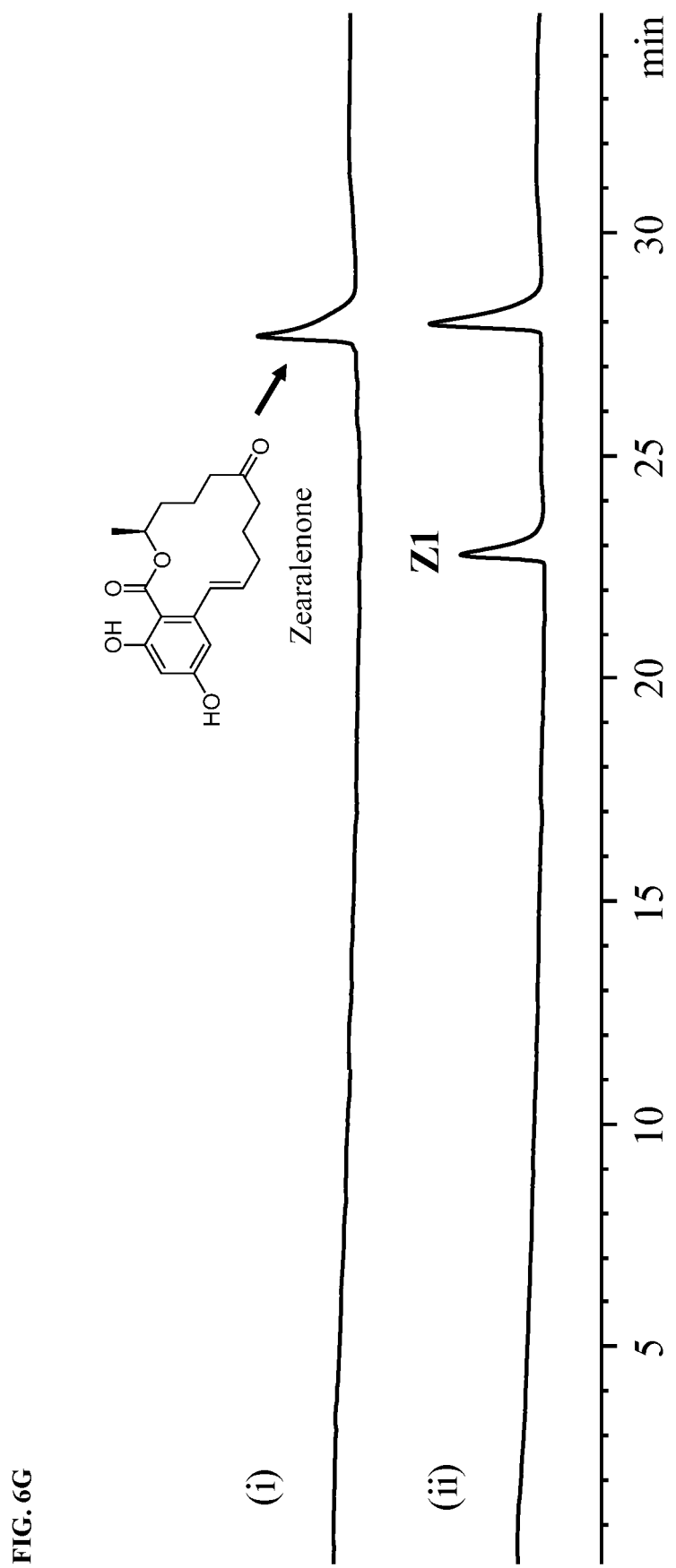
Figure 6H:
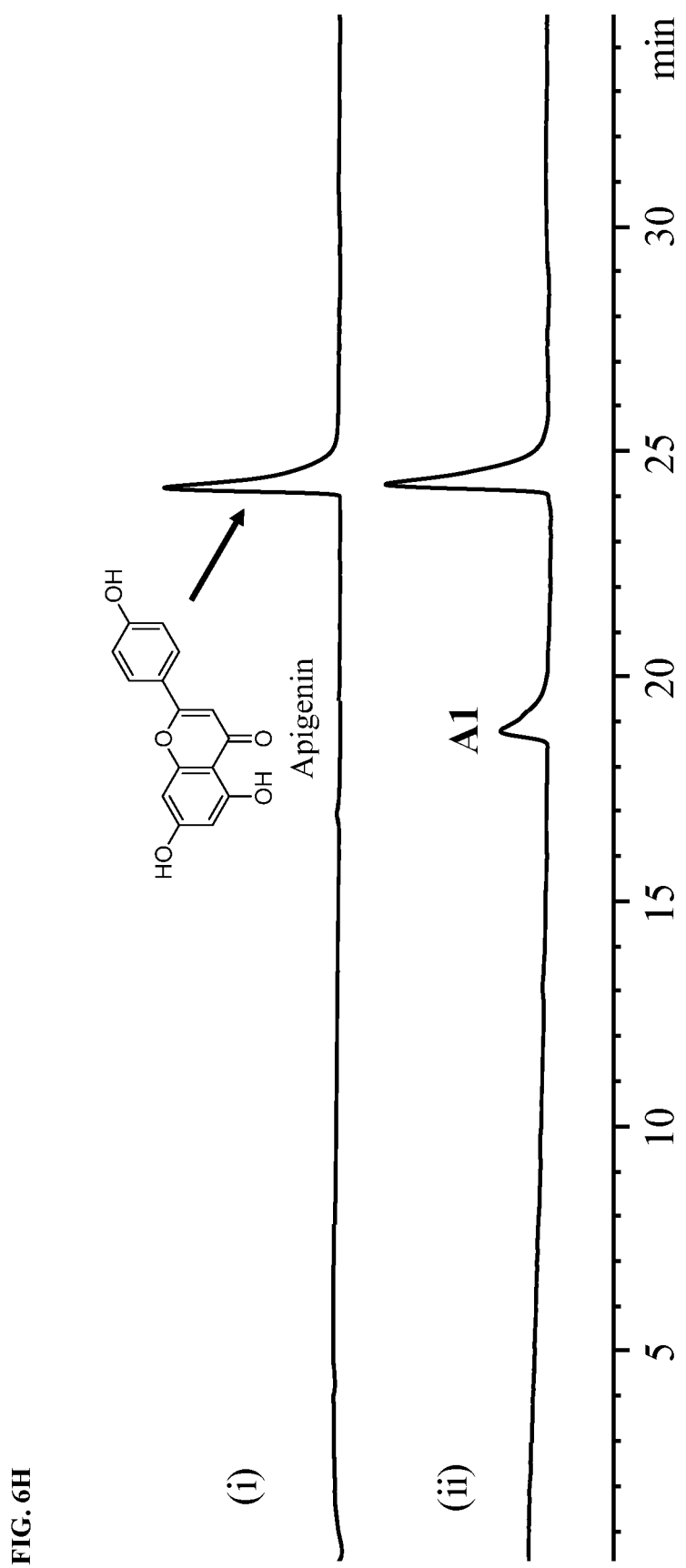

Similarly, we also used vanillin as the substrate, and one polar product VN1 at 10.0 min was detected by HPLC (FIG. 6E). One product CS1 was also observed at 22.0 min when chrysin was incubated with GcaC (FIG. 6E). Both products showed the similar UV spectra to their relative substrates. The ESI-MS spectra of VN1 and CS1 showed a [M-H]$^-$ ion peak at m/z 326.9 and 428.8, respectively, indicating that their molecular weights are 328 Da and 430 Da, which are consistent with the addition of a glucuronic acid moiety to vanillin and chrysin, respectively. Similarly, when zearalenone and apigenin were used as the substrates, HPLC analysis showed that compared to the negative controls (trace i, FIGS. 6g and 6h), GcaC generated a product Z1 (trace ii, FIG. 6G) at 23.0 min from zearalenone and a product A1 (trace ii, FIG. 6H) at 19.0 min from apigenin. The products showed the UV spectra similar to those of their substrates. The ESI-MS spectrum of Z1 exhibited the [M-H]$^-$ ion peak at m/z 493.1, which means the molecular weight is 494 Da and it is in accord with the addition of a glucuronic acid moiety to zearalenone with a molecular weight of 318. The ESI-MS spectrum of A1 showed the [M-H]$^-$ ion peak at m/z 445.1, indicating that molecular weight is 446 Da. This is consistent with a monoglucuronide of apigenin, whose molecular weight is 270 Da. Therefore, GcaC synthesized the corresponding glucuronides from zearalenone and apigenin.

Example 9. Determination of the Optimal In Vitro Reaction Conditions of GcaC

Figure 7A:
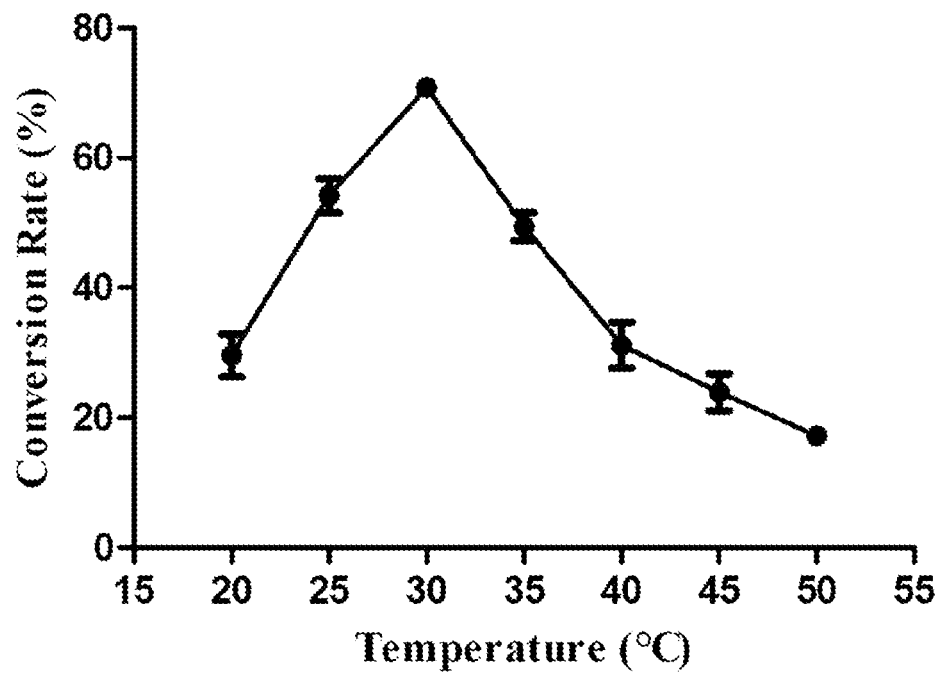
FIGS. 7A-7C depict the determination of the optimum in vitro reaction conditions for GcaC.

The effects of reaction temperature and pH on the GcaC-catalyzed glucuronidation were examined. Purified GcaC was incubated with resveratrol and UDP-glucuronic acid under different conditions. First, the reaction was conducted at different temperatures ranging from 20° C. to 50° C. The conversion rates of resveratrol were quantified by HPLC and compared. As shown in FIG. 7A, GcaC has the highest glucuronidation activity at 30° C. with the highest conversion rate. When the temperature increased from 20° C. to 30° C., the conversion rate of resveratrol increased from 29.61% to 70.85%. However, when the reaction temperatures were above 30° C., the resveratrol conversion rate gradually decreased. Furthermore, the conversion rate reduced approximately by 53.60% at 50° C. compared to that at 30° C. Therefore, the optimum reaction temperature for GcaC was determined to be 30° C.

Figure 7B:
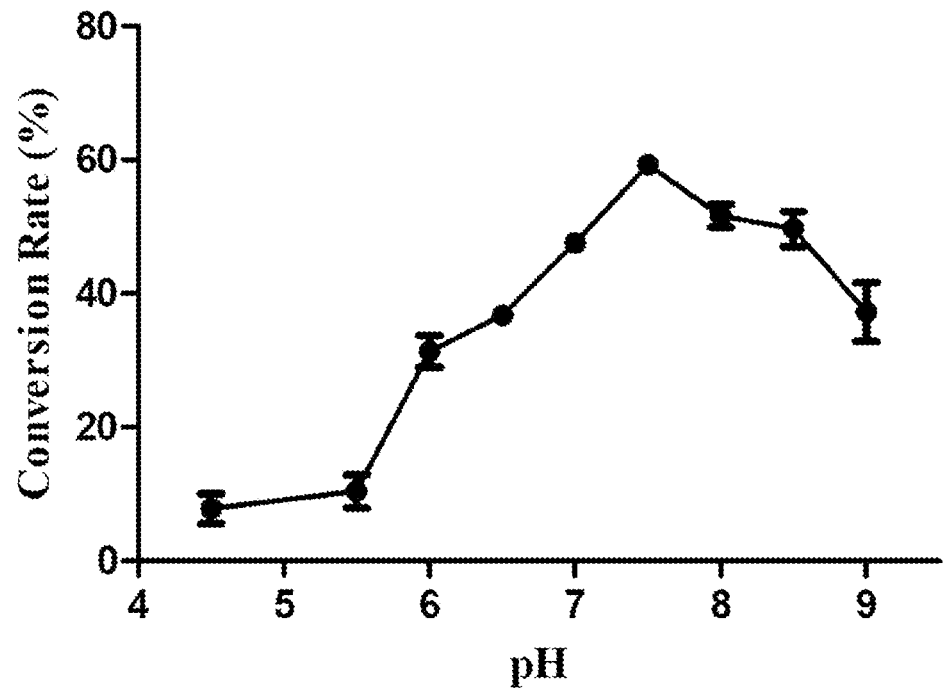

Next, we determined the pH effect on the glucuronidation activity of GcaC. The enzyme was reacted with resveratrol in 200 mM phosphate buffer at 30° C. but at different pH values, including 4.5, 5.5, 6, 6.5, 7, 7.5, 8, 8.5 and 9. With the increase of pH from 4.5 to 7.5, the conversion rate of resveratrol by GcaC steadily increased from 7.8% to 59.3%. Nevertheless, when the pH value further increased to 9.0, the conversion rate decreased to 37.2% (FIG. 7B). Hence, the optimum pH for GcaC is 7.5.

Figure 7C:
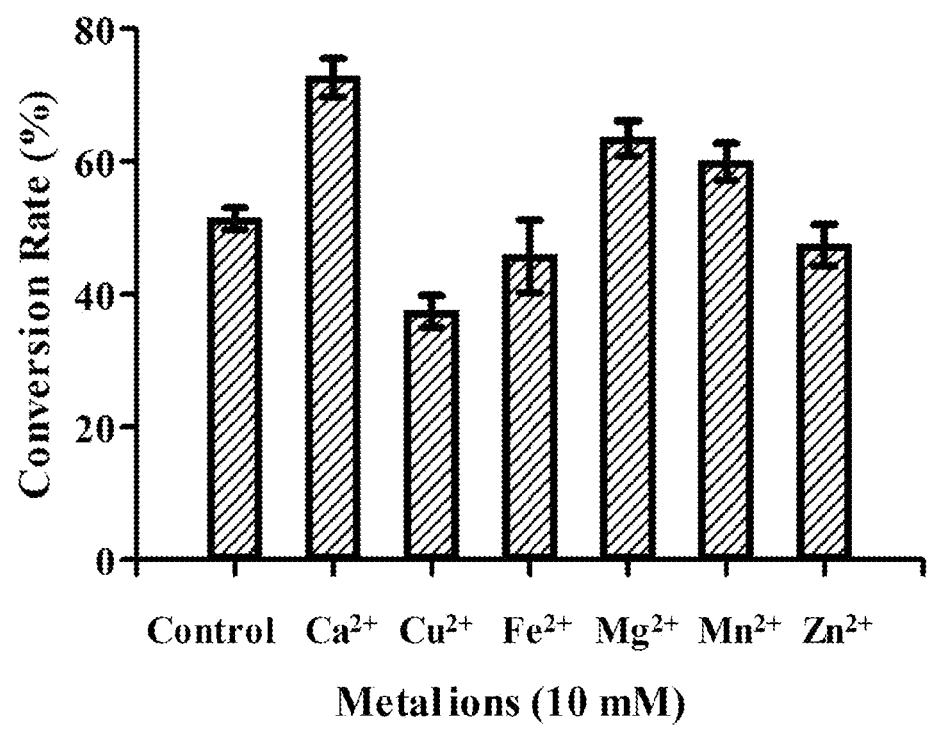

Apart from temperature and pH effects, we also investigated the effect of various metal ions on the activity of GcaC. At 10 mM, we found that $Ca^{2+}$, $Mg^{2+}$, and $Mn^{2+}$ had a simulative function on the UGT activity of GcaC (FIG. 7C). With these three metal ions applied in the enzymatic reaction, the catalytic activity was 1.33, 1.27, and 1.09-fold higher than that of the control group, respectively. Among these three metal ions, $Ca^{2+}$ has the strongest stimulating effect. By contrast, the activity of GcaC was inhibited when $Cu^{2+}$, $Fe^{2+}$, and $Zn^{2+}$ were added into the reaction system. The conversion rate of resveratrol decreased from 52.3% to 39.1%, 48.6%, and 43.8% (FIG. 7C), respectively. In conclusion, the optimal in vitro reaction conditions for purified GcaC are at 30° C., pH 7.5 with 10 mM of $Ca^{2+}$.

Example 10. Optimized Production of Resveratrol-4'-O-β-D-Glucuronide and Resveratrol-3-O-β-D-Glucuronide with the Engineered E. coli BL21 (DE3)

Figure 8A:
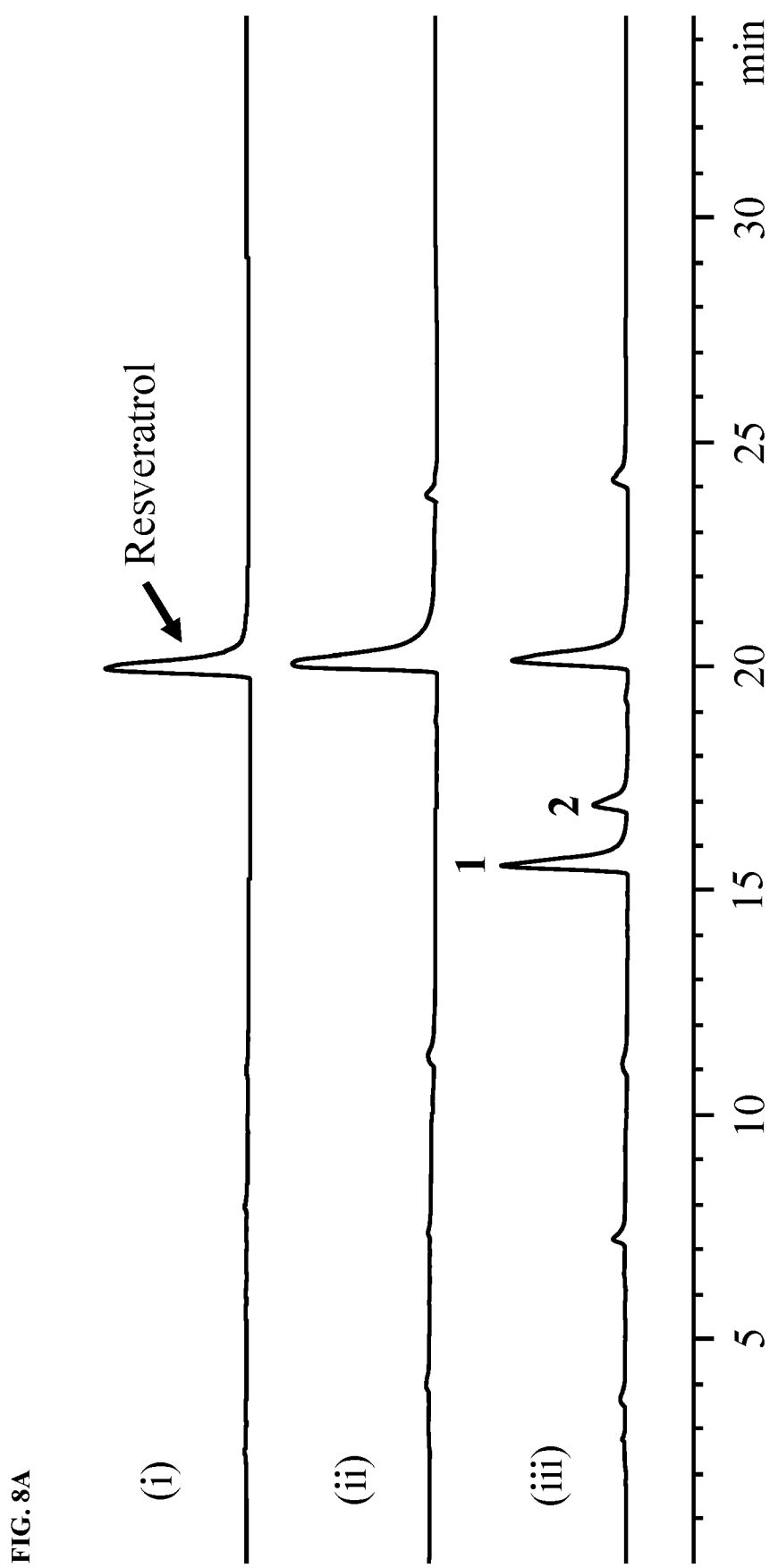
FIGS. 8A-8F depict optimization of in vivo production of resveratrol glucuronides by E. coli BL21(DE3)/pJR36.

We next tested whether E. coli BL21(DE3)/pJR36 can convert resveratrol into the two glucuronides. To this end, resveratrol was incubated with the IPTG-induced broth of this engineered strain, with E. coli BL21(DE3)/pET28a as the negative control. As shown in FIG. 8A, compared to the commercial standard (trace i) and negative control (trace ii), incubation of resveratrol with E. coli BL21(DE3)/pJR36 yielded the glucuronidation products 1 and 2.

Figure 8B:
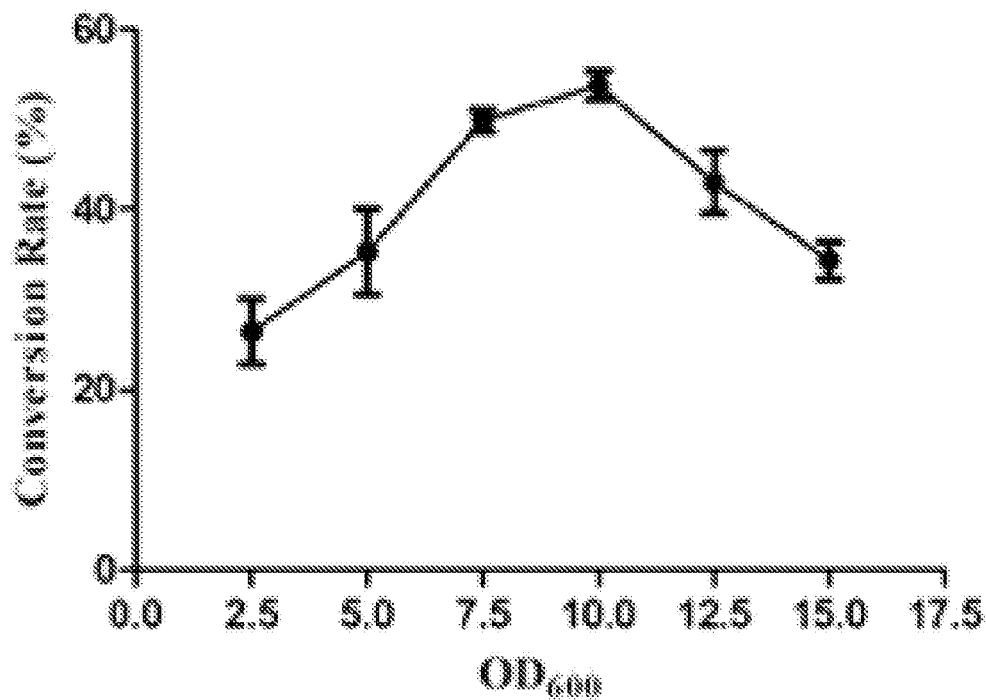

In vivo biotransformation of resveratrol by E. coli BL21 (DE3)/pJR36 indicated that GcaC can generate resveratrol-4'-O-β-D-glucuronide as the major product from resveratrol in E. coli, which provides an alternative approach to biosynthesize this resveratrol glucuronide. Therefore, it is critical to discover the optimal conditions for this whole-cell bioconversion process. The effect of different cell concentrations on the formation of resveratrol glucuronides at 40° C. overnight was first investigated, ranging from $OD_{600}$ 2.5 to 15.0. In the presence of 1.5 mM resveratrol and 0.11 M glucose, we discovered that the conversion rate of resveratrol steadily increased with increasing cell concentrations within the range of $OD_{600}$ 2.5-10.0 (FIG. 8B). The conversion rate of resveratrol in the biotransformation system reached 53.8% when the $OD_{600}$ value was 10.0, which was 27.3% higher than the titer at $OD_{600}$ 2.5. However, further increase in cell concentration resulted in a drop of the conversion rate. The conversion rate of resveratrol decreased to 34.4% at $OD_{600}$ 15.0, indicating that oversaturated cells did not yield more products.

Figure 8C:
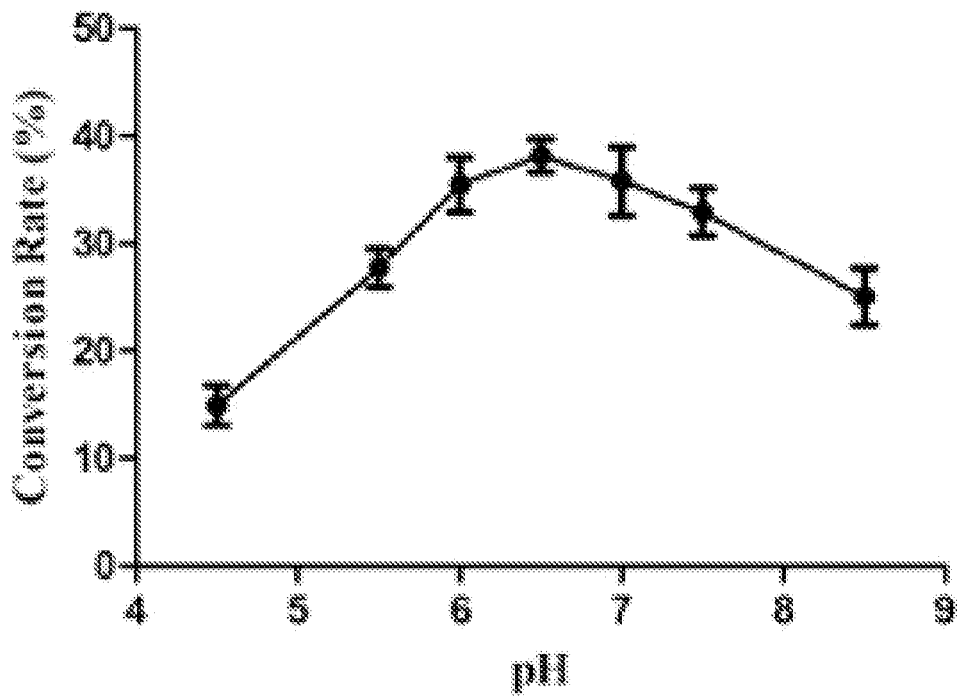
Figure 8D:
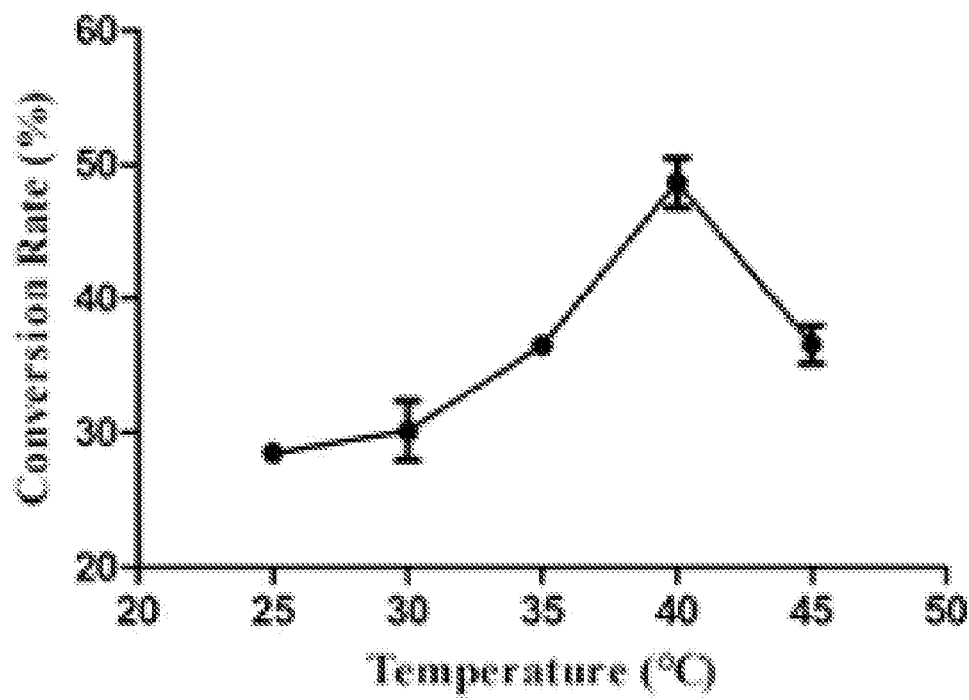

The conversion of resveratrol to its glucuronides was also determined by HPLC at different pH values (pH 4.5-8.5). When the reaction pH was 6.5, the conversion rate reached its highest level, namely 38.1% (FIG. 8C), which is 23.2% higher than that at pH 4.5. We next investigated the impact of temperature on the whole-cell conversion efficiency of resveratrol to its glucuronides. Specifically, E. coli BL21 (DE3)/pJR36 cells ($OD_{600}$ 10.0) were incubated with resveratrol at different temperatures ranging from 25 to 45° C. in 200 mM phosphate buffer (pH 6.5). It was clearly proved that the higher temperature could effectively improve the conversion of resveratrol into resveratrol-4'-O-β-D-glucuronide and resveratrol-3-O-β-D-glucuronide. The highest conversion rate reached 48.6% at 40° C. (FIG. 8D). Further temperature increase to 45° C. resulted in a lower conversion rate.

Figure 8E:
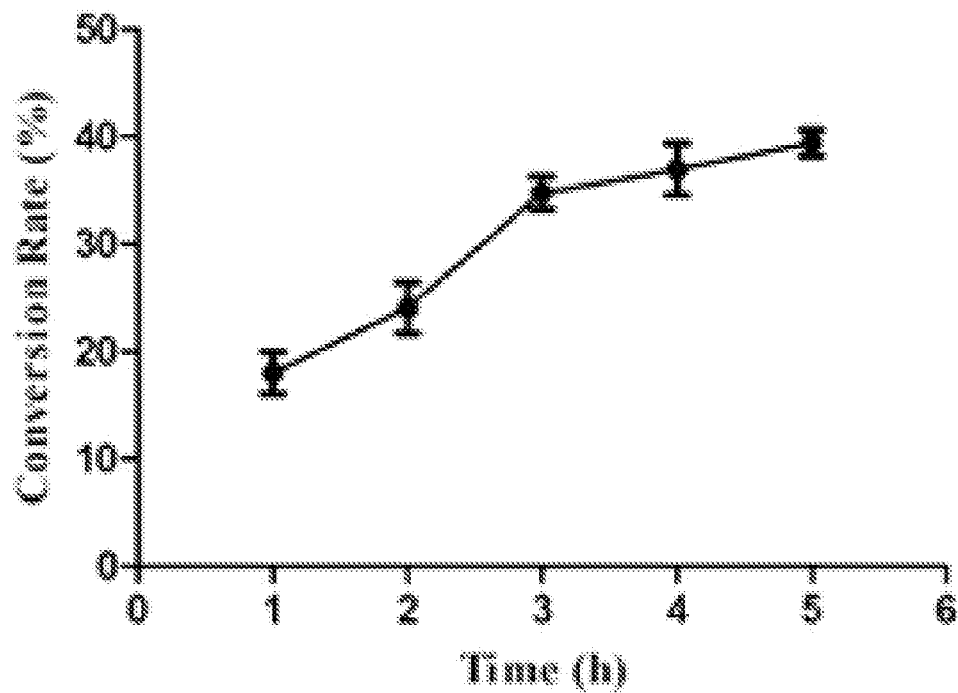

To determine how the bioconversion time affects the conversion rate of resveratrol in the engineered E. coli strain, we conducted a time course analysis for the conversion of 1.0 mM resveratrol to its glucuronides. The experiments were performed with GcaC-expressing E. coli BL21 (DE3) strain ($OD_{600}$ 10.0) at 40° C. in 200 mM phosphate buffer (pH 6.5). The reaction was sampled at 1, 2, 3, 4 and 5 hours. Within the first 3 hours, the conversion rate of resveratrol increased from 18.0% to 34.8% (FIG. 8E). After that, the increase in the conversion rate slowed down gradually. Thus, we chose 3 hours as the preferred reaction time.

Figure 8F:
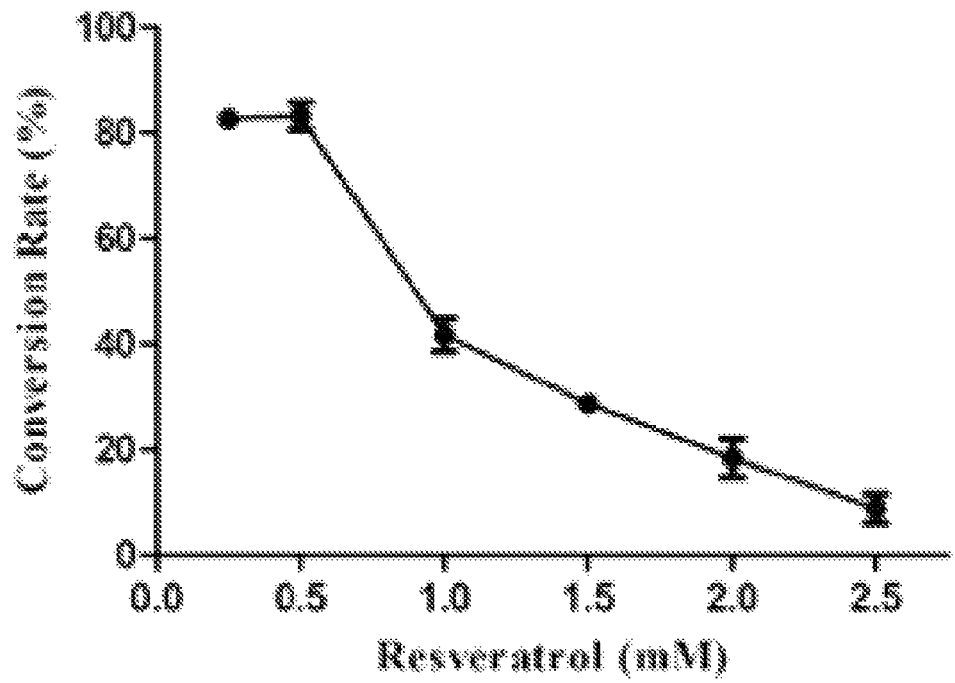

Substrate concentration can also affect the bioconversion rate. Therefore, we next tested different resveratrol concentrations ranging from 0.25 to 2.5 mM, for further optimizing the production of resveratrol-4'-O-β-D-glucuronide and resveratrol-3-O-β-D-glucuronide. The reactions were conducted at pH 6.5, $OD_{600}$ 10, and 40° C. for 3 hours. The conversion rates of resveratrol to its glucuronides were similar when the substrate concentration were 0.25 mM and 0.5 mM, namely 82.6% to 83.2%. However, the conversion rate fell to 41.7% when the concentration of resveratrol was further increased to 1.0 mM (FIG. 8F). When the concentration of resveratrol was further increased to 2.5 mM, the conversion rate dramatically decreased to 7.9%. As a result, 0.5 mM was deemed to be the optimal substrate concentration according to the productivity of resveratrol glucuronides under the selected reaction conditions.

Finally, we scaled up the reaction to 1 L considering all the effects mentioned above. The titer of resveratrol-4'-O-β-D-glucuronide and resveratrol-3-O-β-D-glucuronide were 0.194±0.001 mM (equivalent to 78.381±0.366 mg/L) and 0.037±0.001 mM (equivalent to 14.991±0.248 mg/L) from a total of 0.5 mM (equivalent to 114.125 mg/L) of resveratrol in 3 hours at 40° C. in 200 mM phosphate buffer (pH 6.5) with shaking at 250 rpm.

Polyphenols are a large group of structurally diverse bioactive molecules. Many natural products from this group, such as resveratrol, quercetin, and curcumin, have promising biological activities. These molecules are available from certain foods and are consumed as dietary supplements (Sauer and Plauth 2017). However, their health benefits in the human body are often limited due to poor water solubility. Glycosylation is an effective approach to improve the water solubility and bioavailability. Actinomycetes are well-known for their ability to biosynthesize novel and pharmaceutically beneficial secondary metabolites with various bioactivities (Fidan et al. 2019). Among them, *Streptomyces* is widely used to produce industrially important bioactive molecules, such as oxytetracycline (Yu et al. 2013a). *S. chromofuscus* ATCC 49982 is a typical example which produces the anti-cholesterol polyketide natural product herboxidiene (Yu et al. 2013b). In this study, five actinomycete strains were screened for the ability to biotransform resveratrol, and only *S. chromofuscus* ATCC 49982 was found to generate two glycosides, which were structurally characterized as resveratrol-3-O-β-D-glucuronide and resveratrol-4'-O-β-D-glucuronide, respectively. Resveratrol is a plant-derived stilbenoid with a variety of bioactivities, including antimicrobial, antiviral, anti-inflammatory, antioxidant, antiaging, anticancer, antiplatelet, phytoestrogenic, neuro-protective, and cardio-protective activities (Thuan et al. 2018; Yu et al. 2002). Its ubiquitous presence in diets such as grapes, wine, olive oil, white tea, peanuts and cranberries has attracted considerable research interest (Pervaiz 2003; Wang et al. 2002). Nevertheless, its low bioavailability results in limited absorption after oral administration and impedes the formulation of functional foods. Furthermore, its sensitivity to air and light also hinders the nutraceutical and medicinal applications and exploitation of resveratrol (Francioso et al. 2014; Jeon et al. 2016; Uesugi et al. 2017).

Resveratroloside (resveratrol-4'-O-β-D-glucoside) and polydatin (resveratrol-3-O-β-D-glucoside) are two common water-soluble derivatives of resveratrol, and they exhibit anticancer and antioxidant activities. Moreover, they can prevent coronary heart diseases (Shimoda et al. 2013). In the meantime, resveratroloside and polydatin are more resistant to enzymatic oxidation than resveratrol (King et al. 2006). In other words, glycosylation of resveratrol can extend its half-life in the cell and maintains the beneficial antioxidant capacity and biological properties (Regev-Shoshani et al. 2003). As one of the most abundant forms of resveratrol in nature, polydatin is the major bioactive compound of Polygonum cuspidatum root which is used to treat cardiac ailments, including atherosclerosis and inflammation in Japanese and Chinese folk medicine (Romero-Pérez et al. 1999). While the two resveratrol glucuronides obtained in this work are structurally slightly different than those of glucosides, it will be interesting to find out how these molecules perform in vivo. In fact, resveratrol-3-O-β-D-glucuronide and resveratrol-4'-O-β-D-glucuronide were previously reported to be the metabolites of resveratrol in the human body. While resveratrol has cytotoxicity to human peripheral blood mononuclear cells at 30 μM, these glucuronides did not show any cytotoxicity at 300 μM. The ubiquitous human β-glucuronidase can convert the metabolites back to resveratrol locally or systematically in vivo (Wang et al. 2004). Therefore, the two resveratrol glucuronides may represent useful pro-drugs of resveratrol for clinical applications.

*S. chromofuscus* ATCC 49982 was also found to be able to glucuronidate other phenolic compounds including quercetin, vanillic acid, and ferulic acid. Two products, namely quercetin-7-O-β-D-glucuronide and quercetin-3-O-β-D-glucuronide, were obtained from quercetin. This result indicated that the dedicated UGT in this strain is flexible and can transfer the glucuronic acid moiety to different positions of quercetin. Ferulic acid-4-O-β-D-glucuronide was generated from ferulic acid by *S. chromofuscus* ATCC 49982. Interestingly, vanillic acid-4-O-β-D-glucuronide and vanillic acid-7-O-β-D-glucuronide were synthesized when vanillic acid is used as the substrate. The production of vanillic acid-7-O-β-D-glucuronide is somewhat surprising as the sugar moiety was introduced to the carboxyl group, which is quite chemically different than the phenolic hydroxyl group, further indicating that the UGT in *S. chromofuscus* ATCC 49982 is a highly versatile enzyme.

Encouraged by the high flexibility of this enzyme, we sought to find and identify the dedicated the UGT in *S. chromofuscus* ATCC 49982. While there are many glycosyltransferase genes in the genome, we were able to spot the most possible glycosyltransferase responsible for the observed glucuronidation in this strain because that it is flanked by two UDP-glucuronic acid biosynthetic genes (gcaD and gcaB), which encode UDP-glucose pyrophosphorylase and UDP-glucose dehydrogenase, respectively (Table 2). These two enzymes convert cellular glucose-1-phosphate to UDP-glucuronic acid (FIG. 4B). This makes GcaC a strong candidate of the dedicated UGT. This gene was cloned and expressed in *E. coli* BL21(DE3). The purified GcaC was functionally characterized as a UGT as it generated resveratrol-3-O-β-D-glucuronide and resveratrol-4'-O-β-D-glucuronide from resveratrol in the presence of UDP-glucuronic acid. This represents the first UGT fully characterized from microorganisms, providing a reference enzyme for future investigatin of more microbial UGTs.

UGTs play important roles in plant growth and development. They can also be a useful tool for structural modification of bioactive molecules in metabolic engineering applications, because it can greatly change the bioactivity, solubility, or stability of metabolites (De Bruyn et al. 2015; Kren and Martínková 2001). For example, the sweetness and solubility were greatly improved from glycyrrhetinic acid to its final product glycyrrhizin by two-step glucuronosylation, which is used as an anti-hepatitis agent and a sweetener worldwide (Xu et al. 2016). In fact, the two glucuronic acid moieties of glycyrrhizin also reduce the side-effects (Yonekura and Hanada 2011). Researchers found that glucuronidated anthocyanins showed improved color stability in response to light compared to its glucosylated form, indicating that UGTs may be used to stabilize natural colorants for industrial use, such as commercial food colorant products (Osmani et al. 2009). Glucuronidation can also improve the bioactivity of natural products. For instance, glucuronidated flavonoids exhibited relatively stronger inhibitory activity of amyloid ($\beta$(A($\beta$) and human islet amyloid polypeptide (hIAPP) aggregation than their aglycons (Hmidene et al. 2017). More importantly, the conjugation location of glucuronidation can alter the biological effects. Morphine-6-glucuronide is a much more potent agonist than morphine itself, while morphine-3-glucuronide is an extremely potent antagonist (Paul et al. 1989; Smith et al. 1990). This finding indicates that glucuronides may have very distinctive effects themselves.

To explore the pential of GcaC as a useful biocatalytic tool, we investigated the substrate specificity of this enzyme. Although the BLAST analysis suggested that GcaC is homologous to a possible UDP-glucosyltransferase/UDP-glucuronyltransferase from S. malaysiensis, our in vitro reaction results revealed that GcaC is a specific UDP-glucuronyltransferase, as it cannot take UDP-glucose as a sugar donor. By contrast, GcaC has showed high flexibilty toward the sugar acceptor substrates. A varitey of substrates, such as quercetin, ferulic acid, vanillic acid, curcumin, vanillin, chrysin, zearalenone and apigenin, can be accepted by GcaC as sugar acceptors to yield various glucuronides. Compared to BpUGAT from plant red daisy (*Bellis perennis*) that is specific for anthocyanin glucuronidation (Sawada et al. 2005), GcaC showed relaxed substrate specificity to sugar acceptors. Interestingly, it was found that different products may be produced from the same substrates in the in vivo biotransformation by *S. chromofuscus* ATCC 49982 and in vitro reactions with purified GcaC, likely due to the availability of UDP-glucuronic acid and other factors in the cells. For example, quercetin-7-O-$\beta$-D-glucuronide and quercetin-3-O-$\beta$-D-glucuronide were obtained as the major products when quercetin was incubated with *S. chromofuscus* ATCC 49982. However, a total of six glucuronides were detected when quercetin was reacted with UDP-glucuronic acid in the presence of purified GcaC. Interestingly, among the six products, four monoglucuronides and two diglucuronides of quercetin were obtained based on LC-MS analysis. Quercetin has five free hydroxyl groups. In addition to the 3-OH and 7-OH, two other hydroxyl groups were chosen by GcaC to introduce the sugar moiety. More interestingly, GcaC appeared to be able to introduce two glucuronic acid moieties to quercetin to create diglucuronides. Similarly, in vitro reaction of GcaC with curcumin also yielded a monoglucuronide and a diglucuronide. These results indicated that GcaC is a highly versatile enzyme for the synthesis of glucuronides. Compared to the tedious chemical methods to synthesize glucuronides (Sharipova et al. 2017), discovery of GcaC provides an effective tool to prepare various glucuronides from different phenolic compounds in an environmental-friendly and efficient way.

The optimal in vitro enzymatic reactions and in vivo bioconversion conditions of GcaC were investigated in this work. The optimum reaction temperature and pH for this enzyme were found to be 7.5 and 30° C. in phosphate buffer, which are both slightly lower than BpUGAT from *B. perennis* (8.0 and 35° C.). However, these two UGTs have different response to metal ions. For example, $Ca^{2+}$ had an inhibitory effect on BpUGAT, but stimulated the activity of GcaC. Similarly, $Mg^{2+}$ and $Mn^{2+}$, with negligible effects on the catalytic activity of BpUGAT (Sawada et al. 2005), enhanced the activity of GcaC. By contrast, the inhibitory effects of $Cu^{2+}$, $Zn^{2+}$ and $Fe^{2+}$ on GcaC is similar to the previous discovered UBGAT from *Scutellaria baicalensis* (Nagashima et al. 2000).

GcaC represents the first characterized UGT from microorganisms. BLAST analysis showed that this microbial UGT showed little or no homology to UGTs from other sources. For example, GcaC has less than 25% identity to BpUGAT from *B. perennis* (Gene bank accession number AB190262) (Sawada et al. 2005), GuUGAT from *Glycyrrhiza uralensis* (Gene bank accession number KT759000) (Xu et al. 2016), and UBGAT from *Scutellaria baicalensis* (Gene bank accession number BAC98300) (Nagashima et al. 2000). Discovery and characterization of GcaC yielded a reference enzyme for future identification of additional UGTs from microorganisms. More importantly, this highly flexible enzyme may (1) glucuronidate a variety of substrates, (2) introduce the glucuronic acid moiety to different positions of a substrate, and (3) introduce one or two glucuronic acid moieties to a substrate to yield monoglucosides and diglucosides. Therefore, *S. chromofuscus* ATCC 49982, GcaC and *E. coli* BL21(DE3)/GcaC can be used to prepare desired glucuronides from particular substrates. For example, vanillic acid-COOH-glucuronide was only previously detected in human urine after tea intake, and it was only identified by using MS analysis without available NMR data (Ridder et al. 2012; van der Hooft et al. 2012). This work for the first time biosynthesized vanillic acid-7-O-$\beta$-D-glucuronide for complete structure elucidation. This work also demonstrated that this novel UGT can be efficiently expressed in *E. coli* BL21(DE3) and the engineered strain can be used as a whole-cell biocatalyst to prepare resveratrol glucuronides. The titers of resveratrol-4'-O-$\beta$-D-glucuronide and resveratrol-3-O-$\beta$-D-glucuronide were 78.381±0.366 mg/L and 14.991±0.248 mg/L from 114.125 mg/L resveratrol in a 1-L reaction system within 3 hours. Overall, this work provides a highly versatile UGT that can serve as a useful biocatalyst to prepare valuable glucuronides of bioactive molecules.

Figure 9:
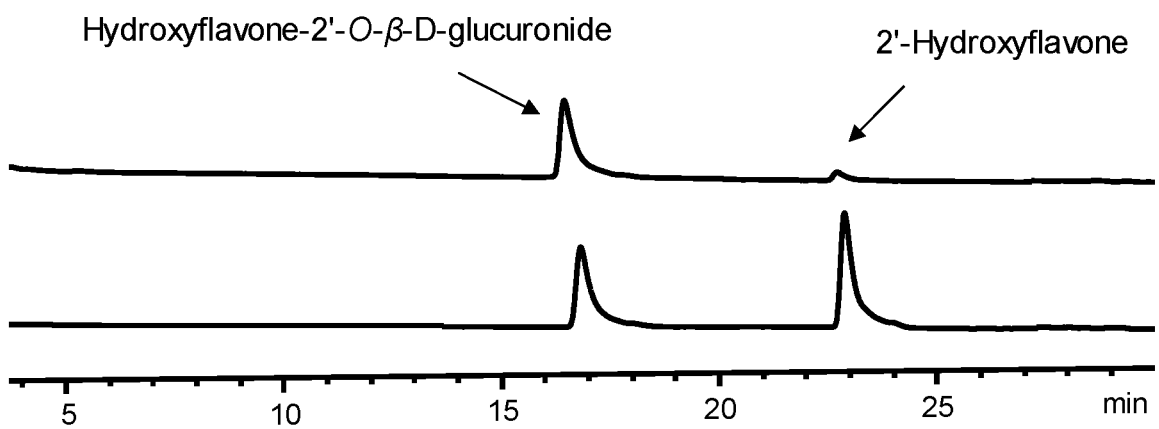
FIG. 9 shows HPLC analysis of glucuronidation of 2'-hydroxyflavone at 300 nm. Top: *E. coli*-GcaC+2'-hydroxyflavone; Bottom: *S. chromofuscus* ATCC 49982+2'-hydroxyflavone.

Example 11. Hydroxyflavone-2'-O-$\beta$-D-glucuronide was Prepared from 2'-hydroxyflavone by Incubation of the Substrate with *S. chromofuscus* ATCC 49982 or the Engineered *E. coli*-GcaC Hydroxyflavone-2'-O-$\beta$-D-glucuronide was prepared from 2'-hydroxyflavone by incubation of the substrate with *S. chromofuscus* ATCC 49982 or the engineered *E. coli*-GcaC as described above. The HPLC analysis results are shown in FIG. 9.

Figure 10:
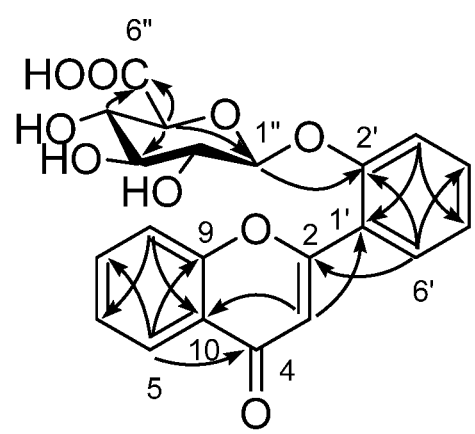
FIG. 10 shows HMBC correlations for hydroxyflavone-2'-O-β-D-glucuronide.

The product was isolated from the cultures as a white, amorphous powder using HPLC. Its molecular formula was deduced to be $C_{21}H_{18}O_9$ based on the $[M-H]^+$ peak at m/z 415.1013 (415.1029 calcd for $C_{21}H_{19}O_9$) in high-resolution electrospray ionization mass spectrometry (HRESIMS) spectrum, indicating that this compound has thirteen degrees of unsaturation. To further elucidate the chemical structure, this product was analyzed by NMR. The $^{13}C$ NMR analysis presented 21 peaks in the spectrum. In addition to the 15 signals belonging to the substrate, six additional carbon signals at $\delta_C$ 170.0, 99.6, 76.0, 75.5, 73.0, and 71.3 were found in the spectra, together with the additional proton signals at $\delta_H$ 3.34-3.98 in the $^1$H NMR spectrum, suggesting that a sugar moiety has been added to 2'-hydroxyflavone. Unlike the common sugar glucose, this sugar moiety has a quaternary carbon signal at $\delta_C$ 170.0, indicating the presence of a carboxyl group in the sugar moiety. Therefore, both the $^1$H and $^{13}$C signals of this sugar moiety are consistent with a glucuronic acid moiety. Moreover, the $^1$H NMR spectrum showed a doublet at $\delta_H$ 5.32, indicative of an anomeric proton with a coupling constant of 7.2 Hz, and the chemical shift along with the J-coupling value were consistent with that of β-D-glucuronic acid. The correlation of the anomeric H-1" signal at $\delta_H$ 5.55 to C-2' signal at $\delta_C$ 154.0 in the HMBC spectrum revealed that the glucuronic acid moiety was located at C-2' (FIG. 10). The above data together with the detailed analysis of its 2D NMR spectra confirmed its structure as hydroxyflavone-2'-O-β-D-glucuronide and all signals were assigned accordingly (Table 5).

TABLE 5

$^1$H (500 MHz) and $^{13}$C NMR (125 MHz) data for hydroxyflavone-2'-0-D-glucuronide in DMSO-d$_6$.

| | Hydroxyflavone-2'-O-β-D-glucuronide | |
|---|---|---|
| Position | $\delta_C$, type | $\delta_H$ (J in Hz) |
| 2 | 160.7, C | |
| 3 | 112.2, CH | 7.04 (1H, s) |
| 4 | 177.2, C | |
| 5 | 124.7, CH | 8.06 (1H, dd, J = 7.9, 1.5 Hz) |
| 6 | 125.4, CH | 7.50 (1H, t, J = 7.5 Hz) |
| 7 | 134.2, CH | 7.82 (1H, m) |
| 8 | 118.6, CH | 7.74 (1H, d, J = 8.3 Hz) |
| 9 | 156.0, C | |
| 10 | 123.2, C | |
| 1' | 121.0, C | |
| 2' | 154.9, C | |
| 3' | 115.3, CH | 7.37 (1H, d, J = 8.5Hz) |
| 4' | 132.7, CH | 7.57 (1H, m) |
| 5' | 122.2, CH | 7.23 (1H, t, J = 7.6 Hz) |
| 6' | 129.4, CH | 7.93 (1H, dd, J = 7.8, 1.5 Hz) |
| 1" | 99.6, CH | 5.32 (1H, d, J = 7.2 Hz) |
| 2" | 73.0, CH | 3.34 (2H, m, overlapped) |
| 3" | 76.0, CH | 3.34 (2H, m, overlapped) |
| 4" | 71.3, CH | 3.42 (1H, m) |
| 5" | 75.5, CH | 3.98 (1H, d, J = 9.6 Hz) |
| 6" | 170.0, C | |

Hydroxyflavone-2'-O-β-D-glucuronide: White, amorphous powder; UVmax 247, 308 nm; IR vmax (film) 3242.9, 2985.9, 1614.8, 1556.0, 1468.1, 1379.7, 1216.3, 1088.8 cm$^{-1}$; $^1$H and $^{13}$C NMR data, see Table 5; negative ESIMS m/z 412.8 [M-H]$^-$; positive HRESIMS m/z 415.1013 [M-H]$^+$ (415.1029 calcd for $C_{21}H_{19}O_9$).

Determination of the Water-Solubility

The purified product was tested for their water solubility as previously described (Wang et al. 2014). Purified 2'-hydroxyflavone glycoside was used to establish standard curves for quantifying water solubility. Briefly, the purified compound and the substrate were each mixed with 300 μL of distilled water in an Eppendorf tube at 25° C. An ultrasonic cleaner was used to facilitate the dissolution. After 30 min of sonication and centrifugation at 13,000×g for 10 min, supernatant of each sample was analyzed by HPLC to determine the compound concentrations in the solution. All samples were performed in triplicate and water solubility of each sample are expressed as the mean±standard deviation (SD).

The water solubility of hydroxyflavone-2'-O-β-D-glucuronide was computed in triplicate (n=3) and determined to be 34.8±0.9 mg/L, which is around 14 times than that of the substrate 2'-hydroxyflavone (2.5±0.7 mg/L). This result demonstrated that the glucuronidation technology in this invention is an effective approach to enhancing the water solubility.

Antioxidant Assay

The DPPH radical scavenging assay was performed to evaluate the antioxidant activity of all four new compounds using a reported method with minor modifications (Jiao et al. 2015. Briefly, 180 μt of 150 μM fresh DPPH in MeOH were mixed with 20 μL of sample at different concentrations (62.5, 125, 250, 500, and 1000 μM in DMSO) in the wells of 96-well plates. The natural antioxidant ascorbic acid and the substrate 2'-hydroxyflavone were used as the positive and negative controls, respectively. After shaking in the dark for 30 min at room temperature, the reaction was detected by measuring the absorbance $A_{sample+DPPH}$ at 517 nm using a microplate reader. $A_{sample}$ means the blank measurement for each tested compound; specifically, 20 μL of sample was mixed with 180 μL of MeOH. $A_{DPPH}$ is the absorbance of the mixture of 20 μL of distilled water and 180 μL of DPPH. $A_{blank}$ indicates the absorbance of the mixture of 20 μL of distilled water and 180 μL of MeOH. All tests were performed in triplicate. The formula DPPH scavenging activity (%)=[1−($A_{sample+DPPH}$−$A_{sample}$)/($A_{DPPH}$−$A_{blank}$)]×100%. The logIC$_{50}$ values (the concentration required to scavenge 50% of radicals)] of tested compounds were calculated using the GraphPad Prism software. The results are expressed as the mean±SD. Significant differences were determined by one-way analysis of variance (ANOVA) using the SAS Studio web-based environment, and p<0.05 was considered significant. All samples were performed in triplicate and antioxidant activity of each sample is expressed as the mean±SD.

The resulting pairwise comparison analysis demonstrated that hydroxyflavone-2'-O-β-D-glucuronide has significantly improved radical scavenging activity, decreasing the mean logIC$_{50}$ from 65.2±8.6 μM (2'-Hydroxyflavone) to 20.4±0.7 μM (p<0.001). This result confirmed that the glucuronidation technology described in this invention can effectively enhance the biological activity of bioactive molecules.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Almeida A F, Santos Cu N, Ventura M R (2017) Synthesis of new sulfated and glucuronated metabolites of dietary phenolic compounds identified in human biological samples. J Agric Food Chem 65 (31):6460-6466.

Bowles D, Isayenkova J, Lim E-K, Poppenberger B (2005) Glycosyltransferases: managers of small molecules. Curr Opin Plant Biol 8 (3):254-263.

Briggs B, Baker P, Belvo M, Black T, Getman B, Kemp C, Muth W, Perun T, Strobel Jr R, Paschal J (1999) Microbial process for preparation of glucuronides of raloxifene. J Ind Microbiol Biot 23 (3):194-197.

Cai Z, Huang J, Luo H, Lei X, Yang Z, Mai Y, Liu Z (2013) Role of glucose transporters in the intestinal absorption of gastrodin, a highly water-soluble drug with good oral bioavailability. J Drug Target 21 (6):574-580.

Cassinelli G, Ballabio M, Grein A, Merli S, Rivola G, Arcamone F, Barbieri B, Bordoni T (1987) A new class of biosynthetic anthracyclines: anthracyclinone glucuronides. J Antibiot 40 (7): 1071-1074.

Chung S, Seki H, Fujisawa Y, Shimoda Y, Hiraga S, Nomura Y, Saito K, Ishimoto M, Muranaka T (2020) A cellulose synthase-derived enzyme catalyses 3-O-glucuronosylation in saponin biosynthesis. Nat Commun 11 (1):1-11.

De Bruyn F, Maertens J, Beauprez J, Soetaert W, De Mey M (2015) Biotechnological advances in UDP-sugar based glycosylation of small molecules. Biotechnol Adv 33 (2):288-302.

De Wildt S N, Kearns G L, Leeder J S, van den Anker J N (1999) Glucuronidation in humans. Clin Pharmacokinet 36 (6):439-452.

Engstrom K M, Daanen J F, Wagaw S, Stewart A O (2006) Gram scale synthesis of the glucuronide metabolite of ABT-724. J Org Chem 71 (22):8378-8383.

Fidan O, Yan R, Zhu D, Zhan J (2019) Improved production of antifungal angucycline Sch47554 by manipulating three regulatory genes in Streptomyces sp. SCC-2136. Appl Biochem Biotechnol 66 (4):517-526.

Francioso A, Mastromarino P, Restignoli R, Boffi A, d'Erme M, Mosca L (2014) Improved stability of trans-resveratrol in aqueous solutions by carboxymethylated (1,3/1,6)-β-D-glucan. J Agric Food Chem 62 (7):1520-1525.

Gachon C M, Langlois-Meurinne M, Saindrenan P (2005) Plant secondary metabolism glycosyltransferases: the emerging functional analysis. Trends Plant Sci 10 (11):542-549.

Harbome J B, Baxter H (1999) The handbook of natural flavonoids. Volume 1 and Volume 2. John Wiley and Sons.

Hmidene A B, Hanaki M, Murakami K, Irie K, Isoda H, Shigemori H (2017) Inhibitory activities of antioxidant flavonoids from Tamarix gallica on amyloid aggregation related to Alzheimer's and type 2 diabetes diseases. Biol Pharm Bull 40 (2):238-241.

Imai H, Kitagawa M, Ishihara K, Masuoka N, Shimoda K, Nakajima N, Hamada H (2012) Glycosylation of trans-resveratrol by plant-cultured cells. Biosci Biotech Bioch 76 (8):1552-1554.

Jeon Y O, Lee J-S, Lee H G (2016) Improving solubility, stability, and cellular uptake of resveratrol by nanoencapsulation with chitosan and γ-poly (glutamic acid). Colloids Surf B 147:224-233.

Jiao Z-Z, Yue S, Sun H-X, Jin T-Y, Wang H-N, Zhu R-X, Xiang L (2015) Indoline amide glucosides from Portulaca oleracea: isolation, structure, and DPPH radical scavenging activity, J Nat Prod 78:2588-2597.

Kaminaga Y, Nagatsu A, Akiyama T, Sugimoto N, Yamazaki T, Maitani T, Mizukami H (2003) Production of unnatural glucosides of curcumin with drastically enhanced water solubility by cell suspension cultures of Catharanthus roseus. FEBS Lett 555 (2):311-316.

Kim S-K (2016) Marine Enzymes Biotechnology: Production and Industrial Applications, Part II-Marine Organisms Producing Enzymes, Volume 79, $1^{st}$ edition. Academic Press.

King R E, Bomser J A, Min D B (2006) Bioactivity of resveratrol. Compr Rev Food Sci F 5 (3): 65-70.

Kren V, Martinková L (2001) Glycosides in medicine: "The role of glycosidic residue in biological activity". Curr Med Chem 8 (11):1303-1328.

Li Y, Baldauf S, Lim E-K, Bowles D J (2001) Phylogenetic analysis of the UDP-glycosyltransferase multigene family of Arabidopsis thaliana. J Biol Chem 276 (6):4338-4343.

Marvalin C, Azerad R (2011a) Microbial glucuronidation of polyphenols. J Mol Catal B Enzym 73 (1-4):43-52.

Marvalin C, Azerad R (2011b) Microbial production of phase I and phase II metabolites of propranolol. Xenobiotica 41 (3):175-186.

Mehnaz D, Abdulla K, Aiysha D, Zaheer A, Mukhtar S (2017) Actinomycetes: a source of industrially important enzymes. J Proteom Bioinform 10:12

Nagashima S, Hirotani M, Yoshikawa T (2000) Purification and characterization of UDP-glucuronate: baicalein 7-O-glucuronosyltransferase from Scutellaria baicalensis Georgi. cell suspension cultures. Phytochemistry 53 (5): 533-538.

Nawani N, Aigle B, Mandal A, Bodas M, Ghorbel S, Prakash D (2013) Actinomycetes: Role in biotechnology and medicine. BioMed Res Int 2013: 687190.

Osmani S A, Halkjær Hansen E, Malien-Aubert C, Olsen C-E, Bak S, Lindberg Moller B (2009) Effect of glucuronosylation on anthocyanin color stability. J Agric Food Chem 57 (8):3149-3155.

Pandey R P, Parajuli P, Shin J Y, Lee J, Lee S, Hong Y-S, Park Y I, Kim J S, Sohng J K (2014) Enzymatic biosynthesis of novel resveratrol glucoside and glycoside derivatives. Appl Environ Microbiol 80 (23):7235-7243.

Paul D, Standifer K M, Inturrisi C E, Pasternak G (1989) Pharmacological characterization of morphine-6 β-glucuronide, a very potent morphine metabolite. J Pharmacol Exp Ther 251 (2):477-483.

Pervaiz S (2003) Resveratrol: from grapevines to mammalian biology. FASEB J 17 (14):1975-1985.

Prakash D, Nawani N, Prakash M, Bodas M, Mandal A, Khetmalas M, Kapadnis B (2013) Actinomycetes: a repertory of green catalysts with a potential revenue resource. Biomed Res Int 2013:264020.

Priyadharsini P, Dhanasekaran D (2015) Diversity of soil allelopathic Actinobacteria in Tiruchirappalli district, Tamilnadu, India. J Saudi Soc Agric Sci 14 (1):54-60.

Regev-Shoshani G, Shoseyov O, Bilkis I, Kerem Z (2003) Glycosylation of resveratrol protects it from enzymic oxidation. Biochem J 374 (1):157-163.

Remya M, Vijayakumar R (2008) Isolation and characterization of marine antagonistic actinomycetes from west coast of India. Med Biol 15 (1):13-19.

Rice-Evans C (2001) Flavonoid antioxidants. Curr Med Chem 8 (7):797-807.

Ridder L, van der Hooft J J, Verhoeven S, de Vos R C, van Schaik R, Vervoort J (2012) Substructure-based annotation of high-resolution multistage MSn spectral trees. Rapid Commun Mass Sp 26 (20):2461-2471.

Romero-Pérez A I, Ibern-Gómez M, Lamuela-Raventós R M, de la Torre-Boronat M C (1999) Piceid, the major resveratrol derivative in grape juices. J Agric Food Chem 47 (4):1533-1536.
Sauer S, Plauth A (2017) Health-beneficial nutraceuticals-myth or reality? Appl Microbiol Biotechnol 101 (3):951-961.
Sawada Sy, Suzuki H, Ichimaida F, Yamaguchi M-a, Iwashita T, Fukui Y, Hemmi H, Nishino T, Nakayama T (2005) UDP-glucuronic acid: anthocyanin glucuronosyltransferase from red daisy (*Bellis perennis*) flowers: enzymology and phylogenetics of a novel glucuronosyltransferase involved in flower pigment biosynthesis. J Biol Chem 280 (2):899-906.
Sharipova R, Andreeva O, Strobykina I Y, Voloshina A, Strobykina A, Kataev V (2017) Synthesis and antimicrobial activity of glucuronosyl derivatives of steviolbioside from *Stevia rebaudiana*. Chem Nat Compd 53 (6): 1107-1111.
Shimoda K, Hamada M, Hamada H, Takemoto M, Hamada H (2013) Synthesis of resveratrol glycosides by cultured plant cells. Nat Prod Commun 8 (7):907-909.
Smith M T, Watt J A, Cramond T (1990) Morphine-3-glucuronide-a potent antagonist of morphine analgesia. Life Sci 47 (6):579-585.
Stachulski A, Jenkins G (1998) The synthesis of O-glucuronides. Nat Prod Rep 15 (2):173-186.
Stachulski A V, Harding J R, Lindon J C, Maggs J L, Park B K, Wilson I D (2006) Acyl glucuronides: biological activity, chemical reactivity, and chemical synthesis. J Med Chem 49 (24): 6931-6945.
Thilakarathna S H, Rupasinghe H (2013) Flavonoid bioavailability and attempts for bioavailability enhancement. Nutrients 5 (9):3367-3387.
Thorson J S, Barton W A, Hoffmeister D, Albermann C, Nikolov D B (2004) Structure-based enzyme engineering and its impact on in vitro glycorandomization. ChemBioChem 5 (1):16-25.
Thuan N H, Trung N T, Cuong N X, Van Cuong D, Van Quyen D, Malla S (2018) *Escherichia coli* modular coculture system for resveratrol glucosides production. World J Microb Biot 34 (6):1-13.
Tsao R (2010) Chemistry and biochemistry of dietary polyphenols. Nutrients 2 (12):1231-1246.
Uesugi D, Hamada H, Shimoda K, Kubota N, Ozaki S-i, Nagatani N (2017) Synthesis, oxygen radical absorbance capacity, and tyrosinase inhibitory activity of glycosides of resveratrol, pterostilbene, and pinostilbene. Biosci Biotechnol Biochem 81 (2):226-230.
Van der Hooft J J, de Vos R C, Mihaleva V, Bino RJ, Ridder L, de Roo N, Jacobs D M, van Duynhoven J P, Vervoort J (2012) Structural elucidation and quantification of phenolic conjugates present in human urine after tea intake. Anal Chem 84 (16):7263-7271.
Wang L-X, Heredia A, Song H, Zhang Z, Yu B, Davis C, Redfield R (2004) Resveratrol glucuronides as the metabolites of resveratrol in humans: characterization, synthesis, and anti-HIV activity. J Pharm Sci 93 (10):2448-2457.
Wang, S., Liu, G., Zhang W., Cai, N., Cheng C., Ji Y., Sun L., Zhan, J., Yuan, S., Efficient glycosylation of puerarin by an organic solvent-tolerant strain of *Lysinibacillus fusiformis*, Enzyme Microb. Technol. 57 (2014) 42-47).
Wang Y, Catana F, Yang Y, Roderick R, Van Breemen R (2002) Analysis of resveratrol in grape products, cranberry juice and wine using liquid chromatography-mass spectrometry. J Agric Food Chem 50:431-435.
Weymouth-Wilson A C (1997) The role of carbohydrates in biologically active natural products. Nat Prod Rep 14 (2): 99-110.
Wilkinson S M, Liew C W, Mackay J P, Salleh H M, Withers S G, McLeod M D (2008) *Escherichia coli* glucuronylsynthase: an engineered enzyme for the synthesis of β-glucuronides. Org Lett 10 (8):1585-1588.
Wilkinson S M, Watson M A, Willis A C, McLeod M D (2011) Experimental and kinetic studies of the *Escherichia coli* glucuronylsynthase: An engineered enzyme for the synthesis of glucuronide conjugates. J Org Chem 76 (7): 1992-2000.
Xu G, Cai W, Gao W, Liu C (2016) A novel glucuronosyltransferase has an unprecedented ability to catalyse continuous two-step glucuronosylation of glycyrrhetinic acid to yield glycyrrhizin. New Phytol 212 (1):123-135.
Yonekura K, Hanada K (2011) An evolutionary view of functional diversity in family 1 glycosyltransferases. Plant J 66 (1):182-193.
Yu C, Shin YG, Chow A, Li Y, Kosmeder J W, Lee Y S, Hirschelman W H, Pezzuto J M, Mehta R G, van Breemen R B (2002) Human, rat, and mouse metabolism of resveratrol. Pharm Res 19 (12): 1907-1914.
Yu D, Xu F, Valiente J, Wang S, Zhan J (2013a) An indigoidine biosynthetic gene cluster from *Streptomyces chromofuscus* ATCC 49982 contains an unusual IndB homologue. J Ind Microbiol Biot 40 (1):159-168.
Yu D, Xu F, Zhang S, Shao L, Wang S, Zhan J (2013b) Characterization of a methyltransferase involved in herboxidiene biosynthesis. Bioorg Med Chem Lett 23 (20):5667-5670.

---

What is claimed is:

1. A process for producing a glucuronide from UDP-glucuronic acid and a phenolic compound that comprises a hydroxyl or a carboxyl group, wherein said glucuronide comprises a glucuronic acid moiety bound to the hydroxyl or the carboxyl group of said phenolic compound, wherein said process comprises the steps of:
  (i) culturing a genetically modified microorganism in a medium that comprises the phenolic compound, wherein the genetically modified microorganism expresses a UDP-glucuronyltransferase (UGT) that comprises the amino acid sequence of SEQ ID NO:7 or an amino acid sequence at least 95% identical to SEQ ID NO:7, under conditions allowing the genetically modified microorganism to produce the glucuronide; and
  (ii) optionally recovering the glucuronide from the medium.

2. The process of claim 1, wherein the genetically modified microorganism expresses a UDP-glucose dehydrogenase that comprises SEQ ID NO: 6 and a UDP-glucose pyrophosphorylase that comprises SEQ ID NO:8.

3. The process of claim 1, wherein the genetically modified microorganism has been transformed to express (i) a nucleic acid that encodes a UDP-glucose dehydrogenase having at least 95% sequence identity to the polypeptide of SEQ ID NO: 6, and/or (ii) a nucleic acid that encodes a UDP-glucose pyrophosphorylase having at least 95% sequence identity to the polypeptide of SEQ ID NO: 8.

4. The process of claim 1, wherein the genetically modified microorganism is selected from the group consisting of bacteria, yeast, filamentous fungi, and microalgae.

5. The process of claim 4, wherein the genetically modified microorganism is selected from the group consisting of *Aspergillus, Trichoderma, Saccharomyces, Pichia, Phaffia, Candida, Hansenula, Salmonella, Bacillus, Acinectorhacter, Zymomonas, Agrobacterium, Erythrobacter, Chloroborium, Chlorella, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Syn-*

*echocystis, Methanomonas, Synechococcus, Anabeana, Thiobacillus, Methanobacterium, Klebsiella,* and *Myxococcus.*

6. The process of claim 1, wherein the phenolic compound is selected from the group consisting of resveratrol, quercetin, ferulic acid, vanillic acid, curcumin, vanillin, chrysin, zearalenone, apigenin, doxorubicin, etoposide, morphine, ezetimibe, 2'-hydroxyflavone, and combinations thereof.

7. The process of claim 1, wherein the phenolic compound is at a concentration of between 0.25 mM and 0.75 mM.

8. The process of claim 1, wherein (a) the medium in maintained at a pH of between 5.5 and 7.5, (b) the medium is maintained at a temperature of between 35° C. and 45° C.; and/or (c) the genetically modified microorganism is cultured in the medium for a period of 2.5 hours and 3.5 hours prior to recovering the glucuronide from the medium.

9. The process of claim 1, wherein the genetically modified microorganism has been transformed to express a UGT that comprises SEQ ID NO: 7.

10. The process of claim 9, wherein the genetically modified microorganism has been transformed to express a UDP-glucose dehydrogenase that comprises SEQ ID NO: 6.

11. The process of claim 10, wherein the genetically modified microorganism has been transformed to express a UDP-glucose pyrophosphorylase that comprises SEQ ID NO: 8.

* * * * *

SEQUENCE LISTING

```
Sequence total quantity: 8
SEQ ID NO: 1            moltype = DNA  length = 35
FEATURE                 Location/Qualifiers
misc_feature            1..35
                        note = primer
source                  1..35
                        mol_type = other DNA
                        organism = synthetic construct
SEQUENCE: 1
aattgtttaa accatatgcg agtactgttc accac                               35

SEQ ID NO: 2            moltype = DNA  length = 37
FEATURE                 Location/Qualifiers
misc_feature            1..37
                        note = primer
source                  1..37
                        mol_type = other DNA
```

```
                        organism = synthetic construct
SEQUENCE: 2
aattgctagc aagctttcag acgatcttct gcaggtc                              37

SEQ ID NO: 3            moltype = DNA   length = 1455
FEATURE                 Location/Qualifiers
source                  1..1455
                        mol_type = genomic DNA
                        organism = Streptomyces chromofuscus
SEQUENCE: 3
atgcgggccg ttgatctccg acacccgccc tatgtgttca ggtccgacga cggcgtcgga    60
cctgttcccc tgctggtgat acggccgagg cgccggccct cggtgaggct gaaactcgaa   120
caagcggaat cggtgattct catgggactt cgacatataa ccgtcattgg aaccggctat   180
gtcggtctga ccaccggcgc ctgtctggcc tccctcggac accggtggt gtgcgcggat    240
gccgacgagg gcaaggtcga acggctccgg cgggcggagg tcgacatcct cgaaccgggc   300
cttacggaag tcgtccgcga ggggctggaa tccggccgtc tccagttcgt gagggacacc   360
cgggcggccg tcgaggaggc cgaggtcgtc ttcctctgcc tgcccacccc gatgggcgtc   420
ggaggcgccg ccgacctggc cgccgtcgag gcggtcgccg acgaggtccg cgaccgcctg   480
ccgcgtggct gcacggtggt caacaagtcc accgtgccgg tcgcaccgc cgagcgcgtc   540
gcggccctgc tcgccgcccc cgacgtgacc gtggtgagca cccgagtt cctccgcgag    600
ggacacgcgg tggacgactt cctccacccc gaccggatcg tggtgggcgc cgccgacgcg   660
gacgcgcgcg ggctggtggc cgacctgtac ctggacatcg acgcaccgcc cgtggtcacc   720
gacaccgccg cgcgccgaact cgccaagtac gccgcgaact tcttcctcgc gatgaagctg   780
tcgttcgcga caacctggc cacgctctgc gaaagtctcg gcgcgaacat cgacgacgtg    840
gtcgccggca tcgccacga cccacggatc ggcggcgcct tcctcaagcc cgggcccgga   900
tggggcggtt cctgcctgcc caaggacacg cacgcgctgc tgcgcgtctg cgaggagtca   960
ggcgtcgagt tccgctgct ccgggccacc atcgagacca acgtcgagca ccagcgccgg  1020
ctcgtcgagc gggtgaccgc cggatgcgcg ggggcggacg gttcactgcg cggcgtccgg  1080
atcgggctgc tcggtctcac cttcaaggcc ggcaccttcg acctgcgcga ctcgcccgcc  1140
ctcgccatcg cccgcctgct gcgggagcgg ggcgccgaac tgcgccgcta cgacccggcc  1200
ctcagcgagc tccgccccga cctcggcgat ctgctcacca tcaccggtac cccctcgaa   1260
gcggtcgacg gggcccgcgc ctgcgtcgta tcaccgagt ggccgcaatt ccgcgacctg   1320
gactgggagg ccgtcgccgg gcggctcgcc gcgccgctcg tctacgactt ccgtaacatc   1380
ctcgatccgg cacggctcga cagggccgcg ctgacctggg aaggcatcgg tcgttcgctg   1440
gcaatggcca gttga                                                   1455

SEQ ID NO: 4            moltype = DNA   length = 1209
FEATURE                 Location/Qualifiers
source                  1..1209
                        mol_type = genomic DNA
                        organism = Streptomyces chromofuscus
SEQUENCE: 4
gtgcgagtac tgttcaccac gctcggtagt ccctcccacg gtcgcgcaca gcttccgctg    60
gcccgggcgt tcgccgcggc cggacacgac gtcctcgtgg ccaccacccc gaccctcgcc   120
tccgtcttcg aacaggacga cgtccgggtg accgtctgca tgggcgattt cacgccacag   180
tccttcatca cccccgaact gctccaggag gcgatgcggc cgggtcagga cggtgagccg   240
caggacgcca tggcgcgcct catgcccgag atcacctccg gcccgatggc caggaagctg   300
tgggaagaga tccttccggt ggcgcggag ttcgcccccg acctcatcct gcgcgacggc   360
atggacctga gctcgtgcct gatcgcgaaa cacctcggca tcccgcaact gcccaccct    420
tcgggcacga acaacctcat cgaccccgcc atggtgctgc ccggcctgaa cgtcctgcgg   480
aaggaattcg ggctgtccgc ccaggaggac ccgctgtccc cccca cgggcgtcg         540
gactacgtac cggcggcctt ctcgttcgcc cagcacctgc cctcgtcgtg gtcctaccgg    600
cagaccgtga ccgtggaccg cagctcggtc ctgccggagt ggatcgccca actgcccacc   660
gaccgccccc tggtgttcgc cgcgctcggc accgccttc gatgatcag ggagatgggg    720
gccgaggcga ccgggccgtc gctgttcccg atgccggacc cggtggacac gctgcggttg   780
atgatcgagg cggtgtcgcg gtcgacgac tgcaccgtgg tcgtcgccac ctccggcatc   840
ccggcggaca ccgagggcct gccgccgcat gtgcacgtca ccgaccgggt gccgcagccc    900
ctgctgctgg agtccgtcga cgcgttcctc acccacggcg gcttcaacag catccggag   960
gcgctgcgca cggccacccc gatggcgtg ctgccccagt tcggcgacca gcccgccaac  1020
gcgcgccgcg tcgaggaact cggcctcggc cgggagatca cgacatccac cgcggacggc  1080
atcaccaagg ccgtacgcga ggtgctgacc gaccccggca tccgggccag gacgcggag   1140
gcccggctgg cgatgctggc gctgccggag atcgacagcg ccgtggccga cctgcagaag  1200
atcgtctga                                                          1209

SEQ ID NO: 5            moltype = DNA   length = 963
FEATURE                 Location/Qualifiers
source                  1..963
                        mol_type = genomic DNA
                        organism = Streptomyces chromofuscus
SEQUENCE: 5
atgtcgcctt cccgccccc tgccaccacc gtcaccaagg ccgtgatacc ggccgccggc    60
ctgggcaccc gcttcctccc ggcgacgaag gccatgccca aggagatgct gcccgtcgtc   120
gaccgcccgg ccatccagta cgtggtgaa gaggccgccg cgccggtct ctccgatctg    180
tcgtgatca ccgggcgaa caagccccg acttcgacca cgcctgggaa                 240
ctggaggagg ccctgacccg caagggcgac gagggcagge tgcgcagtgt ccgggagtcc   300
accgcgctcg ccgcgatcca ctacgtccgg cagggcaccc cggcgggcct cggacacgcc   360
gtgctctgcg cccaacagca cgtggggggac gagccgttcg ccgtactcct gggcgacgac   420
ctcatcgacc cgcgcgatcc actgctcacc cggatgatca agatacggga acggttcggc   480
ggcagcgtgg tcgcgctgat ggagaccgac ccccgcctcga tccacctgta cggctgcgcg  540
```

```
gcggtcgaac ccaccgcaca ggacgatgtc gtacgcctga ccgacctggt ggagaagccc  600
gccccggggc aagcccccag cgcgtacgcg gtcatcggac gctatctgct ggacccggcc  660
gtgttcgagg tgctgcgccg caccccgccc ggccacggcg gcgagatcca gctcaccgac  720
gccctgcgcg aactggcgca cggcggtgcc acctccccgg gcggcccggt ccacggcgtg  780
ctgttcaccg gacggcgcta cgacaccggc gaccgccgcg agtacctgcg caccatcgtc  840
cgactggcct acgaacacga cgacctcggc cccgggttcc gggagtggct gaccgcgttc  900
gtcgacgccg aacgcgaggc ccccaccgcg gcggccgacg gcggcccggg tgtcgcggca  960
tga                                                                963

SEQ ID NO: 6             moltype = AA  length = 484
FEATURE                  Location/Qualifiers
source                   1..484
                         mol_type = protein
                         organism = Streptomyces chromofuscus
SEQUENCE: 6
MRAVDLRHPP YVFRSDDGVG PVPLLVIRPR RRPSVRLKLE QAESVILMGL RHITVIGTGY   60
VGLTTGACLA SLGHRVVCAD ADEGKVERLR RAEVDILEPG LTEVVREGLE SGRLQFVRDT  120
RAAVEEAEVV FLCLPTPMGV GGAADLAAVE AVADEVRDRL PRGCTVVNKS TVPVGTAERV  180
AALLGRPDVT VVSNPEFLRE GHAVDDFLHP DRIVVGAADA DAARLVADLY LDIDAPRVVT  240
DTAGAELAKY AANFFLAMKL SFANNLATLC ESLGANIDDV VAGIGHDPRI GGAFLKPGPG  300
WGGSCLPKDT HALLRVCEES GVEFPLLRAT IETNVEHQRR LVERVTAGCA GADGSLRGVR  360
IGLLGLTFKA GTFDLRDSPA LAIARLLRER GAELRAYDPA LSELRPDLGD LLTITGTPLE  420
AVDGARACVV LTEWPQFRDL DWEAVAGRLA APLVYDFRNI LDPARLDRAA LTWEGIGRSL  480
AMAS                                                               484

SEQ ID NO: 7             moltype = AA  length = 402
FEATURE                  Location/Qualifiers
source                   1..402
                         mol_type = protein
                         organism = Streptomyces chromofuscus
SEQUENCE: 7
VRVLFTTLGS PSHGRAQLPL ARAFAAAGHD VLVATTPTLA SVFEQDDVRV TVCMGDFTPQ   60
SFITPELLQE AMRPGQDGEP QDAMARLMPE ITSGPMARKL WEEILPVARE FAPDLILRDG  120
MDLSSCLIAE HLGIPQLPTP SGTNNLIDPA MVLPGLNVLR KEFGLSAQED PLSLVPHGRV  180
DYVPAAFSFA QHLPSSWSYR QTVTVDRSSV LPEWIAQLPT DRPLVFAALG TALPMIREMG  240
AEATGPSLFP MPDPVDTLRL MIEAVSRLDD CTVVVATSGI PADTEGLPPH VHVTDRVPQP  300
LLLESVDAFL THGGFNSIRE ALRTATPMAV LPQFGDQPAN ARRVEELGLG REITDITADG  360
ITKAVREVLT DPGIRARTRE ARLAMLALPE IDSAVADLQK IV                     402

SEQ ID NO: 8             moltype = AA  length = 320
FEATURE                  Location/Qualifiers
source                   1..320
                         mol_type = protein
                         organism = Streptomyces chromofuscus
SEQUENCE: 8
MSPSPPPATT VTKAVIPAAG LGTRFLPATK AMPKEMLPVV DRPAIQYVVE EAAGAGLSDL   60
LVITGRNKRP LEDHFDHAWE LEEALTRKGD EGRLRSVRES TALAAIHYVR QGTPAGLGHA  120
VLCAQQHVGD EPFAVLLGDD LIDPRDPLLT RMIEIRERFG GSVVALMETD PASIHLYGCA  180
AVEPTAQDDV VRLTDLVEKP APGQAPSAYA VIGRYLLDPA VFEVLRRTPP GHGGEIQLTD  240
ALRELAHGGA TSPGGPVHGV LFTGRRYDTG DRAEYLRTIV RLAYEHDDLG PGFREWLTAF  300
VDAEREAPTA AADGGPGVAA                                              320
```